(12) United States Patent
Thompson et al.

(10) Patent No.: US 7,587,329 B2
(45) Date of Patent: *Sep. 8, 2009

(54) METHOD AND SYSTEM FOR OPTIMIZING EMPLOYEE SCHEDULING IN A PATIENT CARE ENVIRONMENT

(75) Inventors: Bruce J. Thompson, Morrison, CO (US); Michael A. Dikeman, Montrose, CO (US)

(73) Assignee: Drason Consulting Services, LLC, Morrison, CO (US)

( * ) Notice: Subject to any disclaimer, the term of this patent is extended or adjusted under 35 U.S.C. 154(b) by 1162 days.

This patent is subject to a terminal disclaimer.

(21) Appl. No.: 10/645,440

(22) Filed: Aug. 20, 2003

(65) Prior Publication Data

US 2004/0039628 A1    Feb. 26, 2004

Related U.S. Application Data

(63) Continuation-in-part of application No. 09/872,292, filed on Jun. 1, 2001, now Pat. No. 7,457,765.

(60) Provisional application No. 60/209,107, filed on Jun. 2, 2000.

(51) Int. Cl.
*G06Q 90/00* (2006.01)
(52) U.S. Cl. .............................. 705/9; 705/8
(58) Field of Classification Search ............... 705/9
See application file for complete search history.

(56) References Cited

U.S. PATENT DOCUMENTS

| | | | | |
|---|---|---|---|---|
| 4,937,743 A | * | 6/1990 | Rassman et al. | 705/8 |
| 5,065,315 A | | 11/1991 | Garcia | 364/413.01 |
| 5,111,391 A | | 5/1992 | Fields et al. | 364/401 |
| 5,732,401 A | | 3/1998 | Conway | 705/29 |
| 5,748,907 A | | 5/1998 | Crane | 395/202 |
| 5,809,477 A | | 9/1998 | Pollack | 705/3 |
| 5,845,253 A | * | 12/1998 | Rensimer et al. | 705/2 |
| 5,913,201 A | | 6/1999 | Kocur | 705/9 |

(Continued)

FOREIGN PATENT DOCUMENTS

WO     WO 97/25862     7/1997

(Continued)

OTHER PUBLICATIONS

Ho et al. Introducing variable-interval appointment scheduling rules in service systems, International Journal of Operations and Production Management, vol. 15, No. 6, 1995.*

(Continued)

*Primary Examiner*—Andre Boyce
(74) *Attorney, Agent, or Firm*—Merchant & Gould PC

(57) ABSTRACT

A system and method for managing a health clinic, and in particular to managing/scheduling employees to work in the clinic. The system and method relates to a computer program for computing the needs of patients, determining adequate staffing requirements and displays these needs and requirements in connection with actual scheduling values. Thus, the system provides a tool for quickly determining whether the clinic is overstaffed or understaffed, for the entire day based on patient needs, both direct and indirect patient care needs. The system and method may further use facility limitation information to provide overall efficiency information.

35 Claims, 52 Drawing Sheets

U.S. PATENT DOCUMENTS

| | | | |
|---|---|---|---|
| 5,923,018 A | 7/1999 | Kameda et al. | 235/385 |
| 5,924,074 A | 7/1999 | Evans | 705/3 |
| 5,970,466 A * | 10/1999 | Detjen et al. | 705/8 |
| 5,991,728 A | 11/1999 | DeBusk et al. | 705/2 |
| 5,995,937 A * | 11/1999 | DeBusk et al. | 705/2 |
| 6,044,355 A * | 3/2000 | Crockett et al. | 705/8 |
| 6,278,978 B1 * | 8/2001 | Andre et al. | 705/9 |
| 6,640,212 B1 * | 10/2003 | Rosse | 705/9 |
| 6,732,079 B1 * | 5/2004 | Kintner et al. | 705/8 |
| 6,823,315 B1 * | 11/2004 | Bucci et al. | 705/9 |
| 6,970,829 B1 * | 11/2005 | Leamon | 705/9 |
| 2002/0026342 A1 * | 2/2002 | Lane et al. | 705/8 |

FOREIGN PATENT DOCUMENTS

WO  WO 97/40463  10/1997

OTHER PUBLICATIONS

International Search Report for PCT/US01/17837.

* cited by examiner

HOURS PER TREATMENT REPORT

GENERAL

SUMMARY

| | |
|---|---|
| REPORT DATE: | 05/28/2001 |
| TOTAL TREATMENTS: | 25 |
| PATIENT CARE HOURS WORKED: | 29.38 |
| PATIENT CARE HPT: | 1.18 |
| ADMINISTRATIVE HOURS WORKED: | 17.63 |
| ADMINISTRATIVE HPT: | 0.71 |
| TOTAL HPT: | 1.88 |

ADJUSTMENTS TO HOURS WORKED ARE CALCULATED AS FOLLOWS:
1/2 HOUR LUNCH FOR EACH SHIFT OVER 4 1/2 HOURS LONG.

670 — (pointing to ADMINISTRATIVE HOURS WORKED)

PRINT
CANCEL

Ideal Staffing Model — 4100

NRAA 2002     Medicare ID: 00-0000

Ideal Staffing Model
July 15, 2003

| Total Patient Care HPT | | Actual | | Ideal | | Variance | |
|---|---|---|---|---|---|---|---|
| | | Total Hrs Less Lunch | HPT 19 | Total Hrs Less Lunch | HPT 19 | Total Hrs Less Lunch | HPT 19 |
| Actual Daily Treatments Delivered: | 19 | | | | | | |
| RN DPC Staff | | 10.00 | 0.53 | 5.93 | 0.31 | (4.07) | (0.21) |
| Non-RN DPC Staff | | 32.50 | 1.71 | 26.69 | 1.40 | (5.81) | (0.31) |
| Total | | 42.50 | 2.24 | 32.62 | 1.72 | (9.88) | (0.52) |

| Direct Patient Care HPT | | Actual | | Ideal | | Variance | |
|---|---|---|---|---|---|---|---|
| | | DPC Hrs Less Breaks | HPT 19 | DPC Hrs Less Breaks | HPT 19 | DPC Hrs Less Breaks | HPT 19 |
| Actual Daily Treatments Delivered: | 19 | | | | | | |
| RN DPC Staff | | 7.00 | 0.37 | 5.34 | 0.28 | (1.66) | (0.09) |
| Non-RN DPC Staff | | 30.25 | 1.59 | 21.35 | 1.12 | (8.90) | (0.47) |
| Total | | 37.25 | 1.96 | 26.69 | 1.40 | (19.56) | (0.56) |

| Ideal Assumptions Ratio's | | Actual | | Ideal | | Variance | |
|---|---|---|---|---|---|---|---|
| | | Total Dollars Less Lunch | CPT 19 | Total Dollars Less Lunch | CPT 19 | Total Dollars Less Lunch | CPT 19 |
| % RN to Staff Mix (i.e. 1 to 3=25%) | 20% | $190.00 | $10.00 | $109.72 | $5.77 | ($80.00) | ($4.23) |
| % RN to Staff DirectPatientCare (DPC) | 90% | $380.00 | $20.00 | $293.56 | $15.45 | ($86.44) | ($4.23) |
| % RN to Staff DirectPatientCare (DPC) | 80% | $5.70.00 | $30.00 | $403.28 | $21.23 | ($166.72) | ($8.77) |
| % Allowance for Intermittent Acuity | 20% | | | | | | |

Page 1 of 3     printed on: 07/15/2003

Ideal Staffing Model

NRAA 2002  Medicare ID: 00-0000

Ideal Staffing Model
July 15, 2003

| Patient Treatment Activities | Actual DPC Activity | | | Actual DPC Staff Mix | |
|---|---|---|---|---|---|
| Actual Daily Treatments Delivered: | Activity Time Min | # of Activities | DPC Hours | RN 20% | Non-RN 80% |
| Setup 1  S  Setup Time (standard) | 12.0 | 17 | 3.40 | 0.68 | 2.72 |
| Setup 2  s  Setup Time (complex) | 10.0 | 4 | 0.67 | 0.13 | 0.53 |
| Run  R  Run Time PT Monitoring (standard) | 3.0 | 285 | 14.25 | 2.85 | 11.40 |
| Monitor  m  Run Time PT Monitoring (complex) | 5.0 | 10 | 0.83 | 0.17 | 0.67 |
| Takeoff 1  T  Setup Time (standard) | 6.0 | 17 | 1.70 | 0.34 | 1.38 |
| Takeoff 2  t  Takeoff Time (complex) | 7.5 | 4 | 0.50 | 0.10 | 0.40 |
| Disinfect  d  Disinfect Machine | 1.0 | 0 | 0.00 | 0.00 | 0.00 |
|  |  | 337 | 21.35 | 4.27 | 17.08 |
|  |  |  | 5.34 | 1.07 | 4.27 |
|  |  |  | 26.69 | 5.34 | 21.35 |

Allowance of Intermittent Acuity   20%

| Patient Treatment Activities | | | | | | | |
|---|---|---|---|---|---|---|---|
| Job Type | % DPC | Shift Activity | Employee Status | % DPC | Total Hours | Admin Total | DPC Hours |
| RN | 90% | Direct Patient Care | AVAIL DPC | 100% | 5.93 | 0.59 | 5.34 |
| Non-RN | 80% | Direct Patient Care | AVAIL DPC | 100% | 26.59 | 5.34 | 21.35 |
| Total |  |  |  |  | 32.62 | 5.93 | 26.69 |

Page 2 of 3   printed on:07/15/2003

FIG.42

Ideal Staffing Model — 4300

NRAA 2002      Medicare ID: 00-0000

Ideal Staffing Model
July 15, 2003

| | | | | | \multicolumn{6}{c}{Actual Patient Care Hours} | |
|---|---|---|---|---|---|---|---|---|---|---|
| Job Type | % DPC | Shift Activity | Employee Status | % DPC | Total Hours | Admin Lunch | Admin Breaks | Admin Job Type | Admin EE Status | Admin Total | DPC Hours |
| C-E-RNT | 75% | DPC | | 100% | 10.50 | (0.50) | (0.50) | (2.50) | 0.00 | (3.50) | 7.00 |
| | | | | | 10.50 | (0.50) | (0.50) | (2.50) | 0.00 | (3.50) | 7.00 |
| C-E-PNS | 100% | DPC | | 100% | 11.50 | (0.50) | (0.75) | 0.00 | 0.00 | (1.25) | 10.25 |
| C-E-PCT | 100% | DPC | | 100% | 11.25 | (0.50) | (0.75) | 0.00 | 0.00 | (1.25) | 10.00 |
| C-E-PCT | 100% | DPC | | 100% | 11.25 | (0.50) | (0.75) | 0.00 | 0.00 | (1.25) | 10.00 |
| | | | | | 34.00 | (1.50) | (2.25) | 0.00 | 0.00 | (3.75) | 30.25 |
| | | | | | 44.50 | (2.00) | (2.75) | (2.50) | 0.00 | (7.25) | 37.25 |

Page 3 of 3      printed on: 07/15/2003

| Code | Description | % DPC | Schedule Allowed | Schedule Active |
|---|---|---|---|---|
| AVAIL ADM | Available Administrative Duties | 0% | ☒ | ☐ |
| AVAIL DPC | Available Direct Patient care | 100% | ☒ | ☐ |
| DISA | Disability - Limited Duty | 50% | ☐ | ☒ |
| FMLA | Family Leave | 0% | ☐ | ☒ |
| GRIEF | Bereavement Leave | 100% | ☐ | ☒ |
| JURY | Jury Duty | 0% | ☐ | ☒ |
| LOA | Leave of Absence | 0% | ☐ | ☒ |
| OUT | No Paid Time Off | 0% | ☐ | ☐ |
| PEND | Pending Employee Start Date | 0% | ☒ | ☐ |
| PTO | Paid Time Off | 25% | ☒ | ☐ |
| SICK | Sick Leave | 50% | ☐ | ☒ |
| SUSPEND | Suspend from Active Duties | 75% | ☐ | ☐ |
| TERM | Terminated | 0% | ☐ | ☒ |
| TRN1 | Trainee 1st Phase | | | |
| TRN2 | Trainee 2nd Phase | | | |
| TRN3 | Trainee 3rd Phase | | | |
| VAC | Vacation Leave | 0% | ☐ | ☐ |
| XFER | Transferred | 0% | ☐ | ☐ |

METHOD AND SYSTEM FOR OPTIMIZING EMPLOYEE SCHEDULING IN A PATIENT CARE ENVIRONMENT

RELATED APPLICATION

This application claims the benefit under 35 U.S.C. §120 as a Continuation-In-Part of Ser. No. 09/872,292 now U.S. Pat. No. 7,457,765, entitled Method and System for Scheduling Employees in a Patient Care Environment, filed Jun. 1, 2001, which claims the benefit under 35 U.S.C. §119(e) of U.S. Provisional Application 60/209,107, entitled SCHEDULING SYSTEM, filed Jun. 2, 2000 by Bruce Thompson, which applications are also hereby incorporated by reference in their entirety.

TECHNICAL FIELD

This invention relates generally to scheduling employees and more particularly to computer-aided systems for scheduling employees. More particularly, the present invention relates to computer-aided systems for scheduling employees and/or patients in order to properly handle the many and various patient-care activities arising in a clinical environment especially wherein patients require a variable amount of employee attention during a visit to the clinic.

BACKGROUND OF THE INVENTION

In health care, given the importance of patient safety, maintaining an adequate staffing schedule is highly important to insure that the relative needs of the patients are satisfied. In order to adequately staff typical health-care locations, such as specialized clinics, several factors are typically considered. For instance, for a particular day, clinics typically determine the relative needs of each of the scheduled patients and schedule enough employees to handle these needs. The decision making is fairly individualized, such that for each patient, at least one employee is assigned the task of taking care of that patient's needs. These needs may be determined based on previous visits by a patient, especially in a clinic that provides regular, continual treatments to its patients, such as a dialysis clinic.

Additionally, clinics typically account for possible emergency situations and/or patients requiring additional treatment, i.e., treatment that was not scheduled. Since these events are not foreseeable but may occur, the clinics typically schedule some additional employees to handle these situations. When determining the number of employees to schedule, clinics therefore typically schedule employees based on a worst-case scenario to make sure that plenty of qualified employees work each day.

Unfortunately however, these worst-case scenarios do not happen regularly, such that many clinics are generally overstaffed, which reduces the efficiency of the clinic. Moreover, many clinics lose efficiency by scheduling employees based on peak patient requirements wherein the peaks last a relatively short period of time, such that the clinic is over-staffed during other, non-peak time periods. Additionally, clinics often schedule many patient activities to occur at approximately the same time of the day such that many if not all the employees are busy during that time but are then idle for the remaining time, or until the next intermittent peak of activities occurs. Consequently, due to the lack of worst-case scenarios and unfortunate timing of patient activities, typical clinics are overstaffed and not as efficient as they might be.

It is with respect to these and other considerations that the present invention has been made.

SUMMARY OF THE INVENTION

The present invention relates to a system and method for managing a health clinic, and in particular to managing/scheduling employees to work in the clinic. In a particular embodiment of the invention, the system and method relates to a computer program for computing the needs of patients, determining adequate staffing requirements and displays these needs and requirements in connection with actual scheduling values. Thus, the system provides a tool for quickly determining whether the clinic is overstaffed or understaffed, for the entire day based on patient care needs. Moreover, the system automatically determines schedule possibilities to improve efficiency for both patients and staff. In doing so, the present invention utilizes "drivers" or predetermined values based on business rules or decisions to create an optimized schedule.

In a particular embodiment, the scheduling method and system is used in a clinic that performs dialysis on patients and has a specific number of chairs or machines that can be used to perform the dialysis. The limitation of resources necessarily limits the number of patients that can be serviced at any time in the day. For this reason, the invention is helpful to schedule these patients in relation to the actual examination rooms, machines or chairs. Additionally, dialysis patients typically require differing amounts of care by licensed nurses or other capable, non-licensed, technical employees of the clinic. This added variable increases the difficulty in trying to staff a clinic in the most efficient manner, i.e., so that there are not too many or too few employees scheduled on a daily basis based on employee skill requirements for that day, which accordingly are dependent on individual patient treatment activity requirements.

In accordance with certain aspects, the present invention relates to a system and method of scheduling a plurality of patients and a plurality of employees in a health care environment, wherein at least two patients receive treatment during a predetermined time period. Patient care requirements are evaluated for each patient, wherein the patient care requirements relate to actual employee time necessary to satisfy the patient care requirements. Also, in response to the patient care requirement evaluation, the scheduled time of at least one patient is adjusted in order to distribute the associated employee time requirements throughout a predetermined time period, such as a day. Additionally, employees are scheduled in response to the distributed employee time requirements.

In accordance with other aspects, the inventive method further relates to dividing the day into intervals and, in evaluating the patient care requirements, determining the patient care requirements on a per-interval basis. The patient care requirements may then be averaged over more than one interval. In another embodiment, a plurality of job types are predetermined, each job type having a different patient care capability value associated with each job type and wherein the method further relates to scheduling shifts of employees based on job type and then scheduling employees based on scheduled job type.

In accordance with other aspects, the present invention relates to a method of scheduling employees wherein the patient care capability value of each employee is averaged over an entire shift. The method further involves displaying a plurality of patient schedules in relation to time to provide a visual indication of the patient care requirements for each interval. The method may further calculate patient requirement values related to required employee based on the patient care requirements for a plurality of intervals and display the calculated values. These values may further be displayed along with employee shift information to provide a visual indication of scheduled employee information in relation to scheduled patient information. Moreover, the values may be compared, as between the patient requirement values and employee values, for each interval to determine efficiency.

In accordance with yet other aspects, an embodiment of the invention schedules employees in a health care environment by compiling a plurality of patient profiles, each profile associated with a different patient, and wherein each profile comprises information related to the direct patient care needs of the associated patient; compiling a plurality of employee profiles, each profile associated with a different employee and wherein each profile comprises information related to the patient care capability of the associated employee; calculating efficiency information relating to a generated schedule of patients and employees based on the patient profiles and employee profiles; and adjusting the schedule to generate a more efficient schedule. In another embodiment, a system that schedules the employees has a memory store for storing patient information related to the needs of a plurality of patients, resource information and employee information related to patient care capability of a plurality of patients; a scheduling module that schedules patients and employees according to patient needs; and a display unit for displaying the scheduled patient information in combination with scheduled employee information, the display providing efficiency information, such as in a graphical user interface.

The invention may be implemented as a computer process, a computing system or as an article of manufacture such as a computer program product. The computer program product may be a computer storage medium readable by a computer system and encoding a computer program of instructions for executing a computer process. The computer program product may also be a propagated signal on a carrier readable by a computing system and encoding a computer program of instructions for executing a computer process.

A more complete appreciation of the present invention and its improvements can be obtained by reference to the accompanying drawings, which are briefly summarized below, to the following detail description of presently preferred embodiments of the invention, and to the appended claims.

BRIEF DESCRIPTION OF THE DRAWINGS

FIG. 6 is a screen shot diagram illustrating the graphical display of the management system shown in FIG. 1, the display having a patient scheduling portion, an employee scheduling portion and calculation display region according to an embodiment of the present invention.

FIG. 7 is a screen shot diagram illustrating the display shown in FIG. 6 populated with sample scheduling data according to an embodiment of the present invention.

FIG. 8 is a screen shot diagram illustrating a pop-up menu for editing data related to a patient according to an embodiment of the present invention.

FIG. 9 is a screen shot diagram of a patient profile window for entering the profile of a patient that may be scheduled according to the present invention according to an embodiment of the present invention.

FIG. 10 is a screen shot diagram illustrating a pop-up menu for editing a data related to an employee or employee job type according to an embodiment of the present invention.

FIG. 11 is a screen shot diagram of an employee job-type window for entering or editing information related to job-types according to an embodiment of the present invention.

Figure 12:
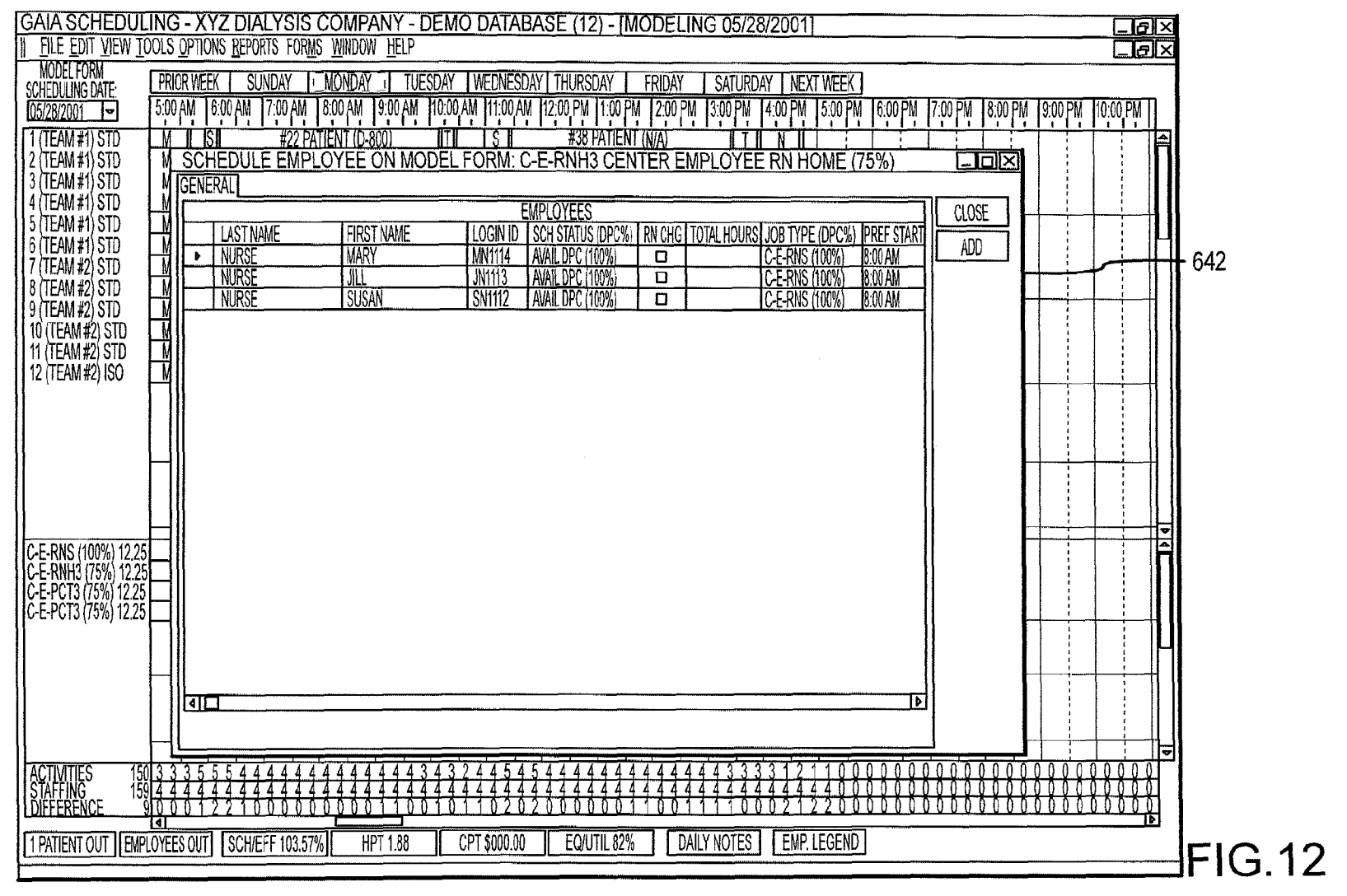

FIG. 12 is a screen shot diagram of a pop-up window for scheduling an employee according to an embodiment of the present invention.

FIG. 13 is a screen shot diagram illustrating a pop-up, cascading menu for editing shift activities for a shift according to an embodiment of the present invention.

FIG. 14 is a screen shot diagram illustrating a legend of colors indicating assigned shift activities according to an embodiment of the present invention.

FIG. 15 is a screen shot diagram illustrating an information box according to an embodiment of the present invention.

FIG. 16 is a screen shot diagram illustrating a pull-down menu of viewable and editable lists according to an embodiment of the present invention.

FIGS. 17 and 18 are screen shot diagrams illustrating viewable and editable lists according to an embodiment of the present invention.

FIGS. 19, 20 and 21 are screen shot diagrams illustrating different pull-down menus according to an embodiment of the present invention.

FIGS. 22 and 23 are screen shot diagrams illustrating different viewable records according to an embodiment of the present invention.

FIG. 26 is a screen shot illustrating the set of drivers used by the optimization module in a particular embodiment of the present invention.

FIG. 27 is a screen shot illustrating employee needs based on the predetermined needs, i.e., the existing patient schedule.

FIG. 28 is a screen shot illustrating the set of potential shift times provided by the system in accordance with a particular embodiment of the present invention.

FIG. 29 is a screen shot illustrating a recommended employee schedule based on patient needs, the existing driver values, and the selected shift times in an embodiment of the present invention.

FIG. 32 is a screen shot illustrating a schedule portion of an example patient profile, the schedule portion providing an acuity factor in an embodiment of the present invention.

FIG. 33 is a screen shot illustrating a schedule portion of an example patient profile, the schedule portion providing an acuity factor selection option and further illustrating acuity arrays in an embodiment of the present invention.

FIG. 34 is a screen shot illustrating a drop down menu to access and edit patient treatment activities in accordance with an embodiment of the present invention.

Figure 36:
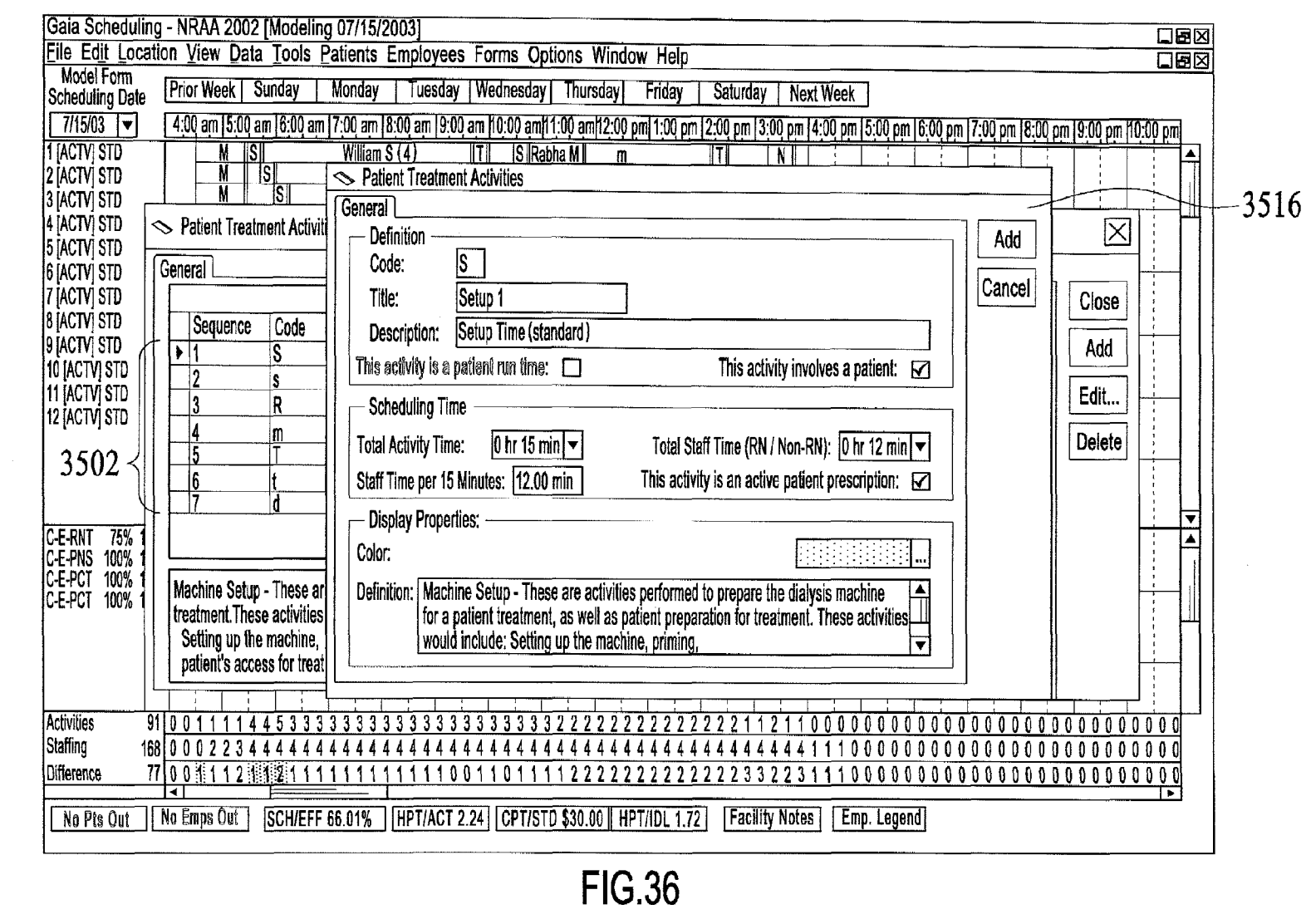

FIGS. 35 and 36 are screen shots illustrating pop-up windows used to view and edit patient treatment activities in accordance with an embodiment of the present invention.

FIG. 37 is a screen shot illustrating a drop down menu to access and edit patient acuity arrays in accordance with an embodiment of the present invention.

Figure 39:
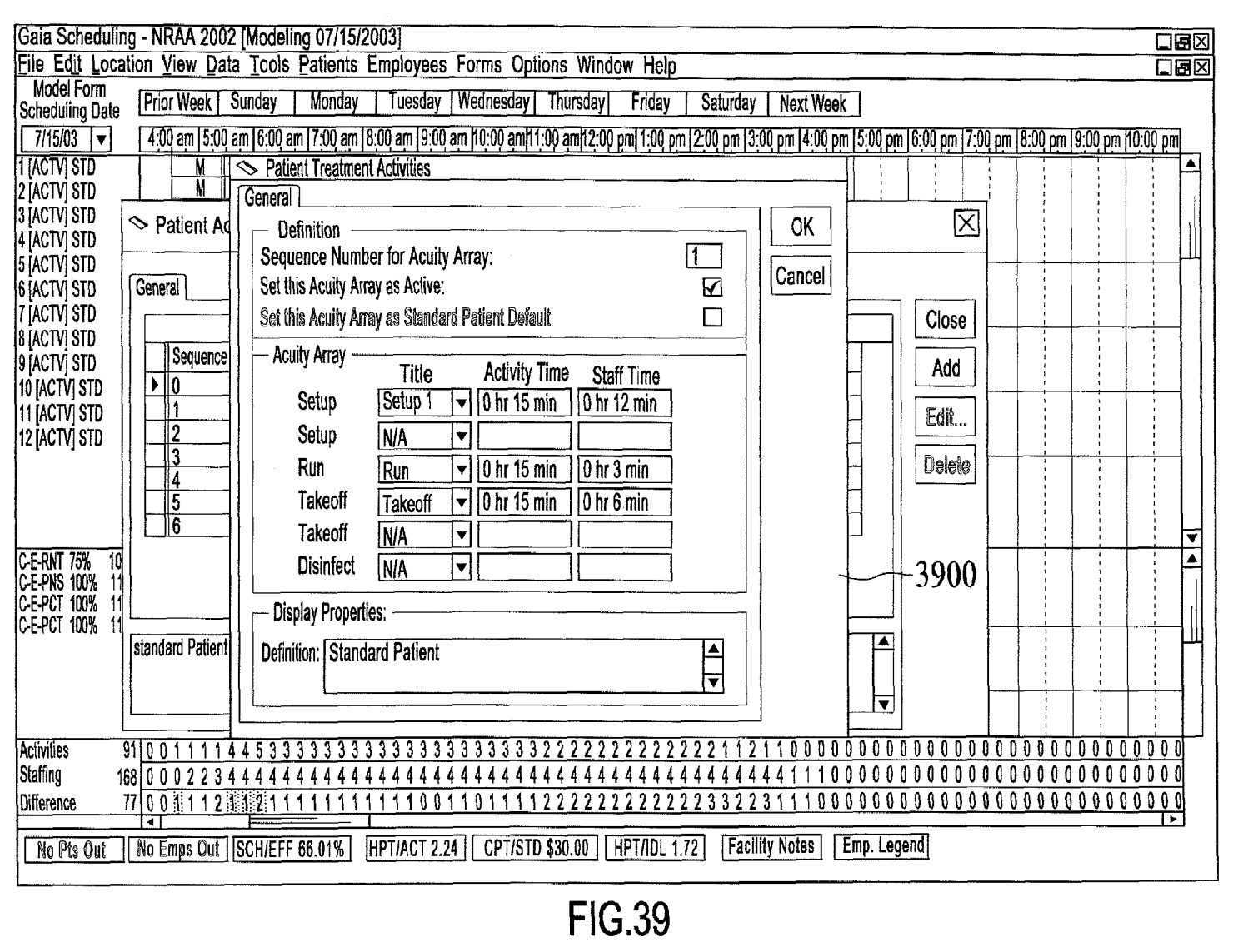

FIGS. 38 and 39 are screen shots illustrating pop-up windows used to view and edit patient acuity arrays in accordance with an embodiment of the present invention.

FIGS. 40-43 are screen shots illustrating generated reports based on existing sets of patient and employee schedules.

FIGS. 44-46 are screen shots illustrating user interface controls for displaying and editing an employee status, such as whether the employee is out for the day, in accordance with an embodiment of the present invention.

FIG. 47 is a screen shot illustrating a drop-down menu that allows a user to adopt a model form view for a particular day, in accordance with an embodiment of the present invention.

FIGS. 48-50 are screen shots illustrating user interface controls for displaying and editing a patient status, such as whether the patient is out for the day, in accordance with an embodiment of the present invention.

FIGS. 51-52 are screen shots illustrating user interface controls for displaying the operational definition of a particular portion shown on the user interface, in accordance with an embodiment of the present invention.

DETAILED DESCRIPTION OF THE INVENTION

Figure 1:
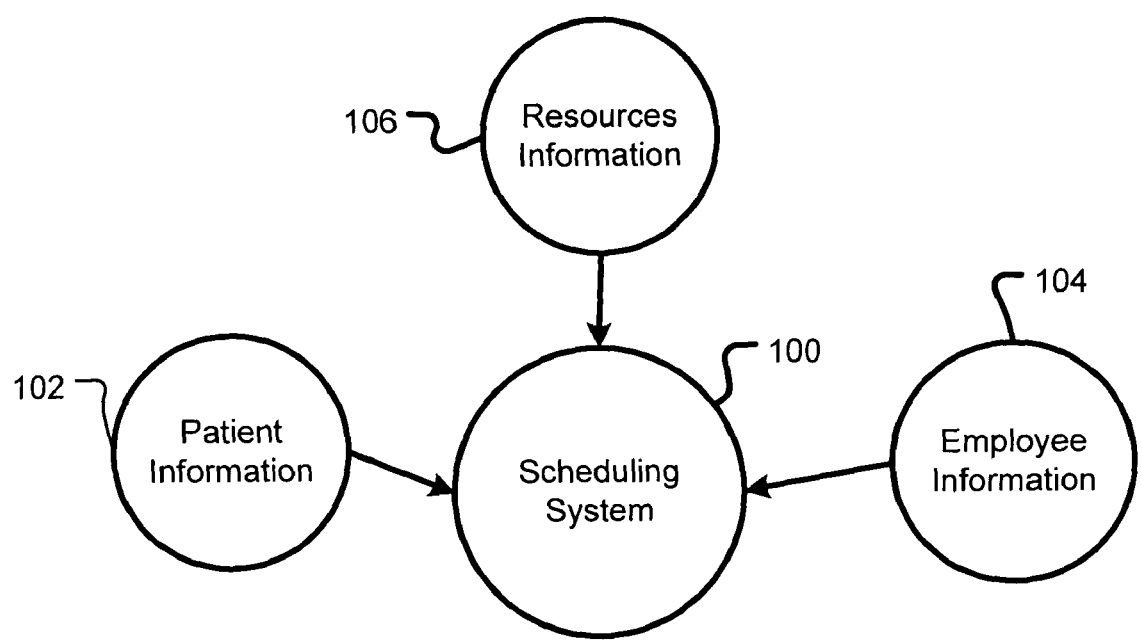
FIG. 1 is a diagram illustrating patient information and employee information in relation to a system for managing that information in accordance with aspects of the present invention.

A scheduling system 100 incorporating aspects of the present invention is shown in FIG. 1. The scheduling system 100 provides an automated system of creating a comprehensive schedule, taking into account the various needs and limitations of patients or "patient requirements," employees and available resources and displays all the necessary information for a user to quickly and readily identify inefficiencies in the schedule. The system 100 also provides an archival system for past and future services and report generating capabilities relating to efficiency calculations.

In an embodiment, the system 100 maintains various schedules for a "health service provider." As used herein, a "health service provider" provides predetermined health services and has the resources to do so, the resources relating to the employees, machines, treatment areas, and other items needed to accommodate various needs of patients. Particular health services may involve dialysis treatments or some other specialized health care treatment provided to patients on a relatively regular basis and wherein the treatment requires some amount of direct patient care administered by an employee of the health service provider. Although discussed herein with respect to dialysis treatments in a dialysis clinic, the present invention may be used to schedule requirements and employees in many other situations wherein employees have numerous and varied tasks and wherein the actual time needed to complete the tasks may be averaged over the course of an employee's shift.

The system 100 stores and uses patient information 102 which relates to specific patient needs and limitations and the types of services that are to be provided to the patient by the health service provider. For instance the patient information may relate to the number of hours needed to complete a visit and the types or amount of patient care, whether direct or indirect, that will be needed during each step in the delivery of care for each visit. The information may further include other requirements, e.g., limitations or restrictions relating to specific health conditions, etc. These requirements may affect the amount of direct patient care or indirect patient care that should be provided to the patient during a visit.

As used herein, the term "direct patient care," relates to direct attention paid to a patient such that the employee cannot handle any other task during the time the employee is providing direct patient care. Typically, the amount of direct patient care required by a patient can be predetermined based on past visits. That is, since many patients typically visit specialized clinics on a repeated, continual and regular basis, data may be collected relating to a patient's direct patient care needs. For example a patient may require approximately one and one-half hours of direct patient care during a four-hour visit, including initiating the dialysis treatment, administering the treatment, checking the machine or handling other more immediate tasks. Importantly however, a portion of the predetermined direct patient care relates to tasks that can be performed at different times, and are not necessarily performed at a specific time within the scheduled appointment.

The system 100 also stores information 104 related to the physical resources available. These types of resources may relate to reusable resources that may be allocated to a predetermined number of patients at a particular time. For example, the physical resources may relate to rooms, dialysis chairs or machines, etc. that may be allocated to a single patient at a time. Moreover, the system 100 may also store information related to the specific scheduling issues for the physical resources. As an example, a dialysis machine may not be allocated for patient care at all times, as the machine must be cleaned or otherwise disinfected between uses and the machine may need to be set up or otherwise configured for the next patient, such configuration may take a significant amount of time and the system 100 may plan for these particular requirements.

System 100 also stores and uses employee information 106 which has employee profile information. The employee profile information relates to employee scheduling requirements as well as employee capabilities. For instance, some employees may only be able to provide direct patient care on a limited basis, either because of other required duties or because of some other limitation, e.g., the employee is not fully trained or licensed for certain tasks. Additionally, the employee profile may indicate what job-type that person is qualified to perform.

In an embodiment of the invention, the employee information 106 includes model job types, such as a model for a certified nurse, a non-certified nurse, a technician, etc. These job types have certain, predetermined properties, such as whether the job type provides for direct patient care, and how much, as discussed below. In another embodiment the information 106 has other information related to shift activity. Shift activity information is provided to temporarily change the activity assigned to an employee, which may potentially change the amount of direct patient care that employee may perform during that shift. The information 106 may further relate to other activities such as indirect patient care, which may include maintaining facility resources, etc., that a clinic may want to monitor in order to determine overall staffing and scheduling efficiency.

The system 100 uses the information 102, 104 and 106 to provide a resulting schedule of patient visits and employee shifts. The schedule is a daily schedule but could be set up on another basis. The daily schedule is divided into intervals, such as fifteen-minute intervals and displays values related to the patient needs and/or the number of employees required to satisfy those needs on a per-interval basis. In an embodiment, the system displays each patient schedule portion with associated patient care tasks to provide a quick reference as to the needs of each patient with respect to the needs of the other patients with respect to the time of day. Thus, the patients' needs may be quickly viewed as creating a peak or inefficiency period. The system may also provide a means of adjusting, automatically, the various patient schedules to more adequately distribute the relative needs of the various patients over the course of the day to thereby provide a more efficient environment, e.g., an environment wherein fewer scheduled employees satisfy the needs of the patients. Thus, the system 100 also provides the capability to optimize a patient schedule, as well as the capability to quickly identify patient needs that are not evenly distributed, to therefore more evenly distribute, automatically, the needs of patients.

The system 100 also displays the employees that are scheduled to work during the day and also displays a value related to the number of employees that are scheduled to work and are qualified to satisfy the patient needs, on a per interval basis. Displaying such employee information along with each employee's ability to provide direct patient care, even if partial, provides a quick reference in determining whether an adequate number of capable employees have been scheduled for the day, as discussed in more detail below. The system may also display other activities performed by the employees such as indirect patient care activities and management or other non-patient care activities to provide a relatively complete picture of employees and associated assignments in relation to patient needs and/or facility resources.

Furthermore, in a particular embodiment, the system 100 provides a system that calculates a relatively optimized employee schedule based on a given patient schedule. The system 100 uses predetermined drivers, i.e., predetermined numeric values that drive the optimization of employee schedules. The drivers are based on business rules that enable a user, clinic, or business to achieve efficient scheduling of direct patient care employees while maintaining business objectives. For example, the system 100 allows the user to set a business rule relating to the number of nurses to be staffed compared with the number of employees providing direct patient care without nursing qualifications. Consequently, the system recognizes when to staff a nurse instead of another employee based on the pre-defined business rule relating to the allowable nurse to non-nurse ratio. Other drivers are used to provide an efficient, yet customizable employee schedule for different businesses with different business models, as described in more detail below. Using these drivers, the system 100 automatically calculates and displays model forms for employee requirements and employee staff models to handle the patient needs for a particular day. A user may then adopt an employee staff model and use the same to schedule actual employees, creating an actual employee schedule.

Figure 2:
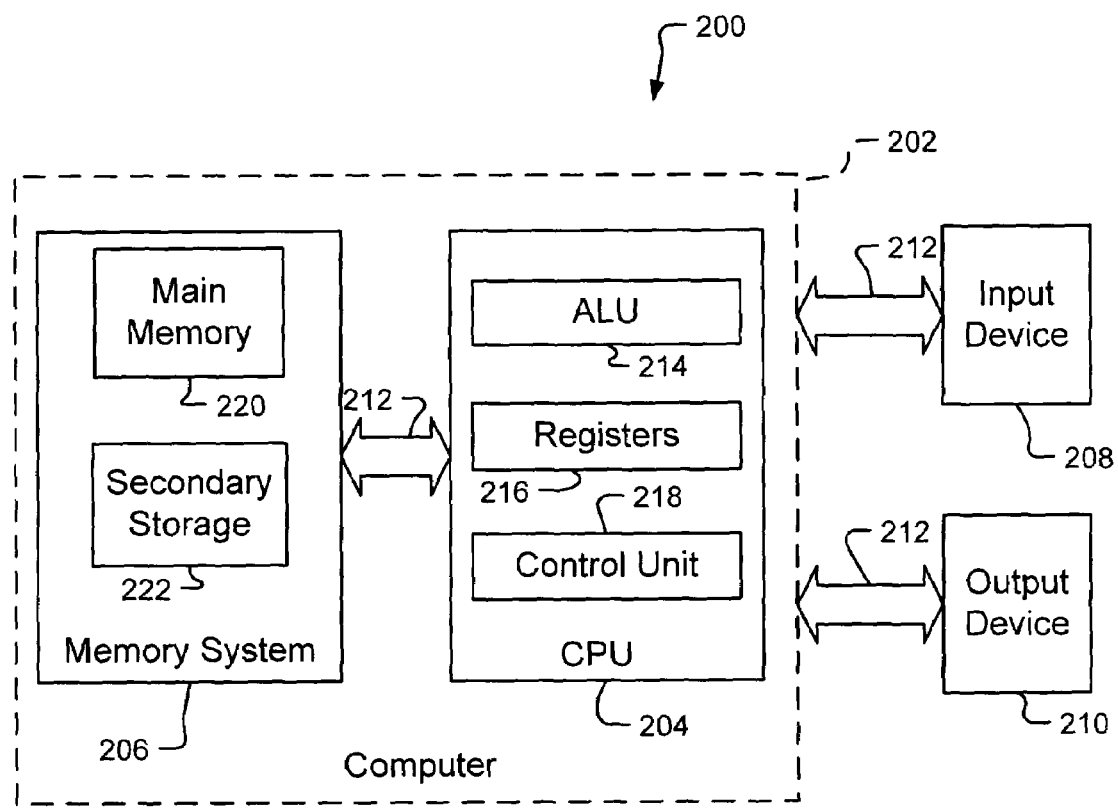
FIG. 2 is a functional diagram of a computer system having a memory that stores information related to patients and employees and a microprocessor to compute needs and requirements that may incorporate aspects of the present invention.

In an embodiment of the invention, the system 100 incorporates at least one computer system, such as computer system 200 shown in FIG. 2. The following discussion, in conjunction with FIG. 2, is intended to provide a brief, general description of a suitable computing environment in which the invention may be implemented. Although not required, the invention is described in the general context of computer-executable instructions, such as program modules, being executed by a personal computer. Generally, program modules include routines, programs, objects, components, data structures, etc. that perform particular tasks or implement particular abstract data types. Moreover, those skilled in the art will appreciate that the invention may be practiced with other computer system configurations, including handheld devices, multiprocessor systems, microprocessor-based or programmable consumer electronics, network PCs, minicomputers, mainframe computers, and the like. The invention may also be practiced in distributed computing environments where tasks are performed by remote processing devices that are linked through a communications network. In a distributed computing environment, program modules may be located in both local and remote memory storage devices.

The scheduling system 100 (shown in FIG. 1) incorporates a computer system 200 of computer resources for implementing an embodiment of the invention, as shown in FIG. 2. The system 200 incorporates a computer 202 having at least one central processing unit (CPU) 204, a memory system 206, an input device 208, and an output device 210. These computer resources 206 and 208 are coupled to computer 202 by at least one system bus 212.

The CPU 204 is of familiar design and includes an Arithmetic Logic Unit (ALU) 214 for performing computations, a collection of registers 216 for temporary storage of data and instructions, and a control unit 218 for controlling operation of the system 200. The CPU 204 may be a microprocessor having any of a variety of architectures including, but not limited to those architectures currently produced by Intel, Cyrix, AMD, IBM and Motorola.

The system memory 206 is some form of computer readable media. Computer readable media can be any available media that can be accessed by 202. By way of example, and not limitation, computer readable media may comprise computer storage media and communication media. Computer storage media, shown as main memory 220 and secondary storage 222, includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by 202. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

Memory devices within the memory system and their associated computer readable media provide non-volatile storage of computer readable instructions, data structures, programs and other data for the computer system.

The system bus 212 may be any of several types of bus structures such as a memory bus, a peripheral bus or a local bus using any of a variety of bus architectures.

The input and output devices are also familiar. The input devices 208 can comprise a small keyboard, a touch pad, a touch screen 102, etc. The output devices 210 can comprise a display, such as display 102 (FIG. 1), a printer (not shown), speaker 108, etc. Some devices, such as a network interface or a modem can be used as input and/or output devices. The input and output devices 208 and 210 are connected to the computer through system buses 212 as shown in FIG. 2.

The computer system 200 further comprises an operating system and usually one or more application programs. The operating system comprises a set of programs that control the operation of the system 200, control the allocation of resources, provide a graphical user interface to the user, facilitate access to local or remote information, and may also include certain application programs such as scheduling software as discussed below. An application program is software that runs on top of the operating system software and uses computer resources made available through the operating system to perform application specific tasks desired by the user. In general, an application is responsible for generating displays and interpreting the user input through the interface input elements.

Although the hardware operating environment is shown in FIG. 2, the present invention may be described in the general context of a software operating environment, e.g., computer-executable instructions, such as program modules, being executed by a computer, such as computer 202. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

Figure 3:
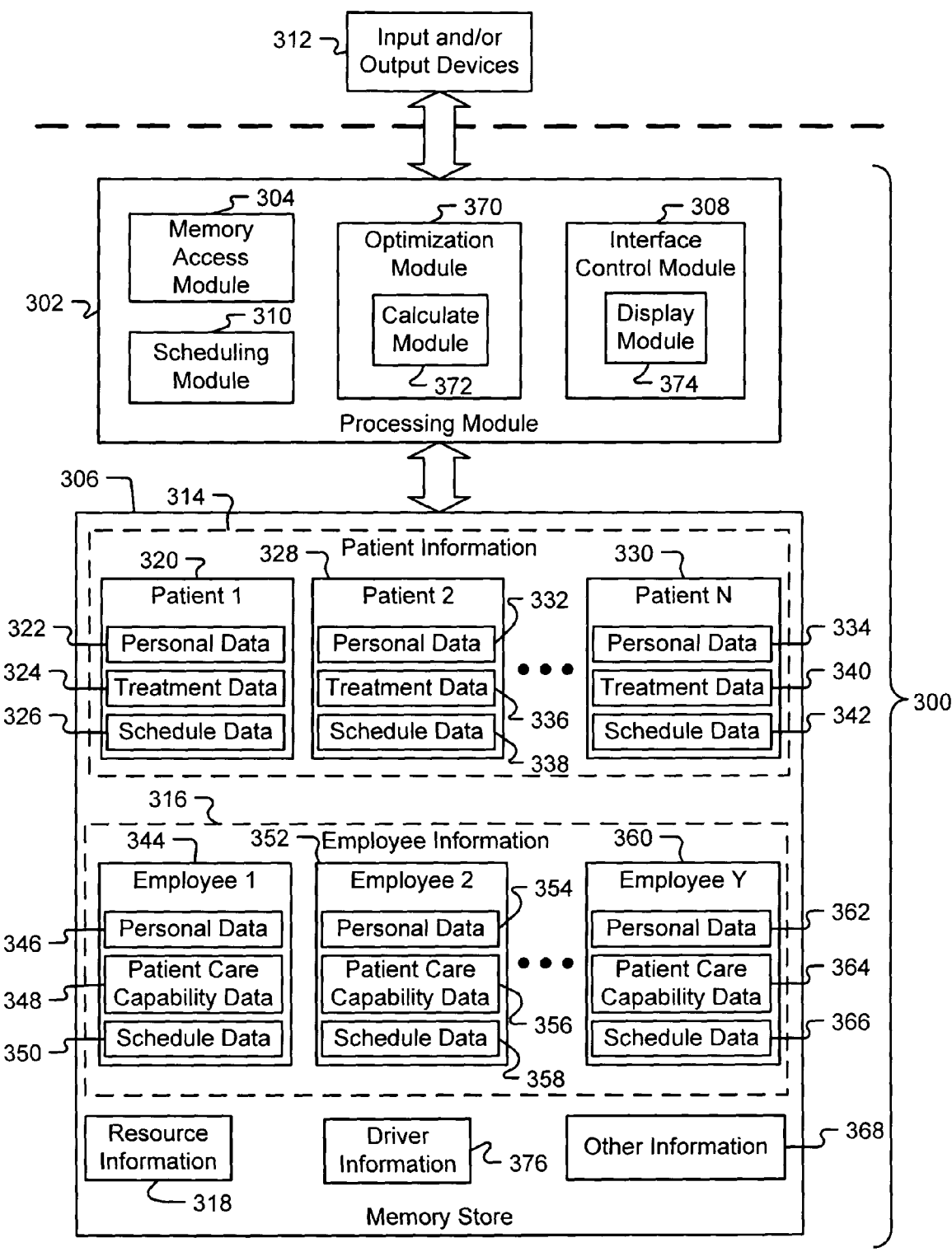
FIG. 3 is a block diagram illustrating software components of the present invention, the software components including patient and employee records, driver information, and an optimization module for generating an optimized employee schedule.

FIG. 3 illustrates an example of a software operating environment 300 in which the invention may be implemented. The software operating environment 300 is only one example of a suitable operating environment and is not intended to suggest any limitation as to the scope of use or functionality of the invention. Software environment 300 incorporates a processing module 302 that includes a number of sub-modules used to perform aspects of the present invention. For instance, the module 302 has a memory access module 304 to store and retrieve information to and from a memory store 306. The module 302 also has an interface module 308 that interfaces with the input and output devices 312 (such as input and output devices 208 and 210, respectively, shown in FIG. 2) to receive input information and to produce output information. Additionally, the module 302 has a scheduling module 310 for calculating scheduling information based on information in memory store 306. As discussed in more detail below, the processing module further includes an optimization module 370, used to optimize the respective schedules of the patients and the employees.

The memory store 306 comprises at least four types of information, patient information 314, employee information 316, resource information 318 and driver information 376.

With respect to the patient information 314, in an embodiment, the information is divided into records or profiles wherein each patient has a profile. An example profile is illustrated as 320 for "patient 1". The profile 320 includes information related to the patient, such as personal information, e.g., name, address, sex, birth date, etc., which is illustrated as personal data 322. The profile also has other patient information such as treatment information 324 and scheduling information 326, the combination of the two defining patient requirements for the particular patient. Treatment information 324 relates to the general type of treatment the patient typically needs or receives. The treatment information 324 may further include other restrictions or limitations that a patient may have that impact a clinic in providing direct, indirect or non-patient care in satisfying that particular patient. In a dialysis treatment embodiment, information 324 may relate to the length of treatment, type of medicines used, etc. Hence, the treatment data 324 relates to or provides an employee with the necessary information required to set up and treat the patient during a visit.

The patient profile also includes scheduling information 326, which relates generally to when the patient visits the clinic and the length of time the patient stays during a visit as well as other patient preferences and restrictions. The information 326 may relate to the number of days a week a patient visits the clinic or possibly, the particular days, e.g., Monday, Wednesday and Friday versus Tuesday and Thursday. The scheduling information 326 may also include information such as whether the patient needs to be scheduled at a particular time, e.g., mornings or afternoons, whether the patient needs extra time during set up and/or following a treatment. Hence, the scheduling information alone or in combination with the treatment data provides the health provider with the necessary information required to allocate clinic resources and employee time during the patient's visit, e.g., while the patient is being treated or is otherwise requiring care.

Patient information section 314 also includes other profiles, such as profiles 328 and 330. Profile 328 relates to information for a different patient than the patient associated with profile 320. Profile 328 has its own personal data section 332, treatment data section 336 and schedule data section 338. Such information sections 332, 336 and 338 are similar to the section 322, 324 and 326 in that each includes the same type of information, respectively, but however, the information for profile 328 is specific to a different patient and therefore, most likely different in content as well.

Profile 330 relates to the last patient profile in the patient information section 314, i.e., "Patient N" wherein the N relates to the number of patients having stored profiles in the memory 306. In some situations, the number of patient profiles may be quite low, e.g., two or three, and in other situations, the number may be higher, e.g., a hundred or more. Moreover, since the store 306 may also store information related to patients that are not necessarily being serviced by the clinic, e.g., deceased patients or temporary patients, the number of profiles may be even higher. Regardless, the profile 330 has a personal data section 334, a treatment data section 340 and a schedule data section 342. If the patient is deceased or temporary, the schedule information section 342 may reflect this information.

With respect to the employee information 316, in an embodiment, the information is divided into records or profiles wherein each employee that works at the clinic has a profile. An example profile is illustrated as 344 for "Employee 1". The profile 344 includes information related to the employee, such as personal information 346, e.g., name, address, sex, birth date, etc., as well as other information such as patient care capability data 348 and scheduling information 350. Patient care capability data 348 relates generally to the employee's ability to handle direct patient care situations. However, in other embodiments, this information 348 may further include indirect patient care capabilities, such as setting up a machine or taking a machine down, in order to provide the system the ability to monitor the efficiency of an employee with respect to patient care. In a dialysis treatment embodiment for example, information 348 relating to direct and/or indirect patient care may relate to whether the employee is fully trained or in training, whether the employee is handicapped and is therefore limited in some way of providing direct patient care, etc. If the employee is fully trained and is not limited for any reason from providing direct patient care, then section 348 may so reflect. However, if the employee is limited for some reason, then section 348 may likewise reflect such a situation. This information is generally used for scheduling efficiency, i.e., the efficiency of the employees with respect to patient care and an hours per treatment calculation.

The employee profile 344 also includes schedule data 350, which may relate to an employee's work schedule, listing the days and times that the employee is scheduled to be at the clinic. However, the data 350 may also include other scheduling information, such as the various tasks that may be performed by the employee, thereby potentially reducing the number of working hours that the employee can devote to direct patient care duties. Hence, the scheduling information alone or in combination with the patient care capability data 348 provides the health provider with the necessary information required to determine an employee's availability and capability while an employee is scheduled to work.

Although not shown, the employee profile 344 may further include information related to activities performed by the employee relating to non-patient care. This type of information may be important in evaluating the overall staff efficiency of an employee and/or a facility. Non-patient care activities may include administrative duties, facility maintenance duties, etc.

Employee information section 316 also includes other employee profiles, such as profiles 352 and 360. Profile 352 relates to information for "Employee 2", i.e., a different employee from the one associated with profile 344. Profile 352 has its own personal data section 354, patient care capability data section 356 and schedule data section 358. Such information sections 354, 356 and 358 are similar to the section 346, 348 and 350 in that each includes the same type of information, respectively, but however, the information for profile 354 is specific to a different employee and therefore, most likely different in content as well. In an embodiment, the employee profile information may include title information, such as nurse, attendant, staff, etc. Many different titles may be used, i.e., the actual titles used may be relatively arbitrary, but once set, the titles can be used by the system to sort and select appropriate employees when scheduling such employees. For example, when the system needs to schedule a nurse, the profiles having the title nurse located with the patient care capability data may be displayed such that the user can easily choose from the available nurses.

Profile 360 relates to the last employee profile in the employee information section 316, i.e., "Employee Y" wherein the Y relates to the number of employees having stored profiles in the memory 306, typically relating to the number of employees that work in the clinic or at least the number of employees that may provide direct patient care to patients. Profile 360 comprises a personal data section 362, a patient care capability data section 364 and a schedule data section 366, each of which is similar to the corresponding sections described above with respect to profiles 344 and 352, but having information specific to Employee Y.

Memory store 306 also has a resource information section 318, which stores information related to the various resources available, i.e., the facility limitations. These resources may need to be calculated into any scheduling efforts as some resources are limited in that these resources may, in some circumstances, only be used by one patient or employee at a time. For instance, in the dialysis clinic example, the resource information section 318 may relate to the various dialysis machines that can be used at the clinic. Only one patient at a time can typically use these machines at a time. Therefore, when scheduling patients, the availability of these resources should be taken into account.

The memory store 306 may also have other information 368 relating to clinic specific information, such as the store hours, location, etc. The other information section 368 is shown to also indicate that the store 306 may be used to store other information used in scheduling employees and patients that is not explicitly described above.

Furthermore, the store 306 stores driver information 376. Driver information 376 relates to predetermined driver values that are calculated by the user and stored in store 306 for use in optimizing patient and/or employee schedules. One particular driver that may be stored as part of information 376 relates to the desired ratio of employees with different skill sets. For example, in a particular embodiment, the ratio may relate to the number of nurses (RNs) to "non-nurses" (non-RNs), i.e., those employees that are not registered nurses. Many reasons exist as to why a particular company or clinic may decide that such a ratio is desired for their particular business needs, and no particular ratio is claimed herein as better than another, i.e., one business may want more nurses to provide better patient care while another business may decide that fewer nurses are needed to provide adequate patient care. Yet once a company decides that it wants a particular ratio, e.g., one nurse to every three non-nurses or 1:3, the ratio may be stored as a driver 376 in a percentage format. Consequently, when the system 302 is optimizing the employee schedule, it can account for this predetermined business rule and not schedule more than three non-nurses for every scheduled nurse.

Other drivers may also be calculated, stored and used by the system. For instance, a driver may relate to the percentage of scheduled time that a nurse (or other staff member) may be required to perform direct patient care activities over other, non-direct patient care activities. In one example, the nurses may be required to provide 90% of their time to direct patient care activities while non-nurses may be required to only provide 80% of their time to direct patient care activities. These values may be predetermined based on evaluating the needs of the employees to do their jobs effectively while accounting for some acceptable "cushion" should additional patient care requirements occur unexpectedly.

For instance, another driver that may be stored in driver information 376 relates to intermittent acuity. Intermittent acuity is defined as the amount of time needed to address unknown or unplanned patient treatment requirements that arise without prior knowledge or warning. In essence, in any healthcare facility, unexpected events, needs, requirements, etc. occur. Over time, a business can forecast the degree to which such events occur with some specificity. Consequently, in order to account for these events, a driver may be set, and used by the optimization module to allow for these types of events. In one embodiment, the value related to intermittent acuity is a percentage, such as 20%, meaning that additional time requirements are designated for unknown or unplanned direct patient care activities. These additional time requirements are added to the known patient care requirements even though the exact reason for the increased treatment activity is unspecified at the time the patient schedule is developed. Regarding future patient scheduling the specific patient care requirements needed for intermittent acuity factors can be estimated by the facility based on historical patient care data.

In operation, the scheduling module 310 schedules patients on a daily, weekly, bi-weekly or other time schedule. The scheduling module 310, using the memory access module 304, accesses the profile for the patient to determine the days and times for treatment, taking into account available resources from resource information section 318. The scheduling module 310 may also use employee information 316 but typically the employees are scheduled at a later time based on patient care needs. The scheduling module 310 stores the information into a calendar-type schedule (not shown) which may or may not be stored in memory store 306. When the patient information section 314 changes, e.g., by adding, modifying or deleting a patient profile, the scheduling module 310 may automatically update the schedule based on the new information. Furthermore, when the resource information 318 or other information 368 changes, e.g., by adding or removing a machine or by changing the operating hours for the clinic, then the scheduling module 310 may automatically update the schedule based on this new information as well.

In an embodiment, the scheduling module 310 may only modify or update the schedule for "today only" such that all future days are not affected and no past days are affected. Such an embodiment may be useful in cases wherein a change is only temporary and no future days should reflect this change. However, in another embodiment, the module 310 modifies the schedule from "today going forward" and thus updates "today" as well as all future days. This embodiment may be helpful when the changes are permanent but when the past days information is used for archival purposes and thus should not be modified. Thus, in this embodiment, past days are not affected, and in order to modify past days, the user must explicitly edit those days. Of course, in yet another embodiment all days may be automatically updated.

In an embodiment of the employee scheduling functionality, users can carry forward daily or weekly staff modeling or staff schedules once they are developed. As a result, a previous model may be saved and later used or applied, again and again, to other future days. Also, users can rotate the carry forward of these schedules for up to four week intervals.

In accordance with certain aspects of the present invention, once the patients are scheduled, then job-types may be scheduled. That is, the user may enter the type of job that should be scheduled for a particular day, e.g., a certified nurse job-type. The job-type provides an indication to the user that once a certified nurse is scheduled then a predetermined number of direct patient care tasks may be satisfied by that job-type. As discussed in more detail below an embodiment of the present invention automatically calculates the employee job types for an ideal schedule. Importantly, the system will create a need-based, ideal employee schedule using job types. The system then applies acceptable shift length principles to provide an ideal staff model.

Consequently, once the job-types have been scheduled based on the ideal staff model, then the actual employee may be scheduled to fill the shift of the particular job-type. The employee profiles, in this embodiment, provide an indication as to what job-types the employee is qualified to perform. Therefore, in scheduling an employee for a shift of a predetermined job-type, the system may generate a list of capable employees, which further simplifies the process.

Scheduling the employees may also relate to evaluating the employee profiles to determine which days the employees are typically scheduled and adding them to the schedule. The schedule for employees is the same as the schedule for the patients, i.e., the schedule includes information for the both the patients and the employees. A user of the system may perform the task of adding employees to a schedule, one employee at a time, or the scheduling module 310 may automatically evaluate each profile and schedule the employees based on the profiles. Typically, a user may then review the schedule and add or subtract employees as necessary so that the clinic is operating at a more optimal level based on employee skill mix or achieve other scheduling goals.

To help the user determine relative efficiency for the clinic, the scheduling module 310 performs an efficiency calculation to determine whether the clinic has the proper or optimal staffing based on the patient care needs. That is, the schedule is divided into fifteen-minute intervals and for each interval, the module 310 determines the relative needs for the patients during that time, and compares that number to the number of employees capable of providing direct patient care to satisfy those needs and then displays a result based on this comparison. Thus, a quick review of the schedule, and in particular the results based on the comparison, provides a user the necessary information to determine whether to add or subtract employees as necessary so that the clinic is operating at a more optimal level. Additionally, the scheduling module 310 may also review the information once a day is complete to determine scheduling and staffing efficiency according to many different formulas and equations, as discussed below. In another embodiment, larger clinics may be sub-divided into smaller groups and records may be generated related to these different sub-groups. In fact, the sub-groups may edit and view their information separate from the rest of the clinic. In such a case, the overall clinic efficiency report would relate to a combination of the sub-group calculations.

In an embodiment, the module 302 includes an optimization module 370 that generates an "ideal" patient schedule and/or an "ideal" staff schedule. In this case, with respect to the ideal patient schedule, the definition of ideal relates to a preferred schedule having the patient need requirements evenly distributed over a period of time such that for a given day, for example, the patients are scheduled to require the fewest number of employees to meet all the needs of the patients for that day. In order to achieve this, the optimal patient schedule adds all the needs for a particular day (based on time intervals) and divides by the number of intervals in a particular day. The ideal patient schedule is the schedule that closely resembles the optimal patient schedule taking into account real-life variables such as resource limitations, such as facility hours of operation, and patient limitations or acuity, treatment activities, patient preferences and restrictions such as patient transportation, etc. The ideal patient schedule is based on a predefined set of business rules as applied to the current actual patient treatment data entered by the user. Since patient care can be divided, somewhat, into patient care activities, e.g., setup, takeoff, etc., the goal is to evenly distribute the patient care activities throughout the day so there are no peaks or valleys in patient care treatment requirements. Determining the ideal patient schedule is discussed in more detail below in conjunction with FIG. 30. Once the ideal patient schedule has been determined, the employee schedule may be optimized.

With respect to the employee schedule, the ideal staff schedule is constructed using the drivers 376. The ideal staff schedule is then combined with desired shift length information to create an ideal staff module. In operation, the drivers may be calculated directly from the actual current staff scheduling patterns and staff mix methodologies used by a particular facility. That is, the system stores previous, actual schedule information and thus historical information is available to help calculate the drivers for a particular facility. Alternatively, the user may enter these drivers into the system.

The exemplary operating environment having now been discussed, the remaining part of this description section will be devoted to a description of the operative modules embodying the invention and screen shots relating to a particular embodiment of the invention. The logical operations of the various embodiments of the present invention are implemented (1) as a sequence of computer implemented steps or program modules running on a computing system and/or (2) as interconnected hardware or logic modules within the computing system. The implementation is a matter of choice dependent on the performance requirements of the computing system implementing the invention. Accordingly, the logical operations making up the embodiments of the present invention described herein are referred to alternatively as operations, steps or modules.

Figure 4:
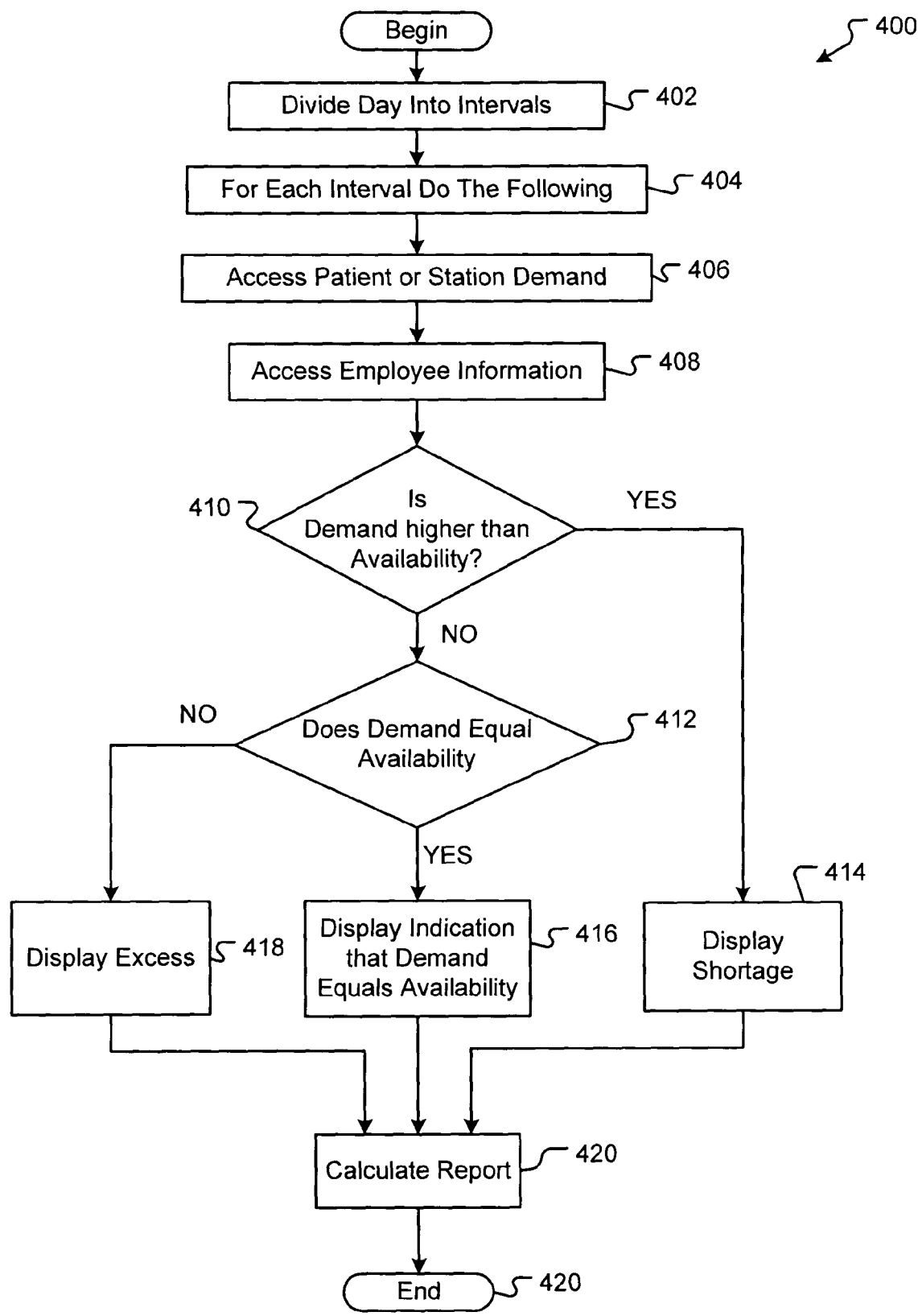
FIG. 4 is a flow diagram illustrating the functional components of scheduling patients and employees according to the present invention.

FIG. 4 is a flow chart of the operational characteristics related to scheduling patients and employees in a health care environment wherein the patients have predetermined needs and employees have predetermined capabilities in tending to the patients in one embodiment of the present invention. Process 400 begins following the entering of the patients and employees into a schedule according to techniques described above. That is, the user of the system enters patient information into profiles and then schedules various patients for each day. Additionally, the user may schedule some employees to work for each day. Once a patient has been entered into the schedule, then the process 400 begins.

Initially, since the schedule is divided by days, each day is further divided into smaller intervals at operation 402. In an embodiment, the interval length is fifteen-minute intervals. Of course, almost any length of time may be used in creating these intervals, but the time should be small enough to provide meaningful information relating to the various activities of a particular day.

Following divide operation 402, the process 400 evaluates various elements on a "per-interval" basis, as indicated by 404. Hence, for each interval, access patient demand operation 406 accesses the demand of the patient(s) that have been scheduled in the particular interval. Determining the patient demands for the interval relates to evaluating the profile for the patient that is scheduled for treatment during that time interval. The profile gives general information, such that the patient may need approximately one hour and thirty minutes of attention over a four-hour treatment time. However, if the patient treatment time falls within the given interval, then it may be determined that the patient needs the full attention of an employee during that interval. In this example, the needs of that patient, although only one hour and thirty minutes worth, may be deemed to require attention during a full four-hour period, i.e., four hours worth of employee attention.

However, in an alternative embodiment, it may be determined that the patient needs the attention of 37.5% of an employee over the course of the four-hour period, for a total of one hour and thirty minutes. In this embodiment, the needs for the patient are given a value of 0.375 or three-eighths during the interval (and all other intervals spanning the four-hour period.) In yet another embodiment, since treatment activities are typically not uniform over the four-hour period, the actual percentages may not vary over the entire treatment. Instead, the time may be broken down into smaller units. For instance, the requirements are typically greater at the beginning and at the end and vary up and down throughout the treatment period. It is these variations that allow the employee to manage their workflow so they can multi-task between different patient treatment activities such that in scheduling, an average value may be used. By only determining that the needs are 0.375, the overall value is more accurate, and the employee scheduling may be more optimal. Obviously, a person cannot be in two places at one time, but in certain situations, the employee can evaluate the requisite needs of the various patients and attend to them one after another.

In the case where the employee tasks are relatively fixed in time, such that the employee does not have discretion as to when the task must be performed, e.g., setting up a dialysis station for use by a patient at a particular time, then the schedule may reflect this situation as a value of one during that time interval. As shown in operation 406, station demands, such as setting-up, taking-down, disinfecting, etc. may also be determined at operation 406. Thus operation 406 generally determines the number of employees that need to be staffed during a particular interval—taking into account that some tasks may be spread over more than one interval by assigning fractional values. Adding the various fractional and whole values provides an overall number of employees needed. A rounding step at the end may be necessary in this case to round up any partial number to make sure enough employees are scheduled. For example, if it is determined that during an interval, 2.5 employees are required to perform the tasks of the interval, then the value is rounded up to three, as it actually takes three people to perform the work of 2.5 people. In an embodiment, this determination is displayed on an output device.

Upon determining the various needs of the patients and stations, access employee information operation 408 determines the currently staffed employee capabilities for each interval. As was the case with the task determination 406, employee information may relate to partial values, wherein an employee is counted at a value less than one for some reason, such as the fact the employee is in training, handicapped, or otherwise assigned to other duties during the day. The employee profiles provide the necessary information for each employee. Alternatively, when the employee is scheduled, the employee may be assigned various tasks, such as direct patient care or some other tasks. Once assigned, the method determines whether the employee is capable of performing the tasks (by checking the employee profile) and then provides a message if the employee cannot perform the tasks or otherwise provides a reduced value if the employee can only perform the tasks at a less than full value. These whole or partial values are added to determine an overall number of available and capable employees during each interval. Again a rounding step is performed at the end. The value may be rounded up or down. Rounding up may be preferred in some cases since the rounded value provides an indication as to the total number of people working. However, in other embodiments, rounding down may be preferred so as not to provide a false indication of the number of available employees during an interval. In an embodiment, the rounded-down value is displayed on an output device.

Following the access employee information operation 408, determination act 410 determines whether, for each interval, the demand is higher than the employee availability. Determination act 410 may determine whether the demand is higher by simply subtracting one from the other or otherwise comparing to the two summed values. In making the comparison, determination act 410 uses the actual summed values relating to the demands and the employee availability, as compared to the round numbers. Thus, determination act 410 may determine that, for a particular interval, there are too many employees scheduled or too few. The value is rounded to the nearest whole person and displayed.

For instance, if determination act 410 determines that demand is higher than availability, then display operation 414 displays the shortage. In an embodiment if the shortage value indicates a shortage by any partial or whole value, then that value is rounded to the nearest whole value to indicate the relative shortage. For example, if the value indicates a shortage of 0.1 or 0.01 persons, then display 414 operation displays a shortage of one employee. As another example, if the value indicates a shortage of 2.2 or 2.9, then operation 414 displays a shortage of three employees. Thus, any partial shortage rounds up to a whole value shortage for display purposes. In an embodiment of the invention, the actual values may be displayed, leaving it up to the user to determine whether to add the proper number of new employees based on the actual values. These values are displayed for each interval of the day. In an embodiment, the value is displayed in red or some other representative color so as to provide an indication that the number relates to a shortage of employees for that interval.

If, however, determination act 410 determines that demand is not higher than availability, then flow branches NO to determination act 412 which determines if the demand equals the availability. If so, then flow branches YES to display operation 416 which displays a zero or some other indication that the availability and demand are equal. In such a situation, the staffing is considered to be optimal for the clinic during that interval. In an embodiment, the value is displayed in black or some other representative color so as to provide an indication there is no excess or shortage of employees for that interval.

If determination act 412 determines that the demand is not equal to availability, then availability is higher than demand, which indicates an excess in employee availability. In such a case, flow branches NO to display operation 418 which displays such an excess. Again, the actual values are used in determining the excess so that the display may either display the actual values or a rounded version of the excess. Typically, the excess values are rounded down to the nearest whole persons, conservatively indicating the number of additional employees scheduled for a particular interval. In an embodiment, the value is displayed in blue or some other representative color so as to provide an indication that the number relates to an excess of employees for that interval.

In one embodiment, following display operations 414, 416 or 418, calculate report operation 420 determines the relative efficiency for each day. The efficiency calculation generally indicates the relative efficiency of the clinic given the sum values of demand and the sum values of employee availability. Efficiency increases as the two sum values, for demand and availability, converge. That is, when the demand and the availability for the day are equal, then the clinic is operating at 100% efficiency. In alternative embodiments, advanced calculations may be performed to determine efficiency and to calculate and generate various efficiency reports, as described below. Following the calculation of the report, a percentage value may be displayed so the overall efficiency for the day may be viewed while a user performs the task of scheduling patients and staff. Alternative embodiments however, do not calculate or display the efficiency report.

Figure 5:
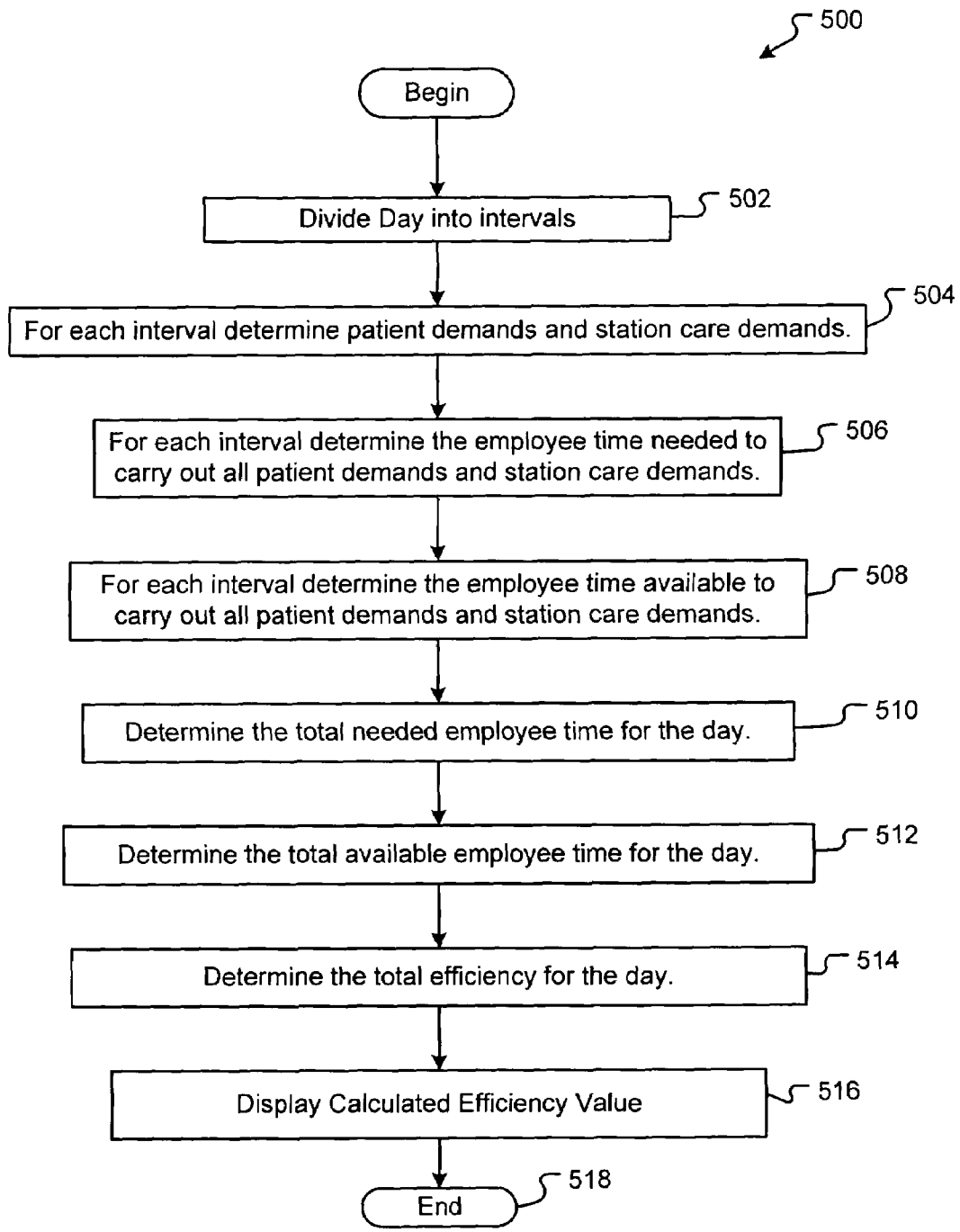
FIG. 5 is a flow diagram illustrating the functional components of determining efficiency in an embodiment of the invention.

In accordance with other aspects of the present invention, the efficiency calculation is relatively complex and relates to various separate calculations. FIG. 5 is a flow chart of the operational characteristics related to determining the efficiency for a particular day having various station and patient demands as well as various employees scheduled for the day. Flow 500 begins as divide operation divides the particular day into numerous intervals, e.g., fifteen-minute intervals. Following divide operation 502, determine operation 504 determines the patient demands and station care demands for each interval. Determine operation 504 is similar to operation 406 shown in FIG. 4 and described above. Upon determining the needs of the patients and the stations, the employee time needed to satisfy these demands may be determined at operation 506.

Following the determination of the needed employee time for each interval, the available employee time for each interval may be determined. The available employee time may be determined from the employee profiles or from the job description as scheduled. Determination operation 510 is similar to access operation 408 described above in that it determines employee availability for each interval. In an embodiment, the number of hours available is decreased by other factors, such as breaks, lunches, etc. These deductions are blended into the average time for an employee in determining efficiency and not into actual availability for patient care since the lunches and breaks may be taken at variable times in the day.

Upon the determining the employee time that is available for a particular day, then determine act 510 determines the total employee time needed for the day in order to satisfy the demands of the patients and the stations. This value may be the summation of the interval values determined at operation 506. Similarly, the next operation, determination operation 512 determines all the total available employee time for the day. This determined value may be the summation of interval values calculated at operation 508.

Using the summation values from operations 510 and 512, determine operation 514 may calculate the efficiency for the day. In an embodiment, the number of needed employee hours is divided by the number of available hours to determine an efficiency value percentage. Other embodiments may perform yet other calculations to determine the overall efficiency.

Once efficiency has been determined, display operation 516 may display the efficiency value. Following display operation 516, flow 500 ends at end operation 518.

FIGS. 6-23 illustrate screen shots from a particular embodiment of the present invention. The screen shots illustrate various aspects in scheduling patients having specific needs and employees, the employees also having specific needs or capabilities. The embodiment shown in FIGS. 6-23 relates to scheduling patients and employees in a health care clinic that provides dialysis treatment to the patients. Although shown and described with respect to health care, and in particular dialysis clinics, the present invention may be utilized in other businesses as well.

Figure 6:
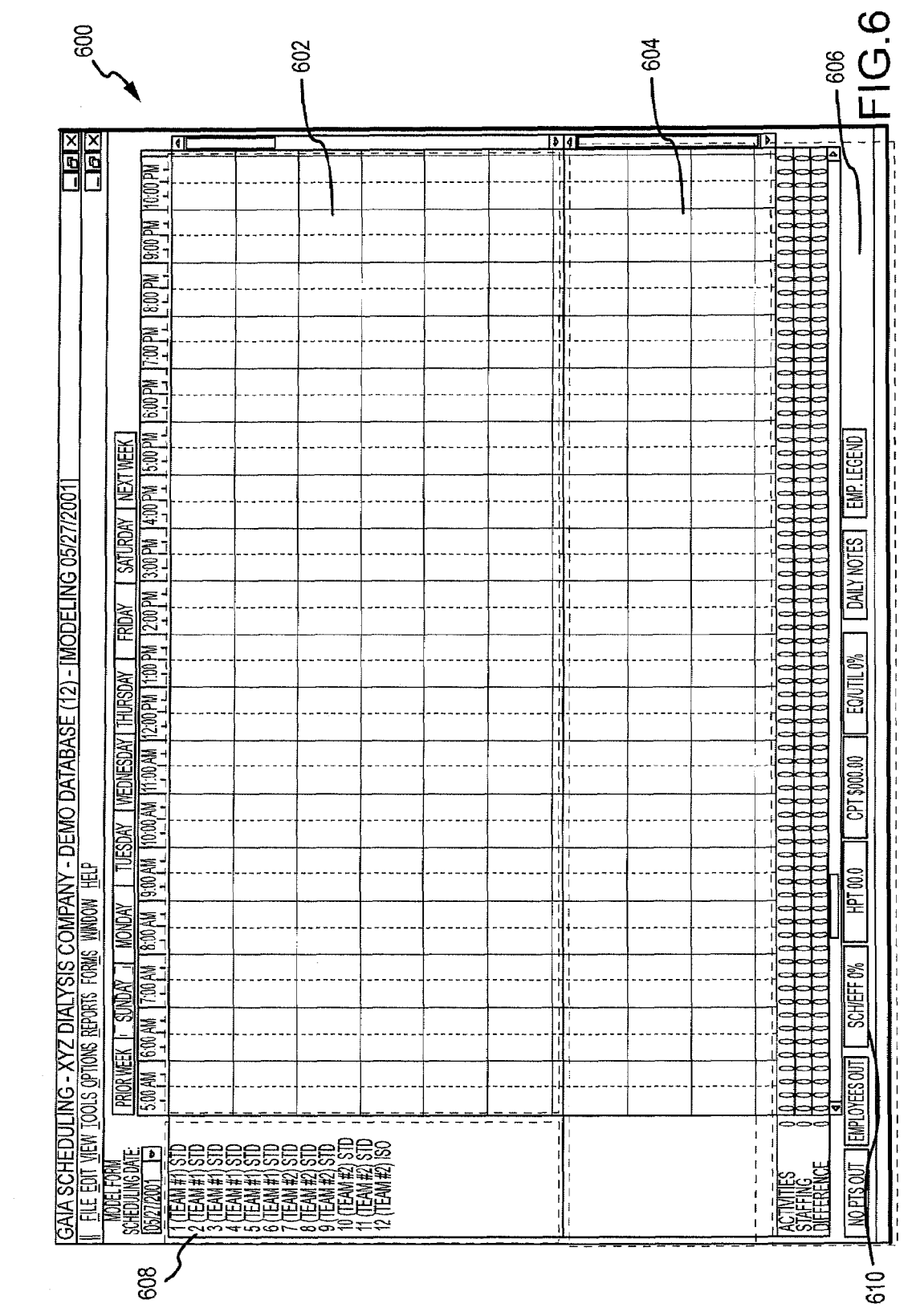

With respect to FIG. 6, the screen shot 600 illustrates the general layout of the graphical user interface for the scheduling system. The system provides a patient scheduling area 602, an employee scheduling area 604, a calculation display area 606, station display 608, among other items. The patient scheduling area 602 provides a visual indication of the patients that are scheduled and for which station. The time values are above the patient scheduling area. As patients are scheduled, the area may also provide an input system to add or modify patient schedules using known drag and drop techniques. Additionally, the area may be used to generate pop-up menus or windows to further modify or update patient schedules. Similarly, the employee scheduling area 604 may also be used to provide input using a mouse or other computer input systems or techniques. The calculation area 608 is generally a display only region and displays various calculations related to demands and availability for each interval. The area 608 may also have an efficiency display 610, which displays the results of an efficiency calculation for the day.

Figure 7:
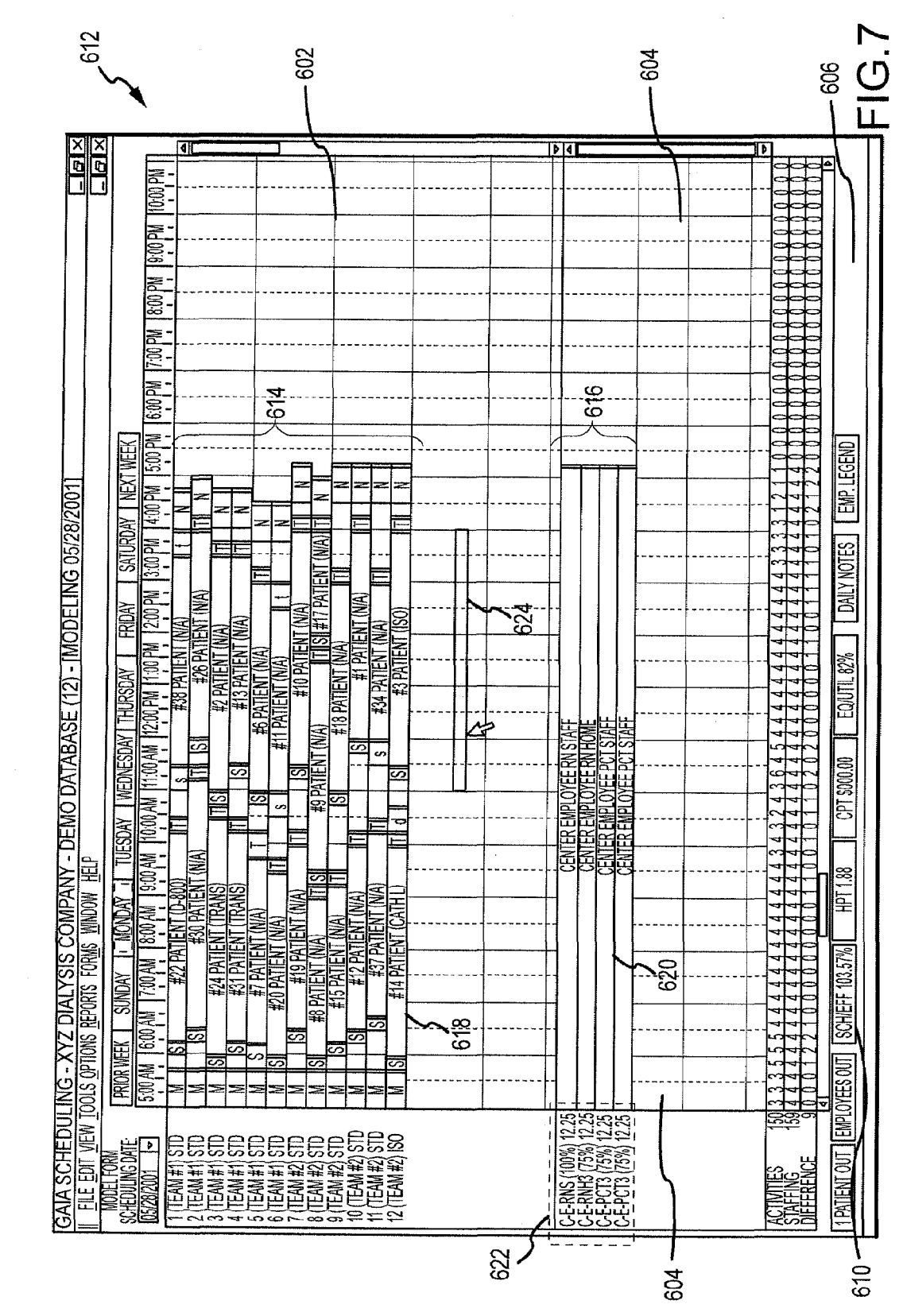

FIG. 7 illustrates screen shot 612 which has the same layout as screen shot 600 shown in FIG. 6 but further includes exemplary patient schedules 614 and employee schedules 616. Each patient schedule portion, such as patient portion 618 relates to the scheduled time for a particular patient. For example, the time scheduled for the patient represented by portion 618 starts at approximately 6:30 AM and concludes at approximately 10:45 AM. The portion 618 may be further broken down into sub-portions, such as the beginning setup portion indicated by the "S" or the ending portions: "takeoff" stage indicated by the "T" or the disinfect stage indicated by the "d". These sub-portions relate to station demands that are not necessarily patient specific or considered patient care. However, these items require employee attention and are therefore scheduled for this reason.

In editing the patient scheduling portion 602, the portions, such as portion 618 may be selected using a mouse or other computer input system. During a drag and drop procedure, a shadow box 624 is displayed to indicate that drag operation is occurring. Additionally, the shadow box maintains the width of the original portion so as to allow the user to quickly determine whether a drop into a new time zone can be achieved without causing a time conflict with another scheduled task or portion. Additionally, the click and drag functionality is programmed to work on all patient and staff portions, such as portions 618 and 620 discussed below. Users can move patients and employees around and instantly view the effects of the changes in the scheduling efficiency calculations. Indeed, in an embodiment, the click and drag functionality is programmed to work in all views, including any combination of patient and staffing modeling views, e.g. actual versus ideal for both patient and staff views, discussed in more detail below.

The employee portion 604 includes several employee schedules 616 as shown in FIG. 7. The employee schedule portions, such as portion 620 may be moved using a drag and drop technique or the portion may be selected and then edited from a menu or pop-up window. Other techniques may also be employed in adding, modifying or updating the portion 620.

The employee portion 604 also has an information section 622 that provides information relating to each employee job type that is scheduled. For example, the information section 622 includes the title of the employee job type and the percentage of time that the employee job type is dedicated or available for direct patient care duties. Importantly, if the employee job type is only partially available, i.e., less than 100%, then this information is displayed in the section 622. In another embodiment, not shown, the actual scheduled employee percentage available for direct patient care may be displayed in portion 620. Additionally, the total hours available for direct patient care may also be displayed, that is, the number of hours the employee is scheduled multiplied by the percentage available. Information section 622 provides a user with a quick reference section to see the percentage of time an employee job type is available for direct patient care. In an embodiment, the information displayed in section 622 relates to job type, e.g., a manager or a trainee, and not necessarily to the specific employee. In other embodiments, the information may relate to the specific employee and his/her limitations.

Figure 8:
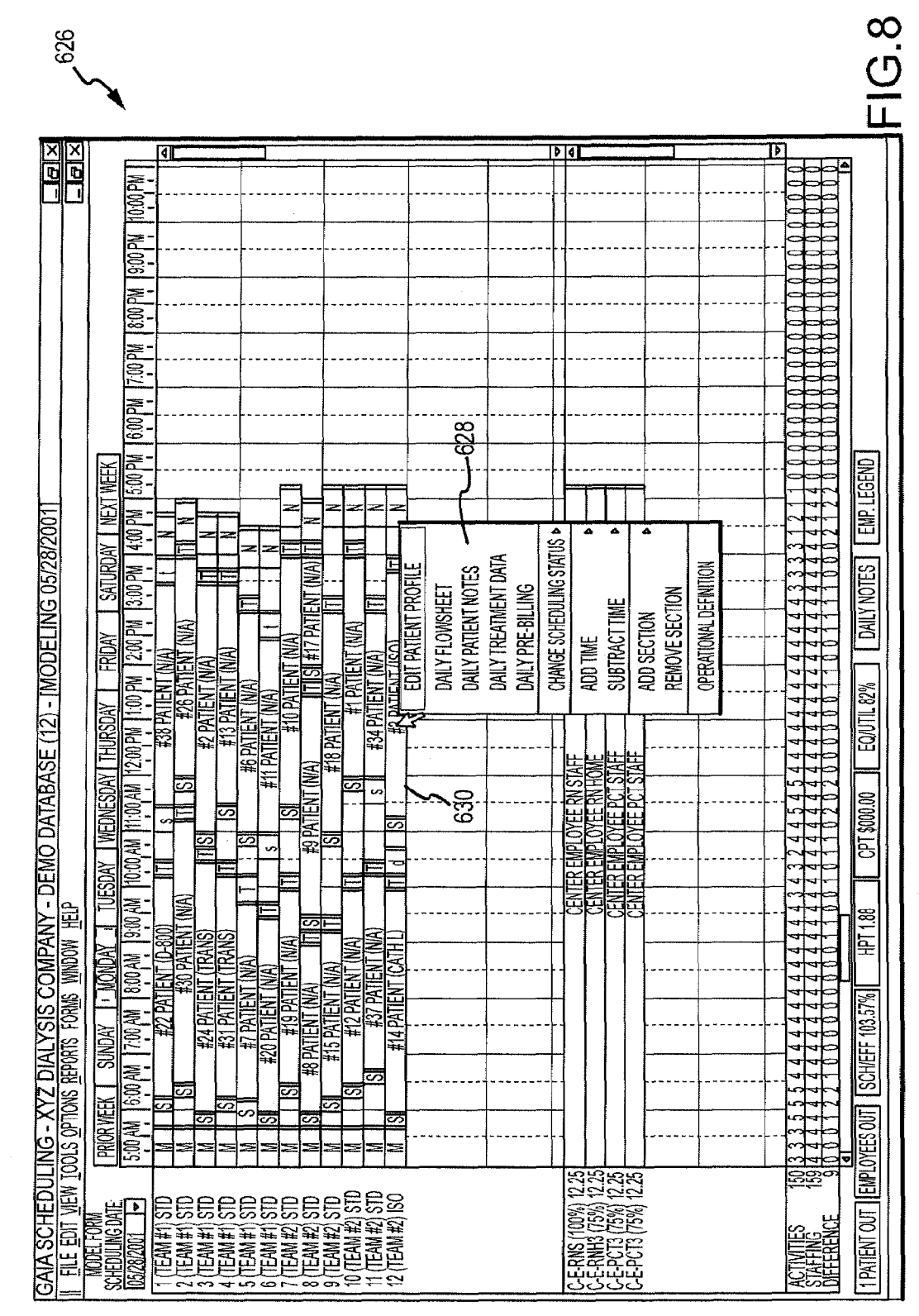

FIG. 8 illustrates a screen shot 626 similar to the screen shot 612 shown in FIG. 7. However, screen shot 626 illustrates a pop-up menu 628 generated by placing the cursor over a patient scheduling portion, such as portion 630 and depressing the right mouse button on the mouse input device. Alternative embodiments may generate the pop-up menu 628 in other ways, such as through the use of a predetermined series of keystrokes. The menu 628 provides a number of options to the user such as adding or subtracting time to the patient appointment portion 630. The menu 628 also provides a means for viewing or editing daily sheets such as a flowsheet, patient notes sheet, treatment data, or pre-billing. The menu 628 may further provide means for adding or removing sections to the appointment or to change the scheduling status. In an embodiment, using the right mouse button to add or remove a section or to increase or decease time in a section will only change that current day's employee portion 620. Permanent changes need to be made in the patient profile. If some of the menu options are not available, then they may be displayed in a "grayed out" manner and selecting them has no effect.

Figure 9:
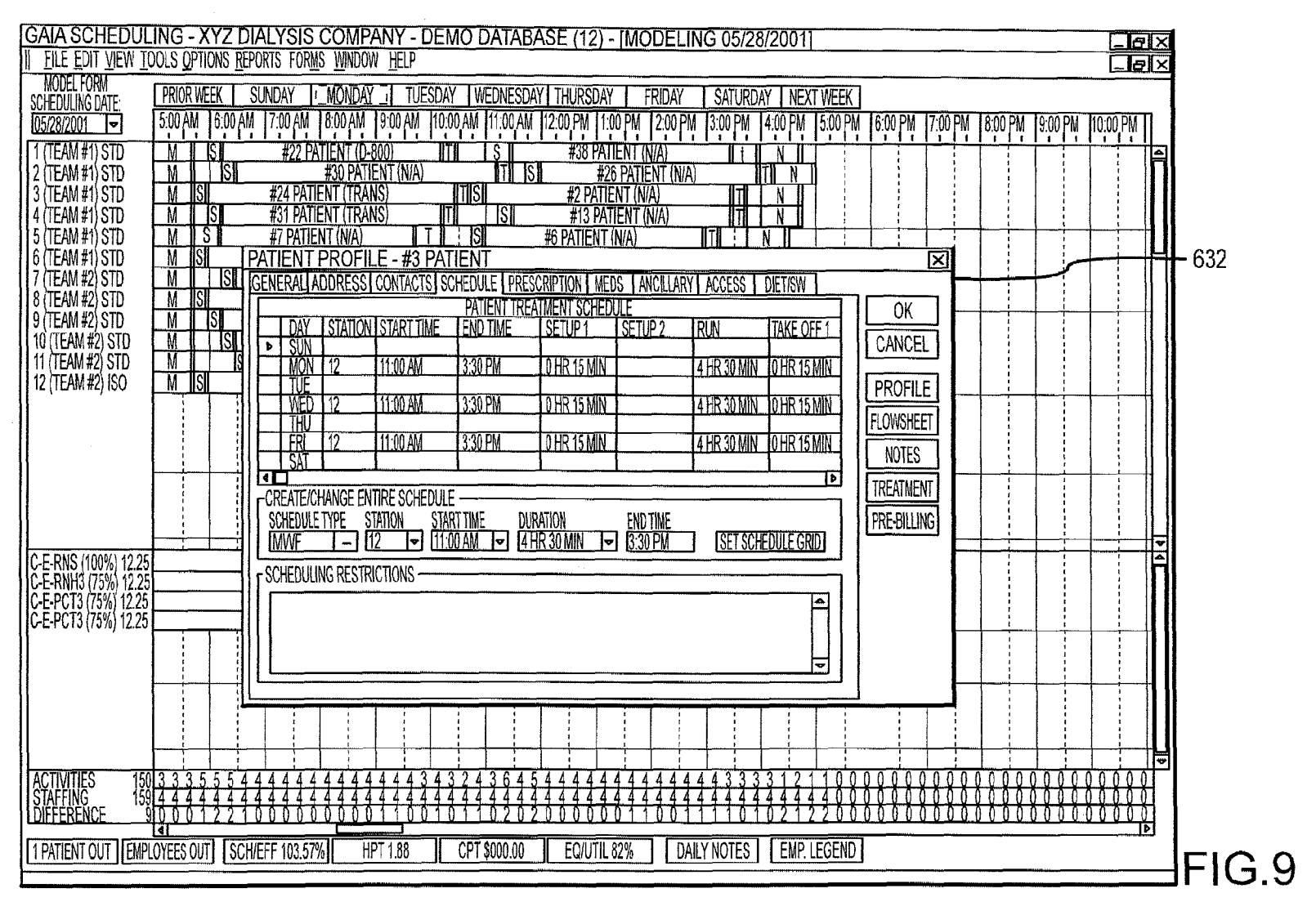

The pop-up menu 628 also provides a method of editing the patient profile for the patient associated with the portion 630. Indeed, one of the menu options is labeled "Edit Patient Profile," and selecting this option generates a pop-up window 632, as shown in FIG. 9. The window provides the user a means of entering and modifying relatively permanent, i.e., not temporary, patient information. The various types of information include personal data, treatment data and scheduling data. Once finished, the user may select the OK button to exit the profile modification window 632.

Figure 10:
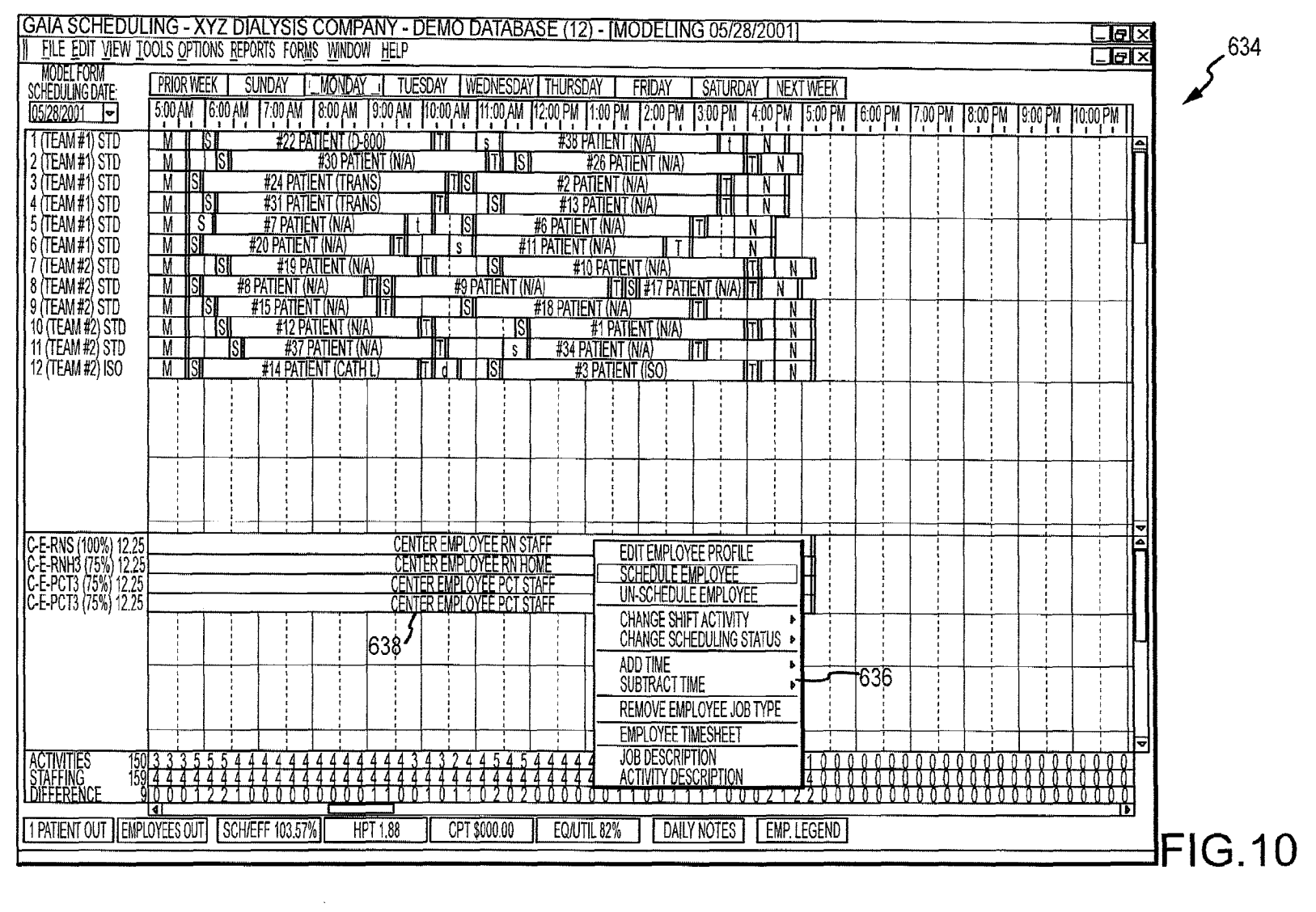

FIG. 10 illustrates a screen shot 634 similar to the screen shot 626 shown in FIG. 8. However, screen shot 634 illustrates a pop-up menu 636 generated by placing the cursor over an employee scheduling portion, such as portion 638 and depressing the right mouse button on the mouse input device. Again, alternative embodiments may generate the pop-up menu 636 in other ways, such as through the use of a predetermined series of keystrokes. The menu 636 provides a number of options to the user such as adding or subtracting time to the employee shift portion 638 or removing the job type completely for the day. The menu 636 also provides a means for changing the shift activities or employee scheduling status.

In an embodiment, the job shift 638 may relate to a job type or title and not necessarily to a particular person. In a particular embodiment, the various job types may be stored and edited from a pop-up window 640 shown in FIG. 11. Each job type provides a percentage related to the amount of direct patient care associated with the particular job type. That is, an employee that is categorized with a particular job type is considered to be available to provide direct patient care to the extent represented by this value.

Since the employee shift 638 may only relate to a generic job type, the menu 636 (FIG. 10) may further provide means for selecting a particular employee to work during the shift 638. Choosing the "Schedule Employee" option from menu 636 generates pop-window 642, shown in FIG. 12. Window 642 illustrates all potential employees that have been characterized as being able to fulfill the requirements of the particular job type associated with the shift 638. Thus the user may simply select one of the employees from the list to schedule the employee wherein the employee's name would be displayed on shift 638.

Once scheduled, the shift portion 630 shown in FIG. 10 then relates to the particular scheduled employee. In such a case, the menu 636 would provide a menu option relating to editing the employee profile for the scheduled employee. Such a profile relates to the characterizations, e.g., job types, that the employee is capable of doing. The profile may also include other information, such as personal data or specific patient care capability data.

Also, once a schedule is finalized under any view it can be copied to other views as daily or permanent changes. An example of this would be if the user makes a selection to view the ideal patient schedule. Accordingly, the user then uses the click and drag functionality to move several patients around to refine the results of the ideal patient scheduling routine. Once the user finalizes the ideal patient scheduling view the user then could copy the ideal patient scheduling results over to the actual patient daily schedule on the model form. In addition, the user could then elect to make these changes permanent changes in the patient profiles by taking the revised actual daily patient schedule and updating each individual patient scheduling profile to reflect today's revised daily patient schedule. This copy functionality would then take the actual patient daily schedule and store them as permanent changes to each individual patient scheduling profile.

Figure 13:
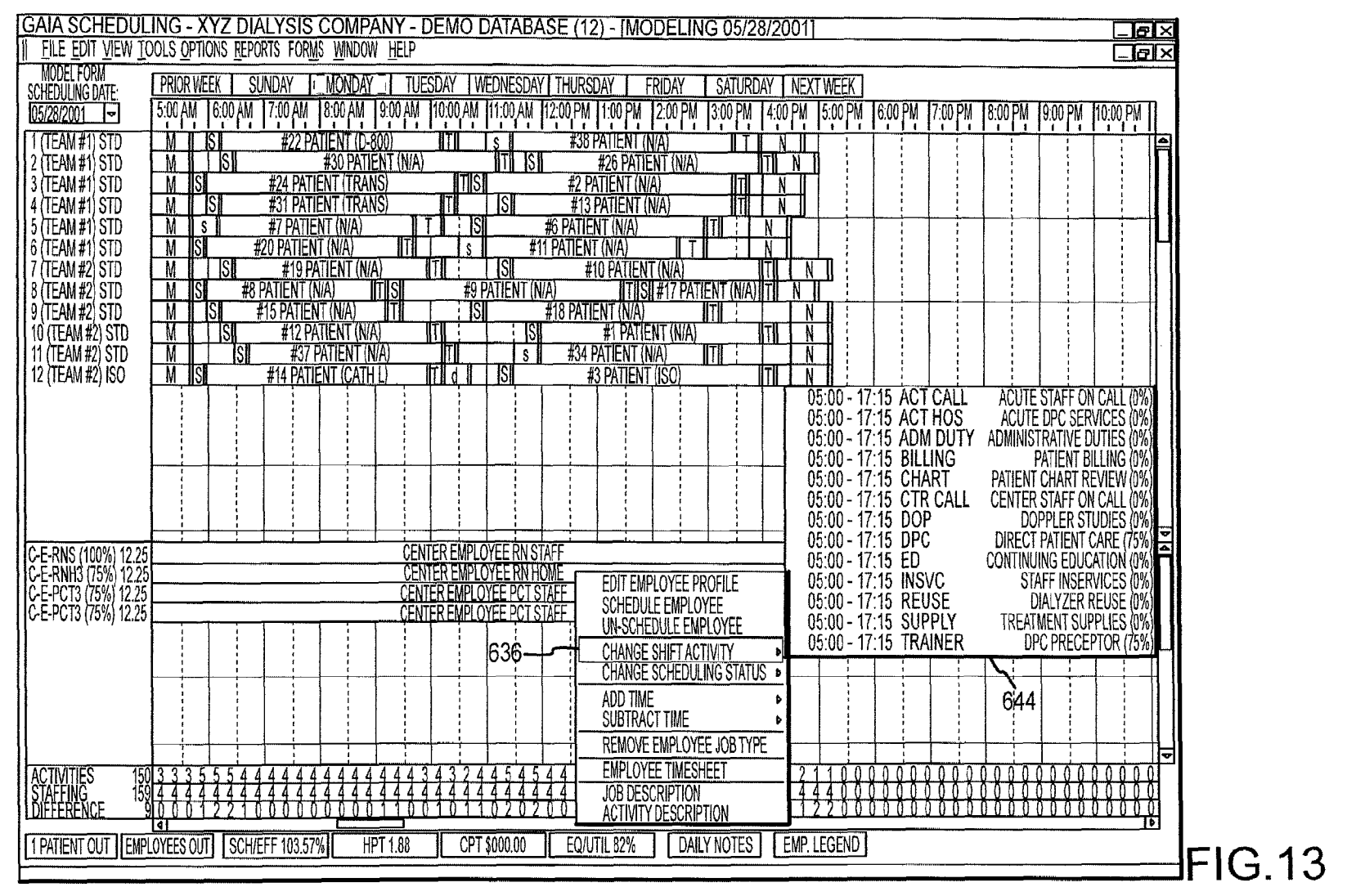

FIG. 13 illustrates yet another option presented by menu 636, i.e., the change shift activity option. Choosing this option generates and displays a cascade menu 644 of various predefined activities that may be assigned to the employee during the shift, wherein each employee is assigned only one such activity for the shift. Each activity has a direct patient care value (in a percentage form) relating to the available direct patient care time the activity provides. Thus, in scheduling employees, the menu 644 provides a quick reference to the amount of direct patient care the employee may provide to patients during his/her shift.

In another embodiment, different activities may be assigned to a shift for different blocks of time. Indeed, the shifts may be sliced in many different ways and activities can then be assigned for each different slice. For example, a particular shift may be assigned to perform direct patient care (at either 100% or at 75%) for the first and last three hours of the shift wherein the middle two hours of the shift are allocated to performing training or some other type of activity. In this case, since the values relating to direct patient care capability at the bottom of the display reflect the activities assigned on a per-interval basis, the efficiency and adequacy of the staffing may be determined in light of the sliced staff schedule portion.

Figure 14:
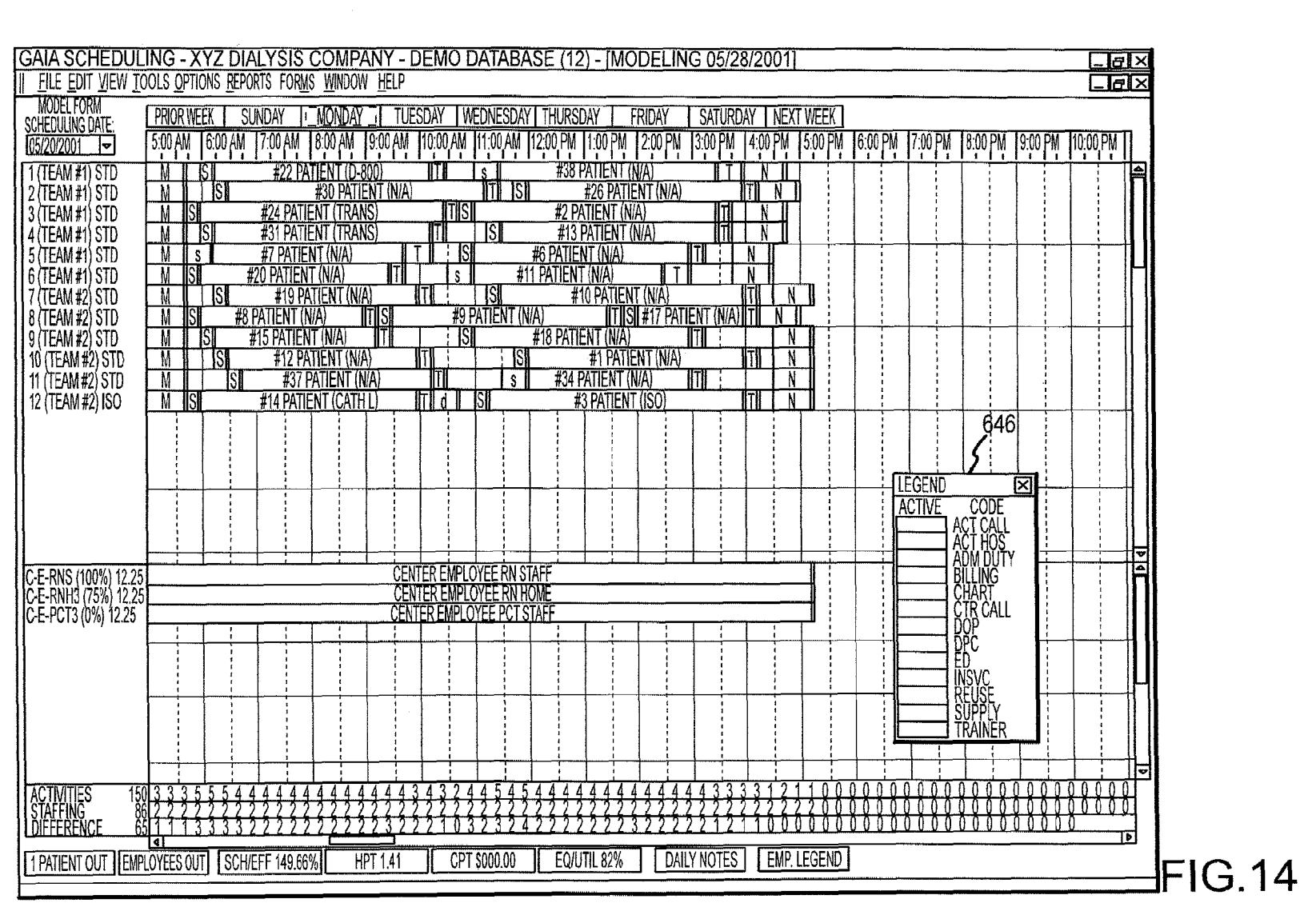

As the activity is modified according to the menu 644 (FIG. 13), the employee shift may be displayed in a new color, indicating the assigned shift activity. The colors may further be defined or edited from a pop-up window 646 as shown in FIG. 14. The colors are primarily to provide a simple and relatively quick reference as to the assigned shift activity for the employee. Other colors and/or other techniques may also be used to provide a quick reference.

Figure 44:
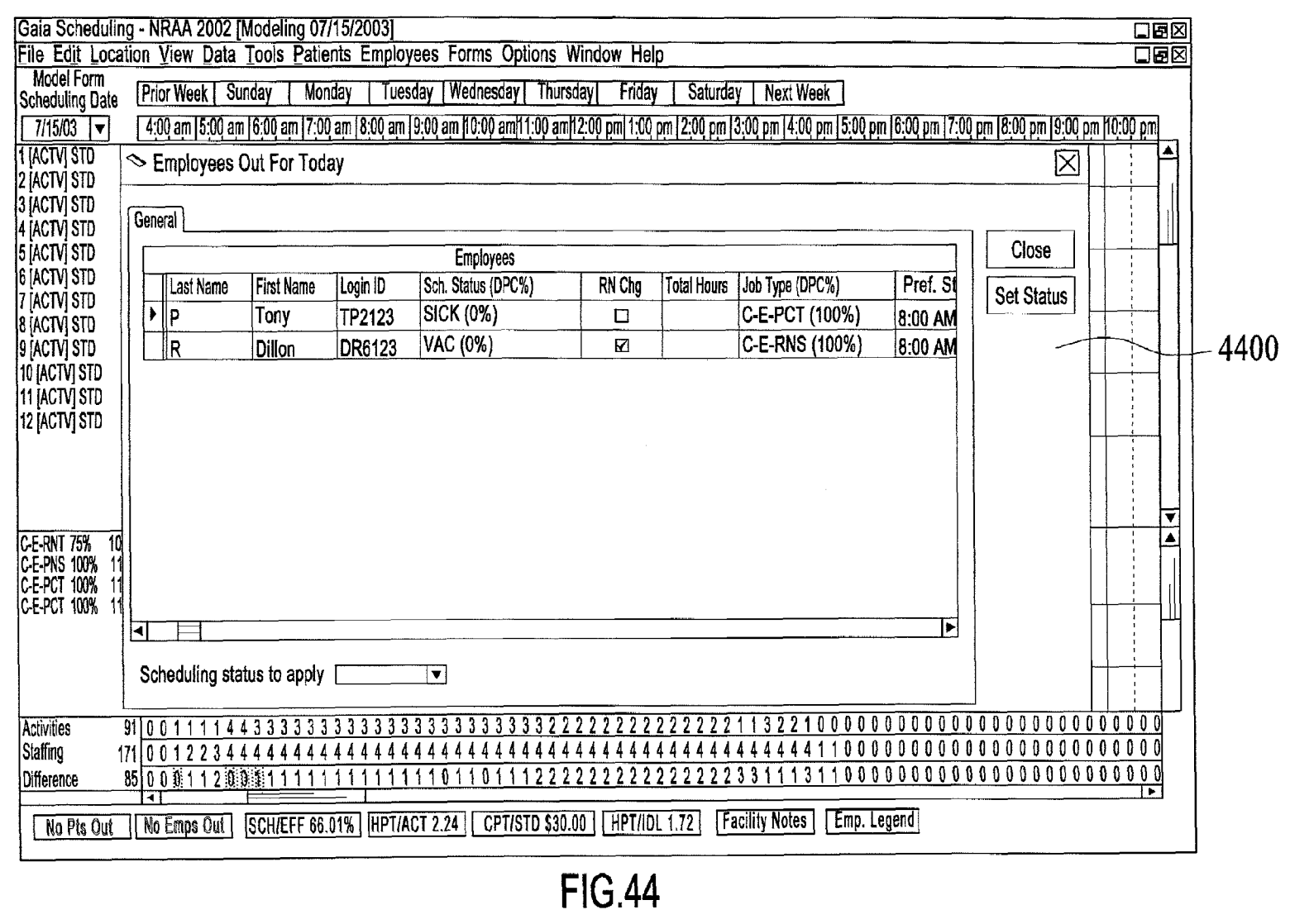
Figure 45:
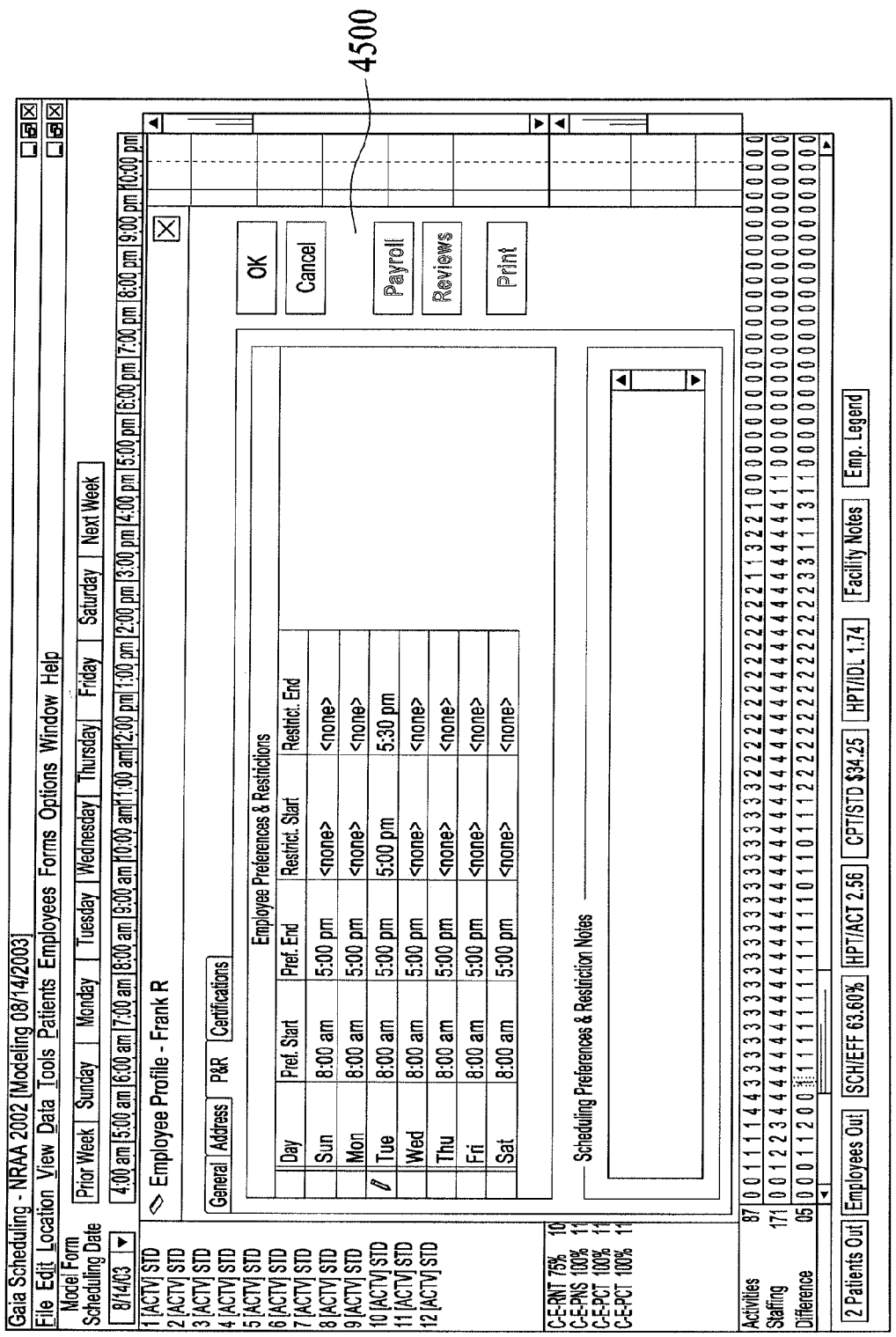
Figure 48:
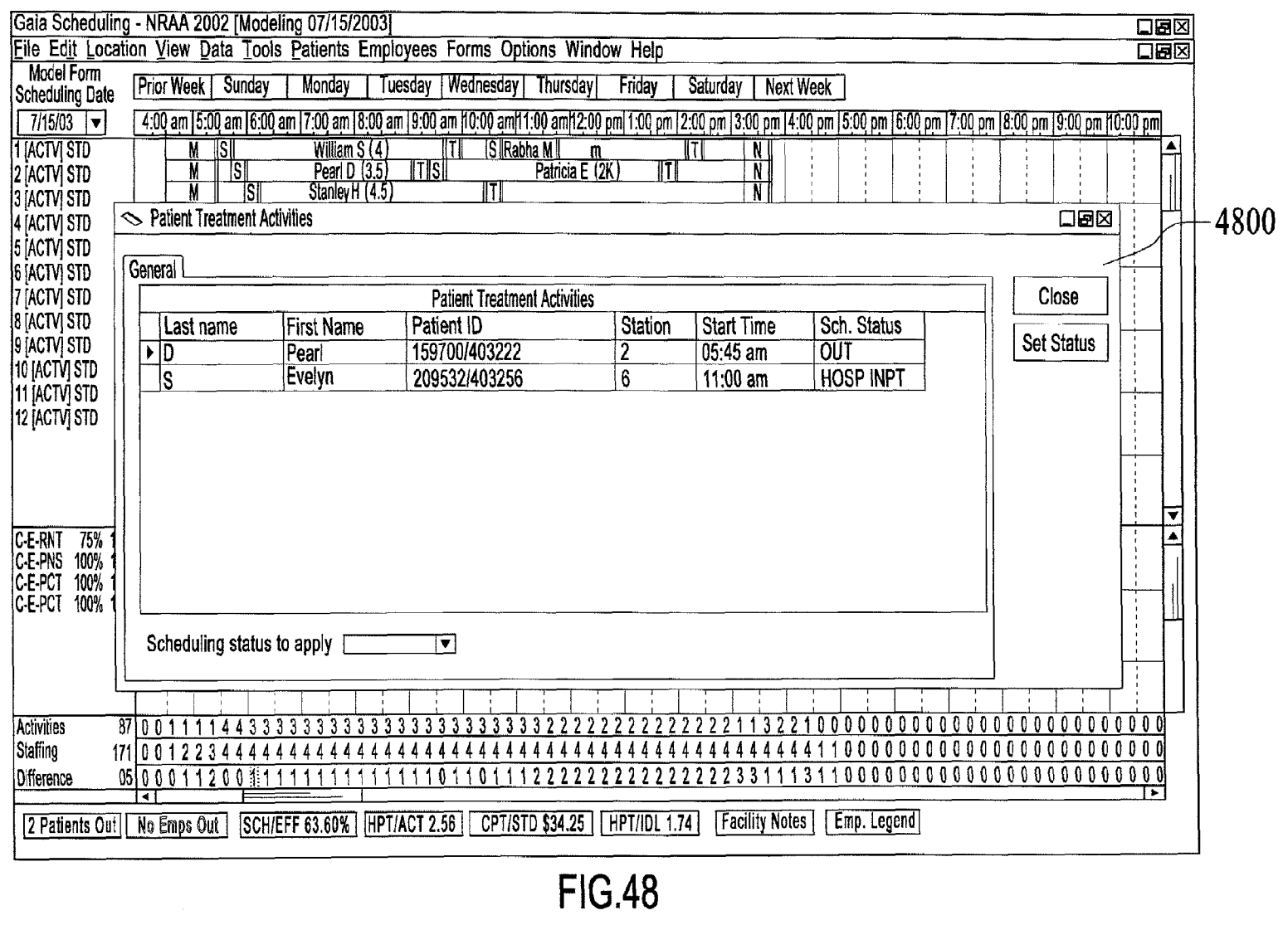
Figure 49:
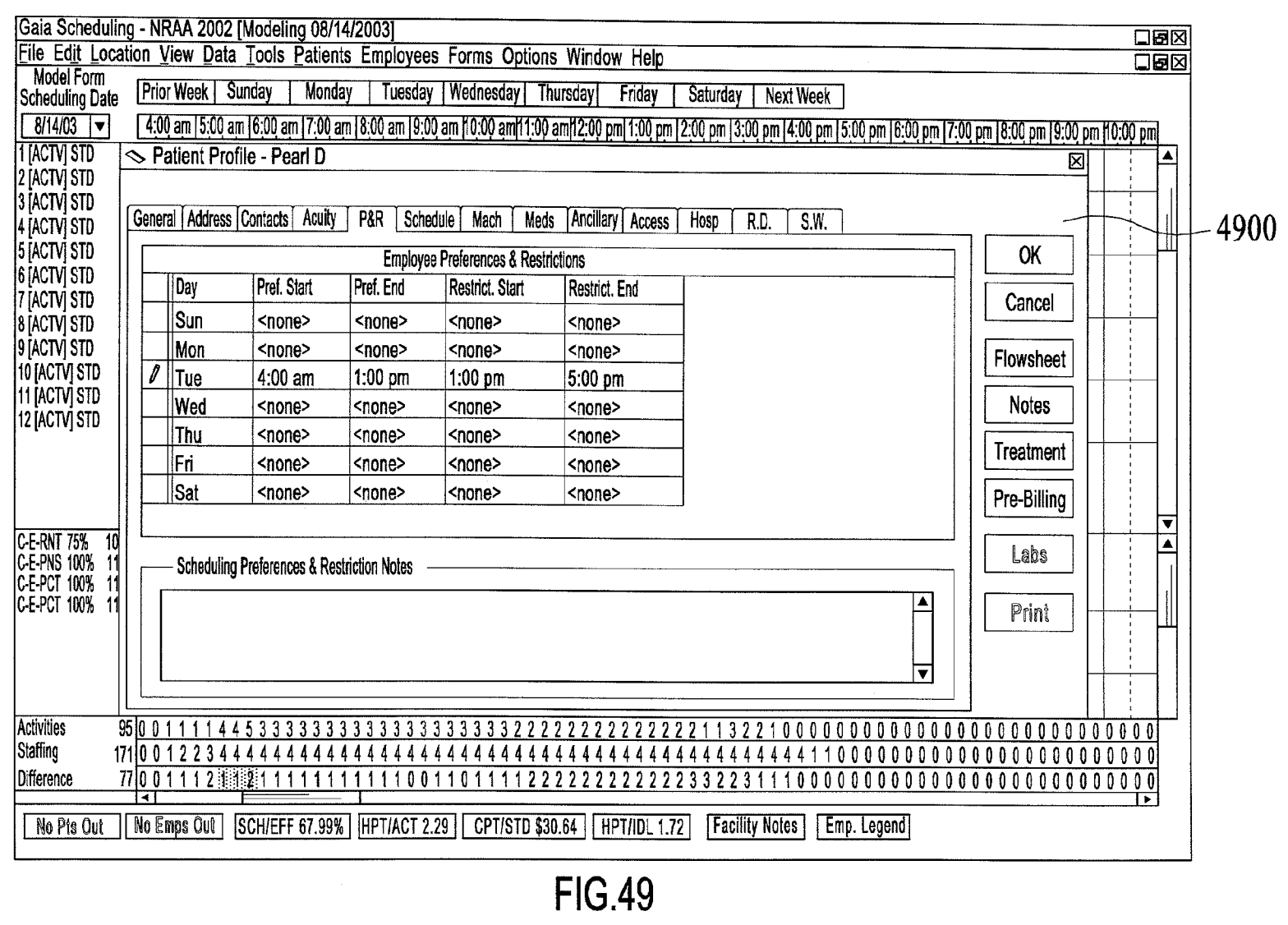
Figure 50:
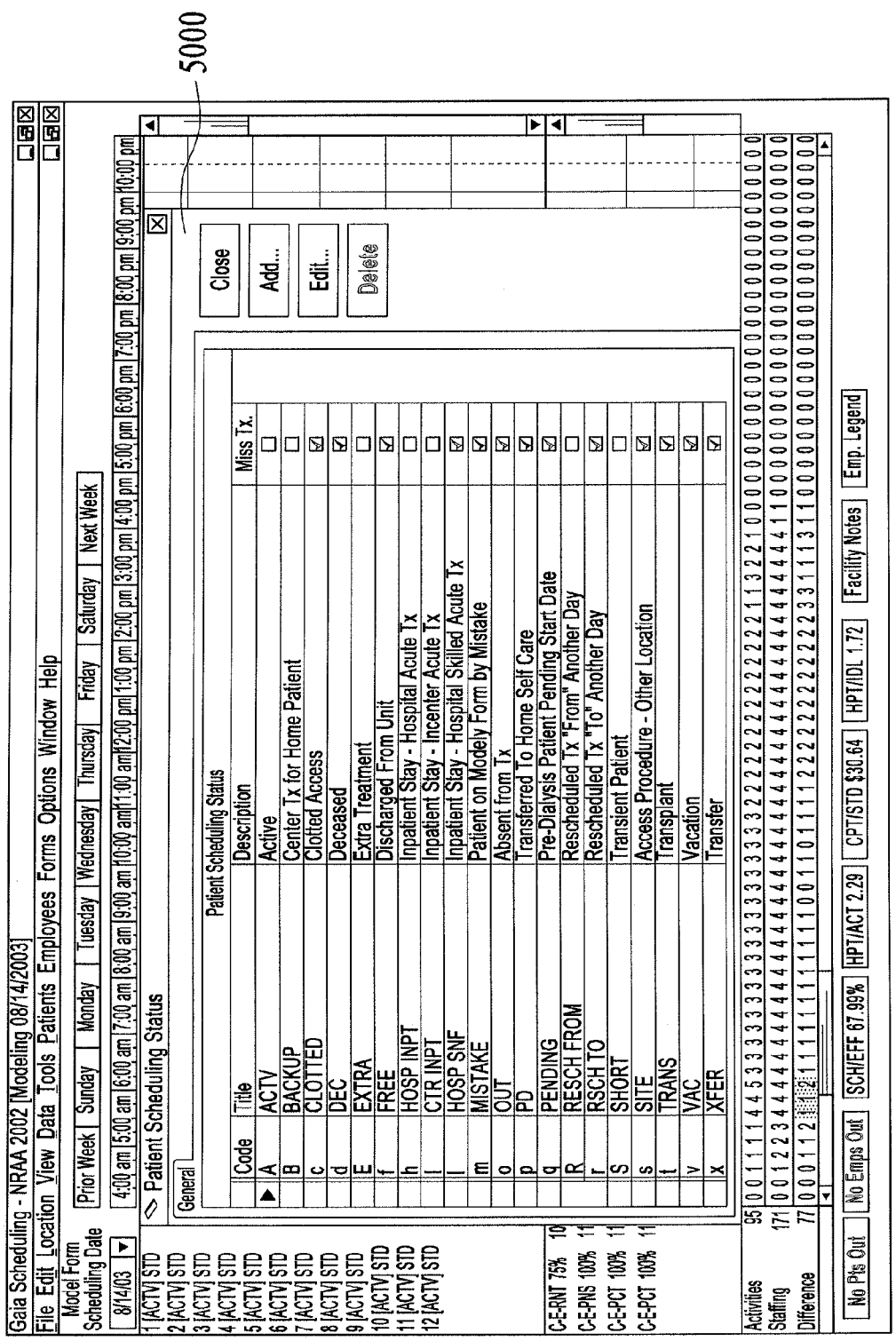

Furthermore, once an employee (or patient for that matter) is scheduled, a user may place the cursor over the employee or patient portion to generate a pop-up menu, wherein one menu option relates to changing either the employee or patient scheduling status. FIG. 6 illustrates an exemplary pop-up menu 628 having such a menu selection for the patient portion 630. Selecting this option provides a list of selections that will remove the patient or employee off the daily model form and put them in the "out bucket" or change their level of contribution towards direct patient care, etc. FIGS. 46 and 50 illustrate exemplary lists 4600 and 5000 for changing the employee status or the patient status, respectively. This process makes the change on a temporary basis. Upon selecting a status indicating that an employee or a patient is out for a particular day, the out list is updated. FIGS. 44 and 48 provide out lists 4400 and 4800 for employees and patients respectively. As an alternative to the temporary changes indicated by lists 4400 and 4800, more permanent changes to patient or employee profiles as discussed below that effectively do the same thing except over longer periods of time. FIGS. 45 and 49 illustrate profile portions 4500 and 4900 for employees and patients, respectively, showing more permanent factors relating to scheduling flexibility. More particularly, profile portions 4500 and 4900 illustrate the preferences and restrictions portion of a particular employee or patient, respectively. These preferences and restrictions portions are evaluated as schedules are made to ensure that a patient's scheduled time complies with such preferences and restrictions, such as when a particular patient prefers to be treated in the morning, or is restricted such that she has to be treated in the morning, etc.

Alternative embodiments may also provide a status property for resources in a similar manner.

Figure 15:
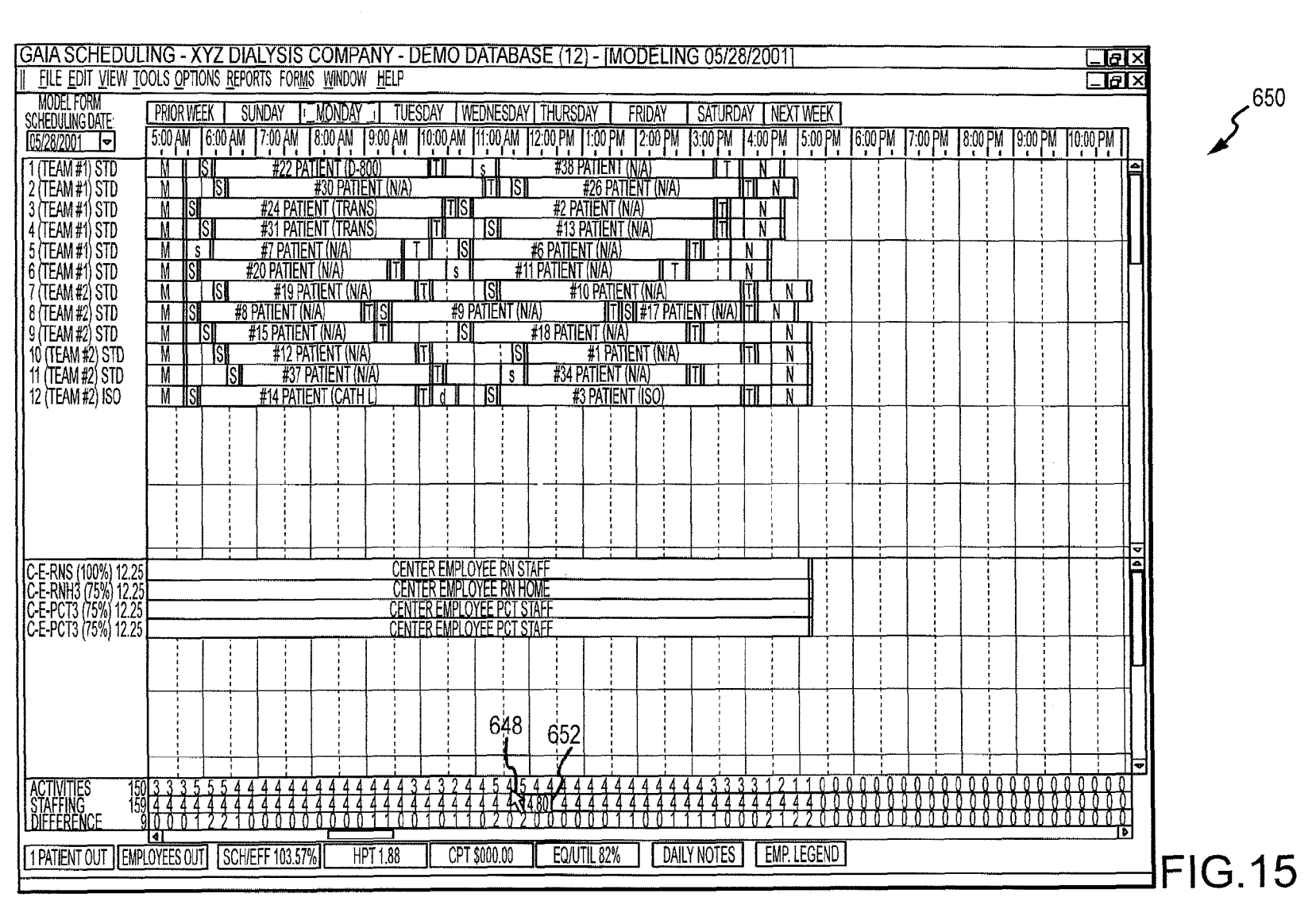

In an embodiment of the invention, when the pointing cursor 648, either controlled by a mouse, trackball or some other input control device, is positioned over an element on the display, such as display 650 shown in FIG. 15, an information box 652 may be displayed. In an alternative embodiment, such display is only provided following a predetermined delay period that the mouse has remained over the element, such as one of the displayed number values. In a particular embodiment, the displayed number values relate to the number of employees required to satisfy the patient needs for each interval, the number of available employees scheduled to satisfy the patient needs for each interval and the difference between the two. As discussed above, the patient needs and the employee availability may be calculated as fractions and thus the actual displayed values are the rounded version of the actual value. However, information box 652 may be configured to display the actual value so the user may readily determine such information.

In another embodiment, the views related to the patient requirements for a particular time interval, such as item 648 may be broken down into time requirements based on job type. That is, in alternative embodiments, the patient activities may be further classified as direct patient care requirements by nurses, or by non-nurses, for example. Although not shown, in such a case, the view 648 may be divided to indicate the different requirements. Also, in other embodiments, the view 648 may display the total requirement but when the mouse hovers over the item, the pop-up display may indicate the broken-down values for the requirement. In yet another embodiment, the staffing values in display area 606 may also be broken down in this manner. Further, users may access this broken down information under the view menu, in an embodiment, to therefore view only the patient treatment time requirements for RN staff or Non-RN staff. This will allow the user to make sure the facility has enough RN coverage as well as Non-RN coverage on a grouping by grouping basis.

Figure 16:
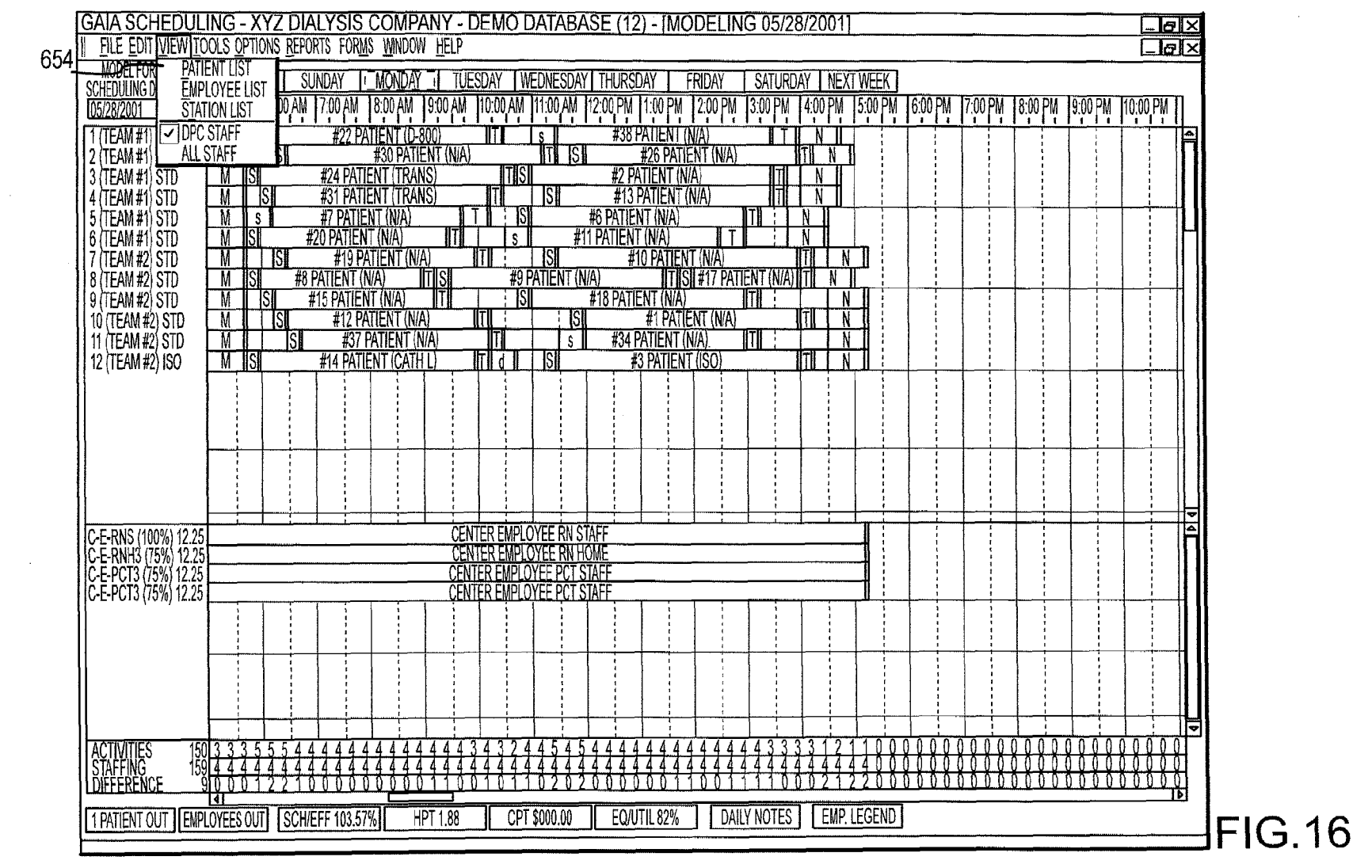
Figure 17:
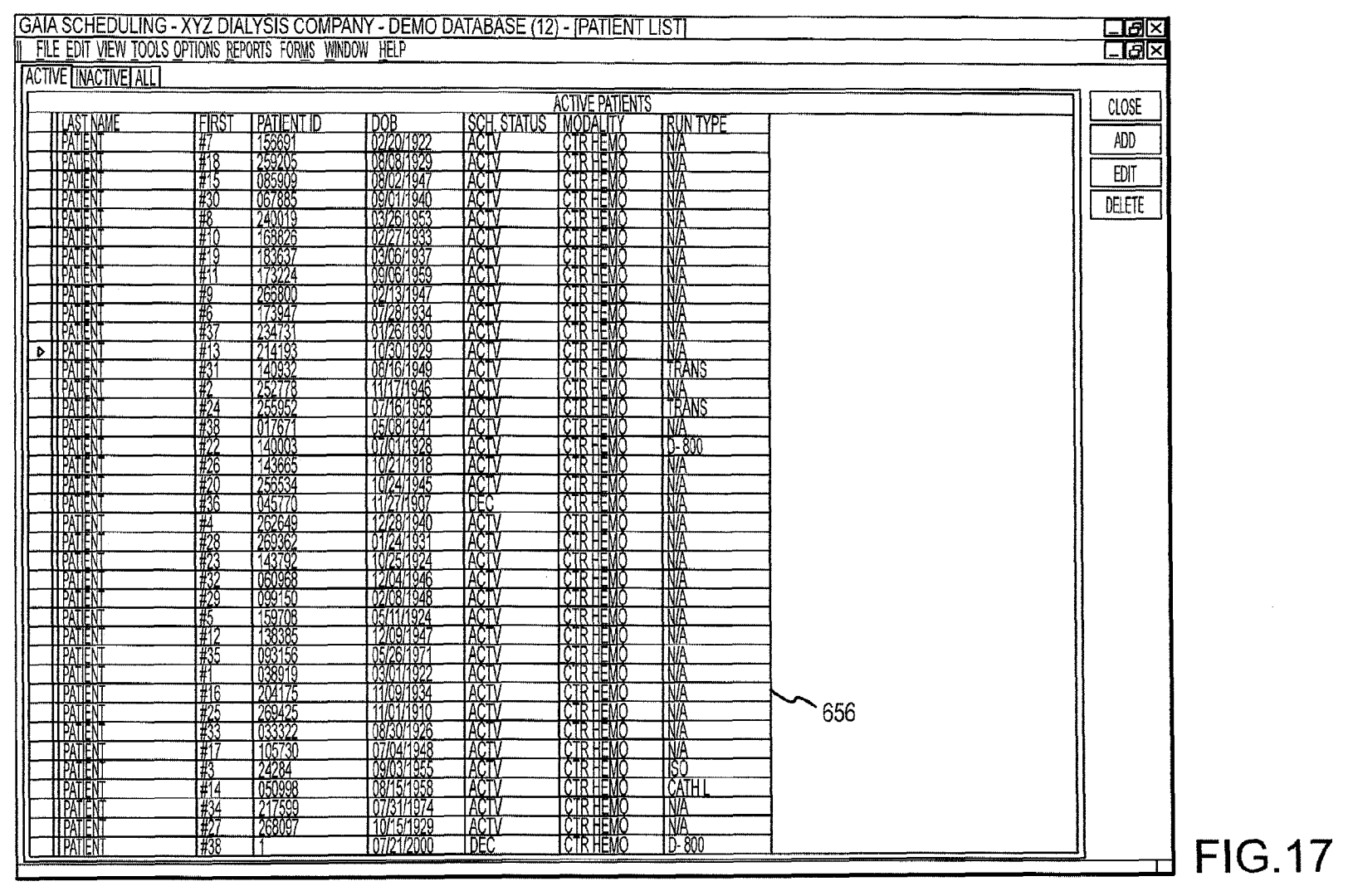
Figure 18:
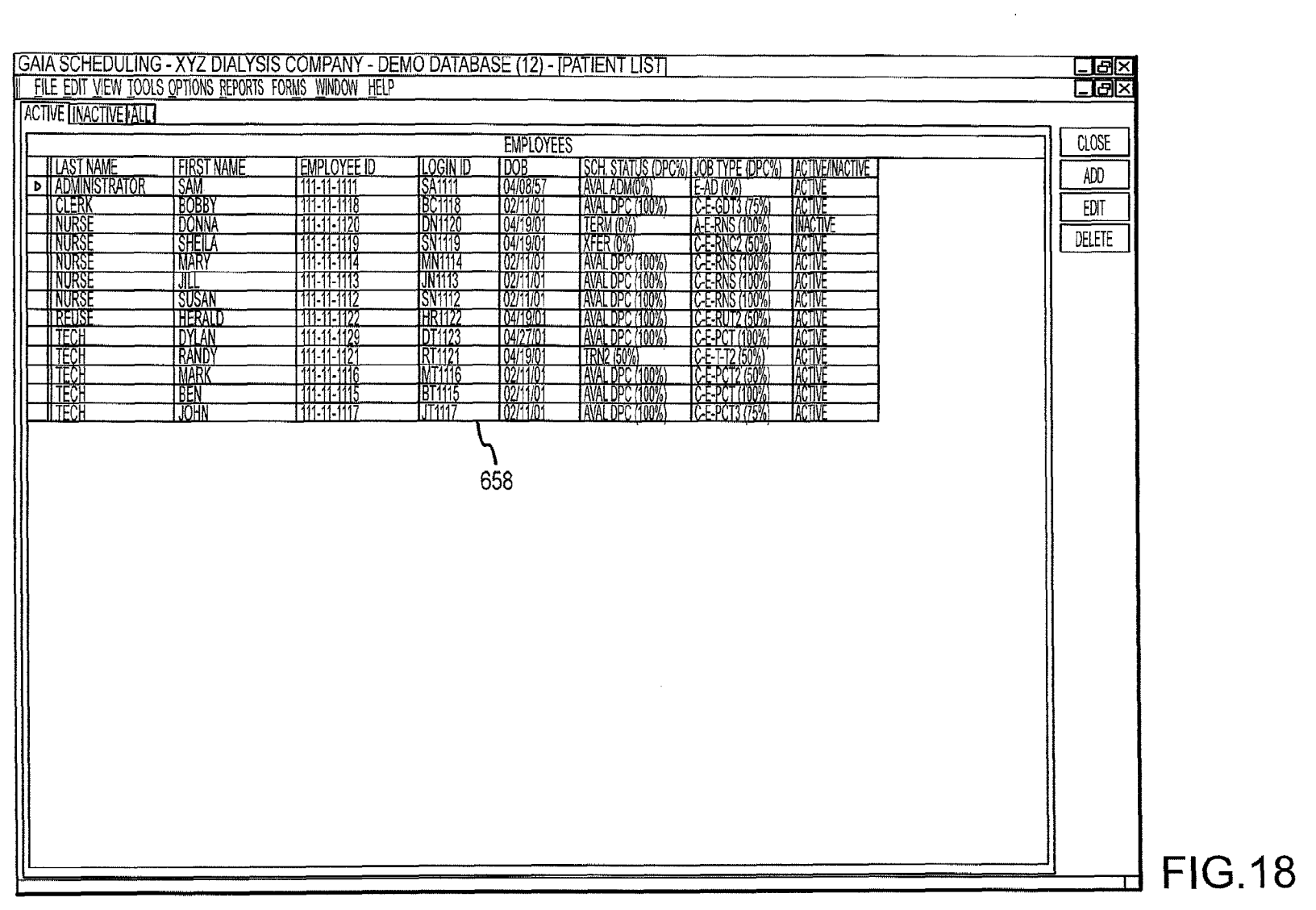

FIG. 16 illustrates a pull-down menu 654 representing various other pop-up windows that may be displayed, such as patient list window 656 (shown in FIG. 17) and employee list window 658 (shown in FIG. 18). As may be appreciated, the list windows 656 and 658 provide access for editing and display of all the patients in the system and all the employees in the system, respectively.

Figure 19:
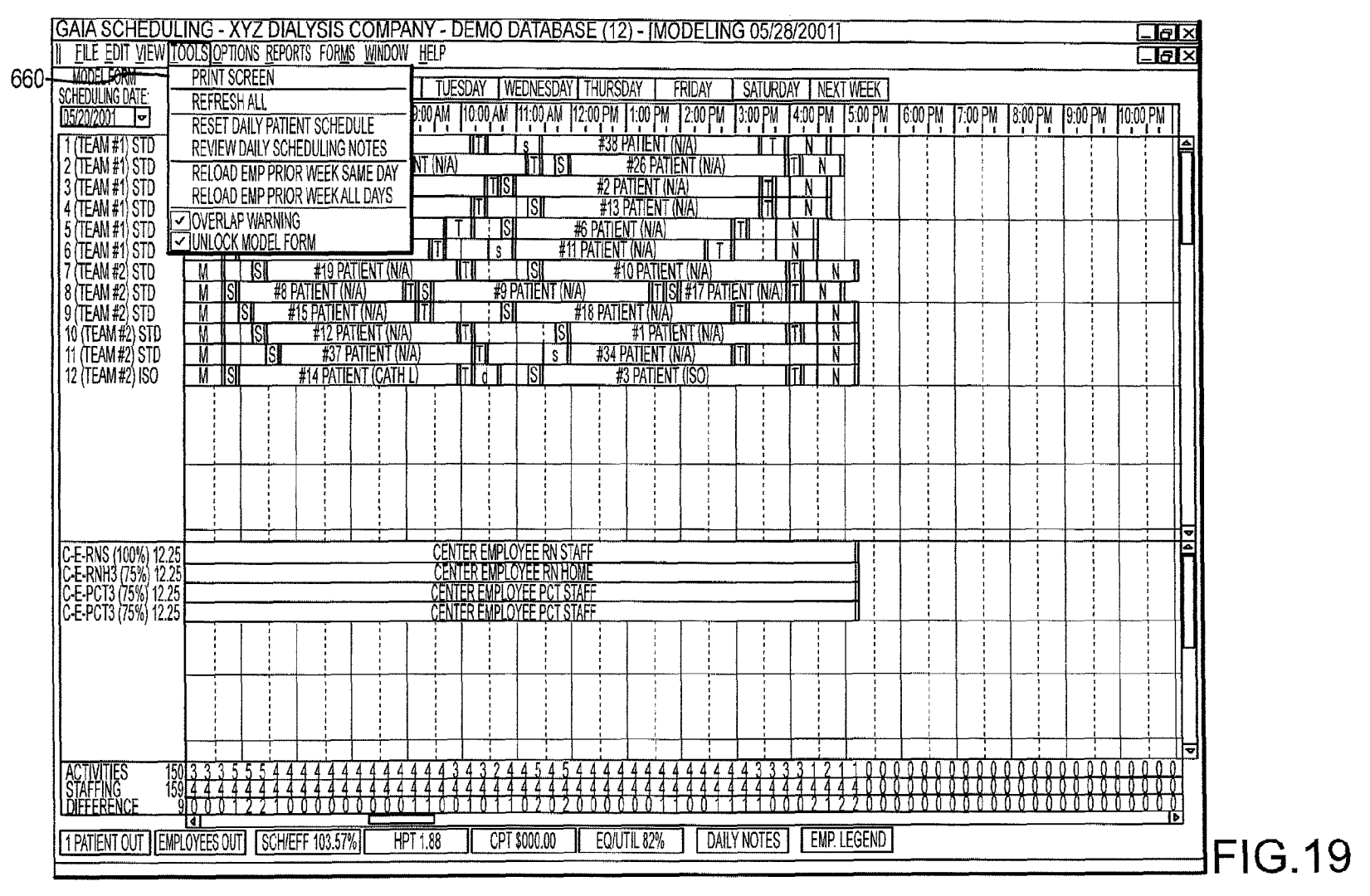
Figure 20:
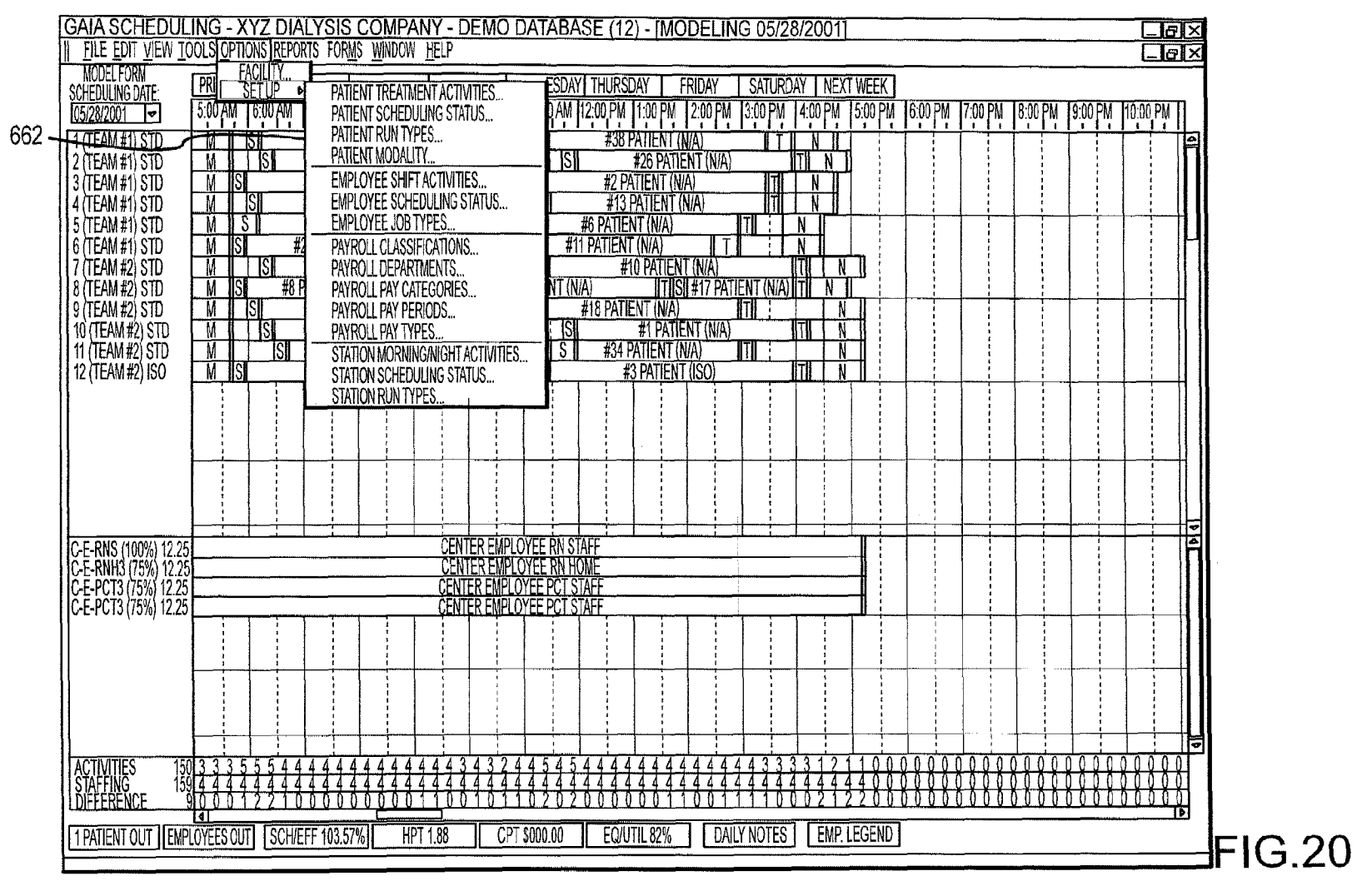
Figure 21:
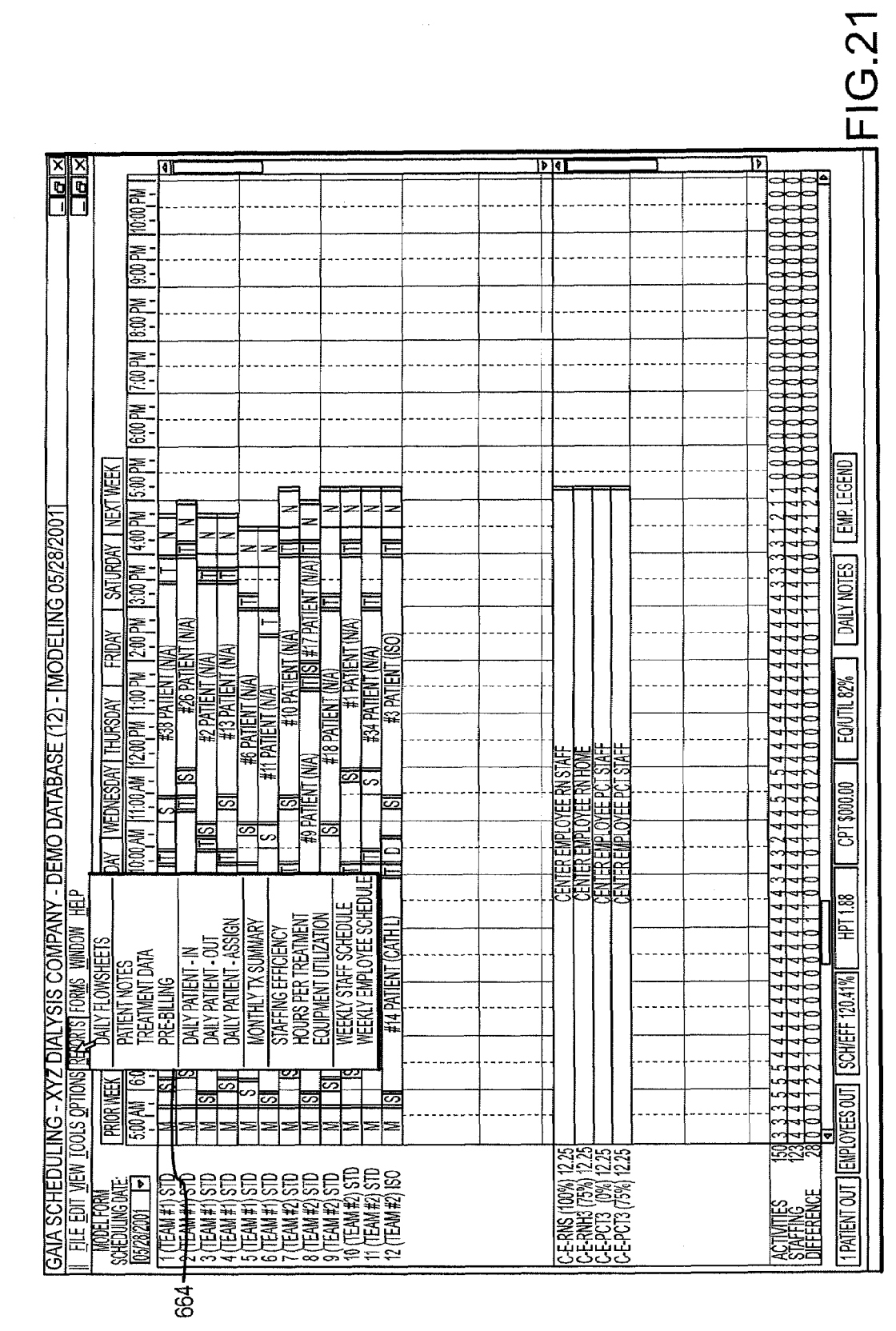
Figure 22:
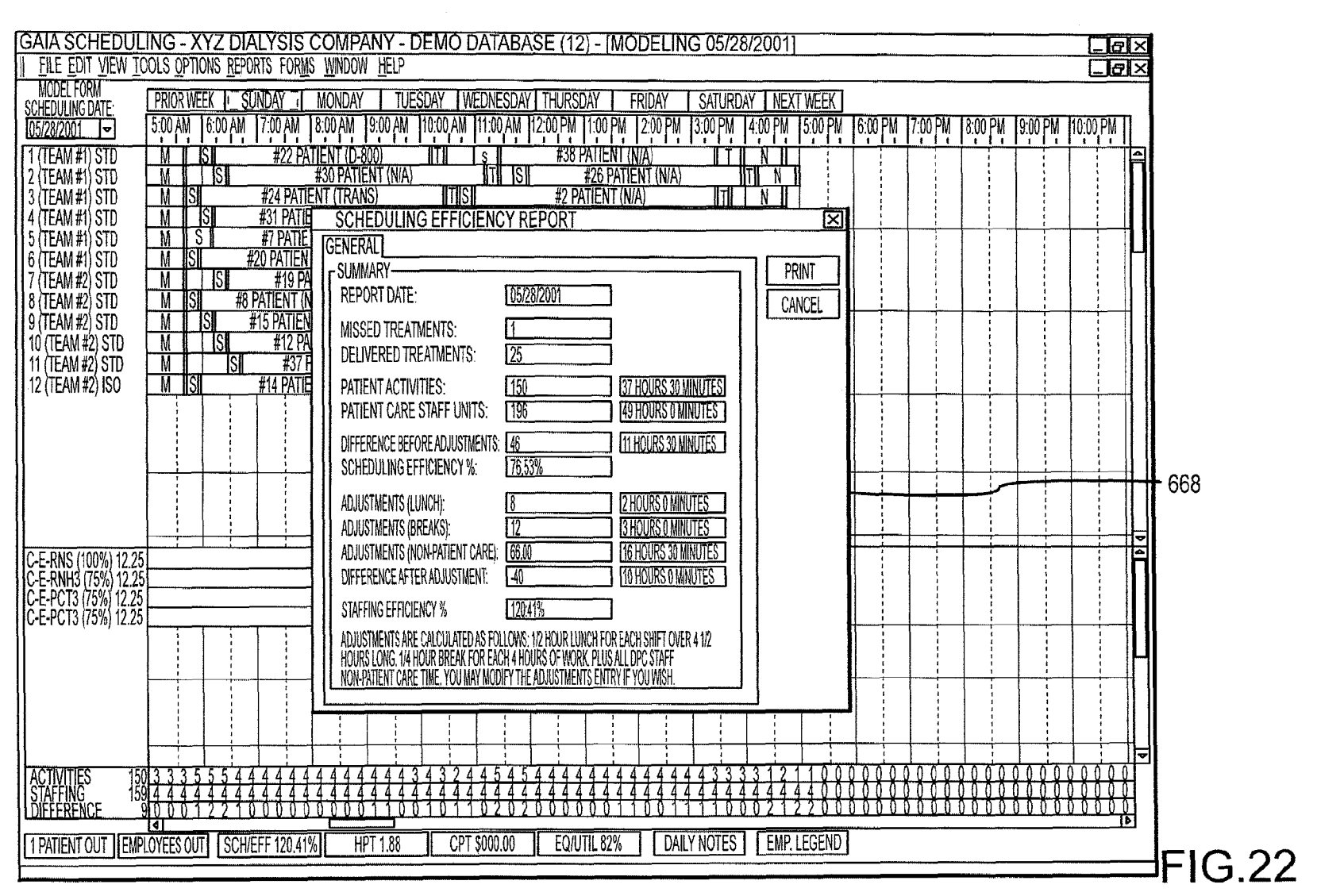

FIGS. 19, 20 and 21 illustrate pull down menus 660, 662 and 664 respectively. Menu 660 relates to various tools or other features that may be used to provide a better user experience. Menu 662, shown in FIG. 20, provides a list of various configuration or setup options that may displayed and configured. Menu 664 provides a list of options relating to various reports that may be generated. One report, the "Scheduling Efficiency Report" 668 is shown in FIG. 21. Another report, the "Hours Per Treatment Report" 670 is shown in FIG. 22.

One such report that may be generated relates to facility utilization. Facility utilization relates to comparing a particular facility's overall capabilities, e.g., total resources operating 100% of the time to meeting patient needs. In other words, the more patients satisfied, the higher the facility utilization. This report may further be used in comparing hours per treatment data to provide efficiency calculations related to the efficiency of the clinic or facility. In another embodiment, other reports relate to staffing efficiency which uses scheduling efficiency but combines other, non-patient care duties into the equation to provide an overall staffing efficiency report. In such a case, the staffing efficiency values can further be used in evaluating the efficiency of a clinic.

The above described system and method provides a significant advantage over prior methods of scheduling employees in the health care industry. In particular, the present system and method provides a means of averaging an employee's time over the course of a shift to more optimally account for the employees tasks and direct patient care availability. For example, if three patients that receive treatments during the same time only require direct patient care one-third of the time, then this system recognizes the fact and only schedules one employee to handle all three patients. Other, prior art methods, would force the scheduling of two or three employees to handle such a situation. Thus, once the empirical data (gathered by the past histories) relating to the needs of each patient has been entered into the system, the system can more efficiently schedule employees. Moreover, adding the empirical data relating to the employees (based on past histories or some other factor), the true capabilities of the employees can be ascertained and thus providing a more efficient scheduling method.

Figure 24:
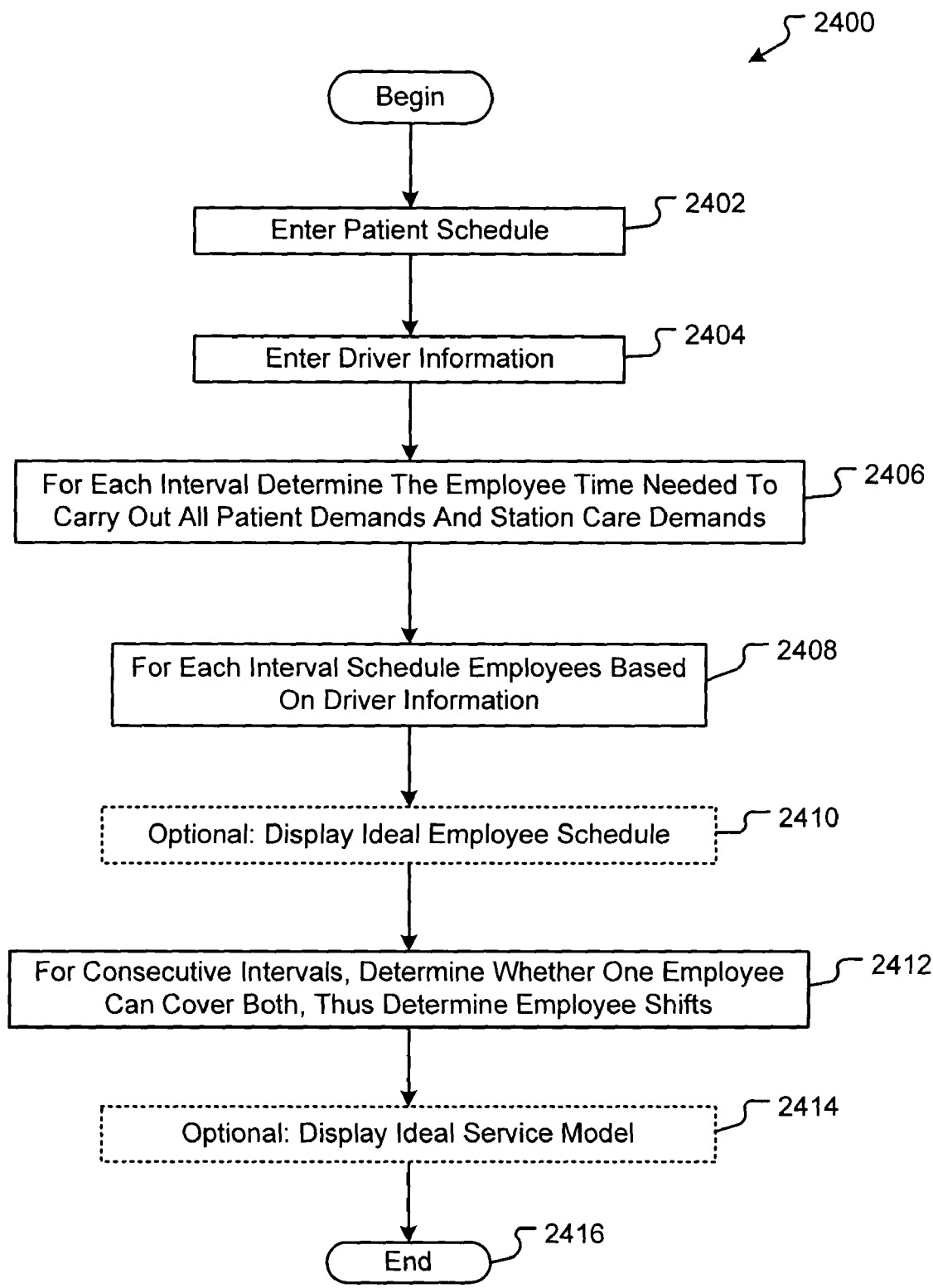
FIG. 24 is a flow diagram illustrating the functional components of scheduling employees based on a patient schedule using the optimization module shown in FIG. 3 in accordance with a particular embodiment of the present invention.

With respect to another embodiment, the module 302 (FIG. 3) provides for creating ideal patient scheduling and employee scheduling models. FIG. 24 is a flow diagram illustrating the functional aspects of creating an ideal employee schedule based on time intervals and also an ideal service or staff model, i.e., an employee schedule taking shift times into account, also referred to as an ideal staffing model grid. The process begins with enter patient schedule operation 2402. Enter operation 2402 relates to the creation of a patient schedule, such as the patient schedule 614 shown in FIG. 7. In one embodiment, the user simply enters the patients as desired according to the method described above. However, in another embodiment, the user enters the patients to be treated on a particular day and the optimization module automatically schedules the patients. Automatic scheduling is described in more detail below in conjunction with FIGS. 30 and 31. In essence, enter patient schedule 2402 simply relates to the preliminary act of having a set patient schedule and is not necessarily limited to any particular method of creating or entering the patient schedule.

Following enter patient schedule operation 2402, enter driver information operation 2404 enters the drivers to be used in computing an optimized employee schedule. Enter driver information operation 2404 is similar to enter patient schedule operation 2402 in that no particular method is required to enter such information. The drivers may be entered manually each time an ideal employee schedule is to be created or they may be retrieved from a previous session. Indeed, the operation 2404 may occur before or after enter patient operation 2402. In an embodiment, the driver information is manually calculated by a user and then entered into the system. In another embodiment, the system calculates the driver information from historical actual-use data. In order to have the system automatically calculate the drivers, the system must be used for a predetermined period of time to create enough historical data to allow for such a calculation. Otherwise, the system would have to be pre-loaded with some historical data.

In a particular embodiment, the driver values relate to (a) the ratio of nurses to non-nurses, (b) the percentage of nurse direct patient care, (c) the percentage of non-nurse direct patient care, and (d) the allowance for intermittent acuity. The values are called drivers since these values drive the resulting employee schedule. The user interface for displaying (and entering the drivers in an embodiment) the drivers is described below in conjunction with FIG. 26.

Once the drivers are loaded, determine operation 2406 determines the employee needs based on patient demands for each time interval in the day. Determine operation 2406 is the same as operations 406, 504 and 506 described above in conjunction with FIGS. 4 and 5. Accordingly, determine operation 2406 determines the patient requirements for each time interval.

Upon determining the patient needs for each time interval, schedule operation 2408 schedules the required employee types for each time interval. Schedule operation 2408 uses the entered driver information to schedule the employee types required. The use of the drivers to schedule the employees per each interval is shown and described in conjunction with FIG. 25 below. Importantly, this step is referred to as modeling the staffing requirements wherein the job-type portions are placed on the daily form, i.e., scheduled for a particular day. The act of scheduling employees comes later and involves the assigning of individual employees to specifically scheduled or modeled job-type portions.

Figure 11:
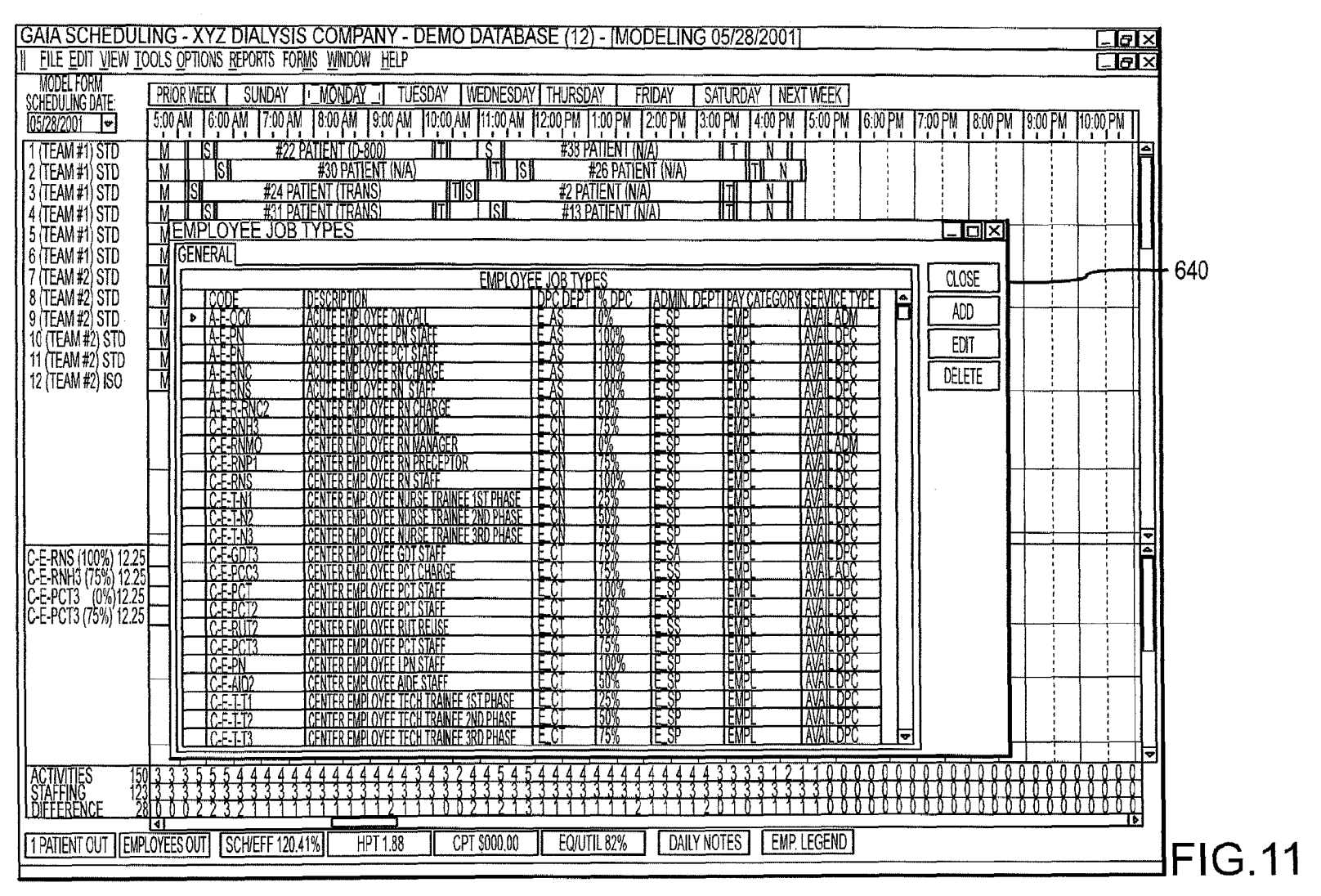

In an embodiment, the employee job types are each assigned one default employee shift activity e.g. "Direct Patient Care", as shown in FIG. 11. These default shift activities may be changed on a daily basis if the employee that is assigned to that specific job type widget is going to be doing different work assignments other than the default shift activity. If the default shift activity has been changed the color of the widget and the % DPC may also be changed to reflect the new values on the model scheduling form. Later, once an employee is scheduled, then the employee scheduling status, an employee specific issue, denotes if the employee is able to fulfill all of the required job type duties e.g. not fully trained or limited by other restrictions. This employee specific percentage is displayed on the job type portion following the employee name once the employee has been scheduled to work this specific job type portion. The actual value of direct patient care "DPC" time allocated to the specific employee is the sum of the "% DPC" for the job type/shift activity noted on the daily model scheduling form multiplied by the employee scheduling status "% Available for DPC" noted after the employee name on the job type portion that counts towards the scheduling efficiency calculations for available DPC time. If there is no employee assigned to a specific job type portion then the default employee scheduling status is assumed to be 100% availability.

Upon determining the number of employees of each job type, e.g., how many nurses and non-nurses are required for each element, an optional display operation 2410 may be implemented. Display operation 2410 may provide the user with a visual representation of how many employees of each type are required for each time interval. An exemplary display is shown and described below in conjunction with FIG. 27.

Given that the time intervals are typically much smaller than shift lengths, determine operation 2414 is employed to determine an ideal staff or service model schedule with acceptable shifts based on the schedule created in operation 2408. For instance, in an embodiment, the time intervals used to determine patient requirements are approximately 15-minute intervals. Since employees do not want to be scheduled for 15-minute shifts, a compromise must be made when patient needs do not span consecutive intervals or do not extend to account for a satisfactory employee shift length.

In one embodiment, employees are first scheduled based on the first interval, with shift lengths based on the minimum allowable shift size. Determine operation compares consecutive intervals having patient demands. Using these consecutive intervals, determine operation 2412 determines whether potential employees scheduled for one interval can also satisfy the demands of the next interval. A test must be done to make sure the assigned shifts do not exceed the maximum shift size. If so, then a second employee shift must be added. Also if a subsequent interval requires more or less employees, determine operation 2412 can add new employees or end the shifts of existing employees.

Upon determining the employee schedule based on shift length 2412, an optional display operation 2414 may display the resulting employee schedule. An exemplary display is shown and described below in conjunction with FIG. 29. The user may then visualize the needs for the day based on employee type and the shift lengths.

Following display operation 2414, flow 2400 ends at end operation 2416. Although not shown, once the model for the ideal schedule is complete, i.e., flow 2400 ends, then a user can manually assign actual employees for the displayed job types and shift lengths. Since some employees may not be able to provide the same percentage of direct patient care as identified in the model, a recalculation step may be required to determine the actual efficiency of the final, actual employee schedule.

Figure 25:
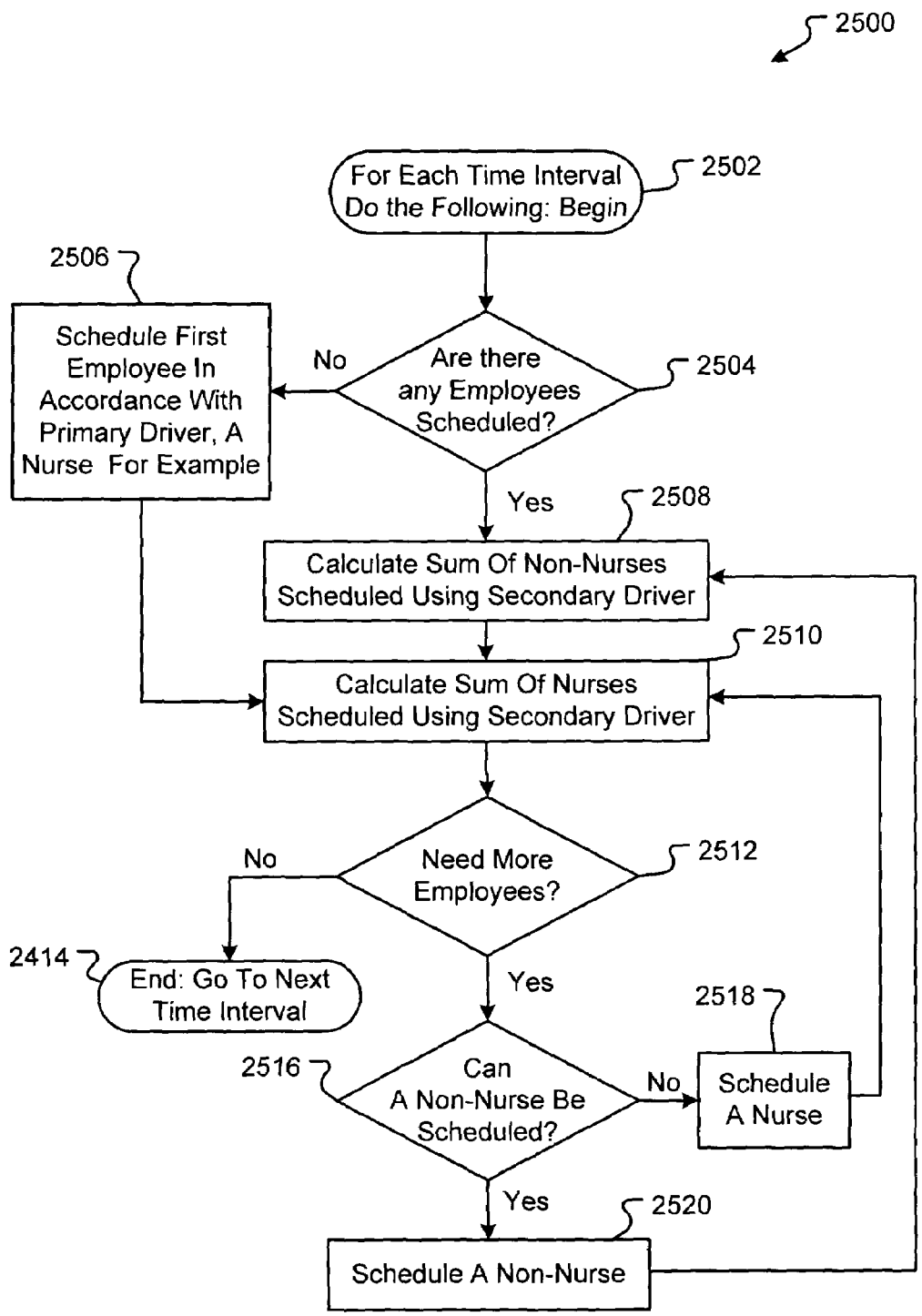
FIG. 25 is a flow diagram illustrating the functional components of scheduling employees based on employee job type and based on time intervals.

FIG. 25 is a more detailed flow diagram illustrating the functional aspects of operation 2408 (FIG. 24) of creating an ideal employee schedule based on time intervals. Flow 2500 begins with begin operation 2502 identifying that flow 2500 is repeated for each time interval having direct patient care demands based on the patient schedule. Initially, flow 2500 begins with test operation 2504 which tests whether any employees have been scheduled for the time interval. Typically, there will not be any employees scheduled such that scheduling a first employee is generally the next step. However, since the system is designed to allow the user to manipulate the schedule and recalculate the needs of the patient schedule, it is contemplated that the employees may already be scheduled such that test operation 2504 is needed.

If test operation 2504 determines that no employees have been scheduled, then flow branches NO to schedule operation 2506 which schedules the first employee for the time interval. Schedule operation, in an embodiment, schedules the first employee for the time interval in accordance with a primary driver. For example, if one of the drivers has mandated that a nurse must be scheduled for every three non-nurse employees, it may also be mandated that no non-nurse employees can be scheduled until a nurse has first been scheduled. Other embodiments may modify this driver to schedule employees in other orders. Upon scheduling the first employee, flow branches to calculate operation 2510, discussed below.

If test operation 2504 determines that an employee has already been scheduled, then flow branches Yes to calculate operation 2508. Calculate operation 2508 adds the number of non-nurses scheduled for the interval. In doing so, calculate operation 2508 takes secondary drivers into account. For example, one of the secondary drivers relates to the percentage that an employee that is listed as a non-nurse dedicates to direct patient care, e.g., 80%. Consequently, the summation of scheduled non-nurses is a straightforward calculation of the number of non-nurses scheduled multiplied by the secondary driver value, e.g., 80%. The resulting sum is the number of non-nurses available for direct patient care during that interval. It should be noted that the secondary drivers are only referred to herein as secondary drivers to distinguish them from the other driver relating to the nurse to non-nurse ratio, which has been arbitrarily labeled "primary" above.

Following calculate operation 2508 (and following schedule operation 2506), flow continues with calculate operation 2510. Calculate operation 2510 adds the number of nurses scheduled for the interval. In doing so, calculate operation 2510 takes a secondary driver into account, as did operation 2508. However, calculate operation 2510 takes a different secondary driver into account than calculation 2508. For example, one of the secondary drivers relates to the percentage that an employee of type "nurse" dedicates to direct patient care, e.g., 90%. Consequently, the summation of scheduled nurses is also a straightforward calculation of the number of nurses scheduled multiplied by the secondary driver value, e.g., 90%. The resulting sum is the number of nurses available for direct patient care during that interval.

Next, determine operation 2512 determines whether more employees should be scheduled. In order to determine whether more employees are needed, determine operation simply compares the sum of operation 2508 and 2510 (to get a total number of employees scheduled for direct patient care for the interval) to the number of employees required to satisfy the patient demand for the interval, which was determined previously, such as in operation 2406 (FIG. 24). Furthermore, determination operation may also factor in the last driver, relating to the intermittent acuity to see if another employee should be added to cover foreseeable, yet not scheduled, patient demands. If determination operation 2512 determines that no additional employees are needed, i.e., the sum of 2508 and 2510 is greater than the needs identified in 2406 plus intermittent acuity, then flow branches No to end operation 2414.

If, on the other hand, more employees are needed, than flow branches Yes to test operation 2516. Test operation 2516 tests whether a non-nurse can be scheduled. That is, using the primary driver, test operation can test whether the addition of another non-nurse will violate the rule regarding the nurse to non-nurse ratio. If so then a non-nurse cannot be added. In such a case, flow branches No to schedule operation 2518 which schedules a nurse and then branches to calculate operation 2510 to add the new nurse to the running total and start the test operation 2512 over again. If, on the other hand, a non-nurse can be added, as determined by test operation 2516, then flow branches Yes to schedule operation 2520 which schedules a non-nurse and then branches to calculate operation 2508 to add the new non-nurse to the running total and start the test operation 2512 over again. Operation 2508, 2510, 2512, 2516, 2518 and 2520 continue until test operation 2512 determines that no more employees are needed for the interval and branches to end operation 2414.

Figure 26:
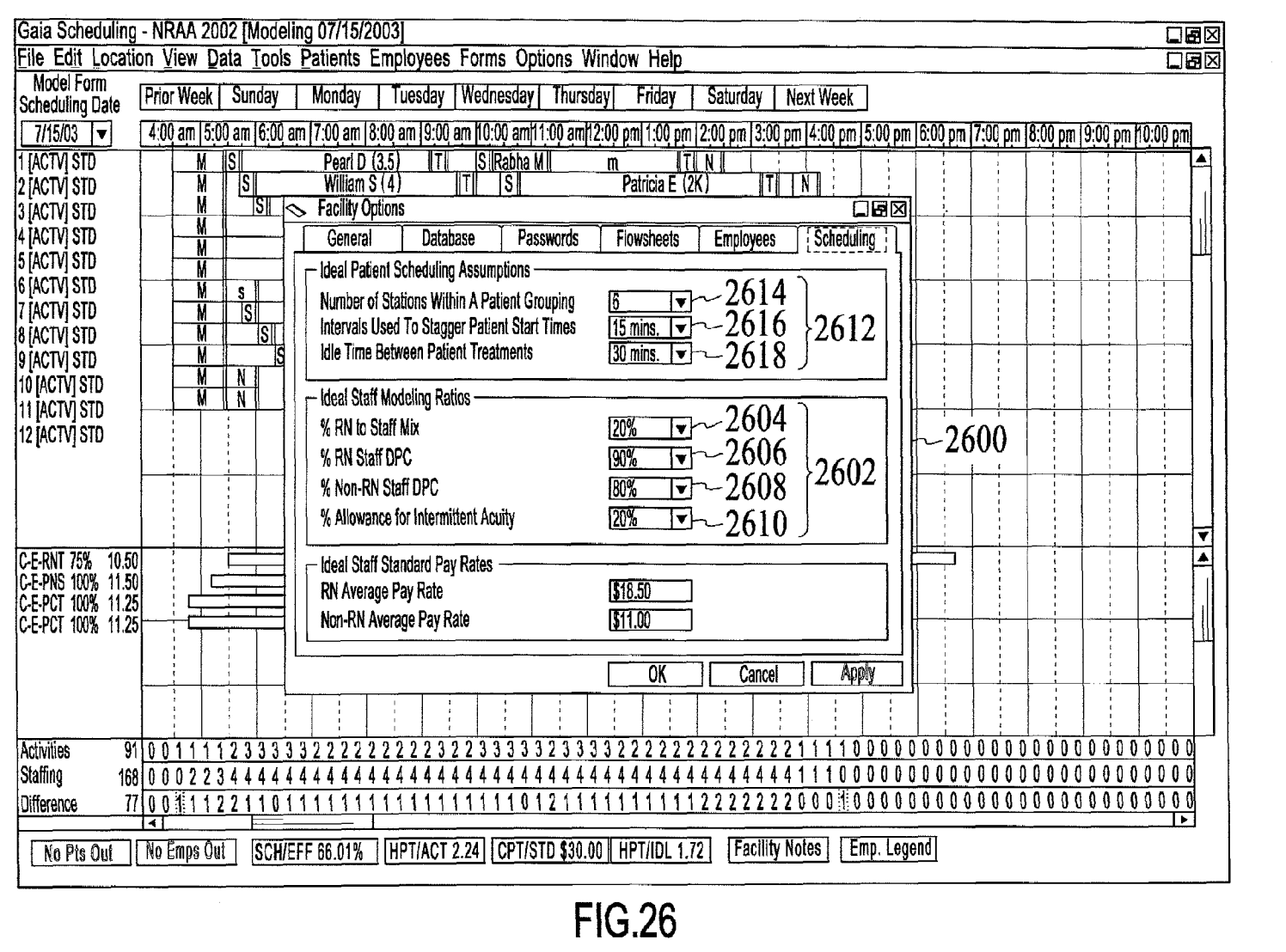

FIG. 26 illustrates a screen shot showing the existing drivers for the system. In this embodiment, the drivers are accessed through pull down menus leading to the Facility Options window control. The pop-up window provides multiple tabs, wherein one is the scheduling tab. Upon selecting the scheduling tab, the employee scheduling drivers 2602 are displayed. In yet another embodiment, the drivers 2602 may be modified from this window. Of course, many other methods and means may be used to both display the drivers and edit the same.

Four employee scheduling drivers 2602 are shown in FIG. 26. The first driver 2604 is the primary driver and relates to the ratio of nurses to non-nurses. An example value of 20%, as shown in FIG. 26, means the system will schedule one nurse for every four non-nurse employees. Moreover, in accordance with a particular embodiment, the system will use this driver to ensure that no more than four non-nurse employees will be scheduled prior to scheduling another nurse. The second and third drivers, 2606 and 2608, respectively, are described above as secondary drivers and relate to the percentage of time that a nurse or non-nurse, respectively, are available for direct patient care. The last driver is the percentage value allowed for intermittent acuity.

Also shown in FIG. 26 are the drivers relating to creating the ideal patient schedule 2612, discussed in more detail below.

Figure 27:
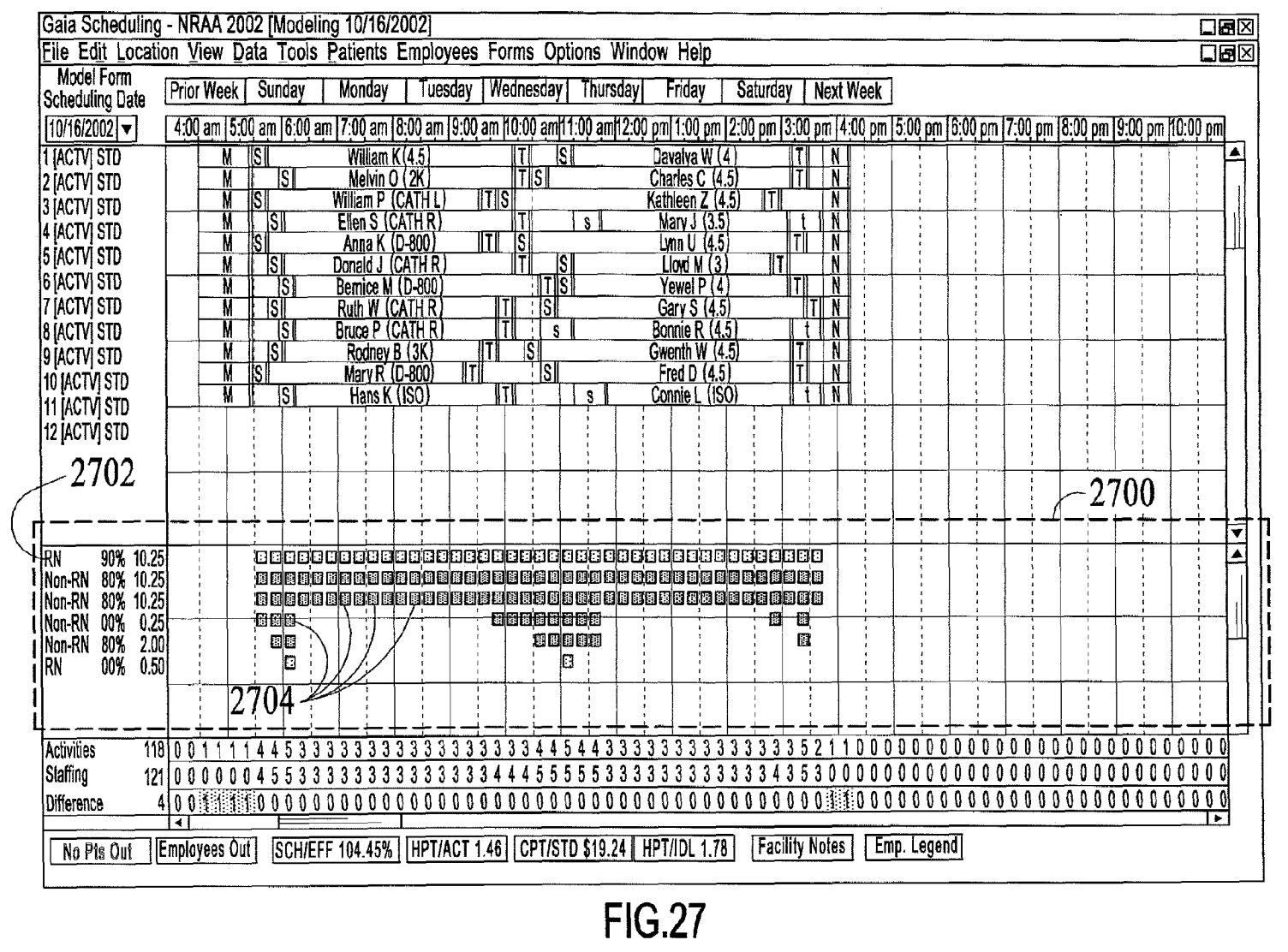

FIG. 27 illustrates a screen shot showing an ideal patient schedule based on employee types and based on time intervals. As shown the employee scheduling section 2700 is used to display the scheduled employees. Preferably, the types of employees are shown in different colors for simplicity. However, as shown in the area 2702, the employee types are provided for each row. Consequently, the user can readily determine the number of nurses (RNs) and non-nurses (Non-RNs) scheduled for a particular day. In the example shown in FIG. 27, two nurses are scheduled while four non-nurses are scheduled. Next to the job-type title, the percentage of time devoted to direct patient care for that job type is also provided, e.g., 90% for nurses and 80% for non-nurses. Also shown in area 2702 is the total number of hours required for that particular job-type slotted in a particular row. This value is the sum of all scheduled intervals for that row.

Area 2700 also displays, graphically, the schedules for the employees based on patient demands. In essence, blocks 2704 each denote the requirement for an employee for that particular time interval. Using this graphical display, the user can readily determine the areas where patient demands are much higher than others. Using this information, the user may move patient schedules around to see if employees may not be needed for an adjusted patient schedule.

Figure 28:
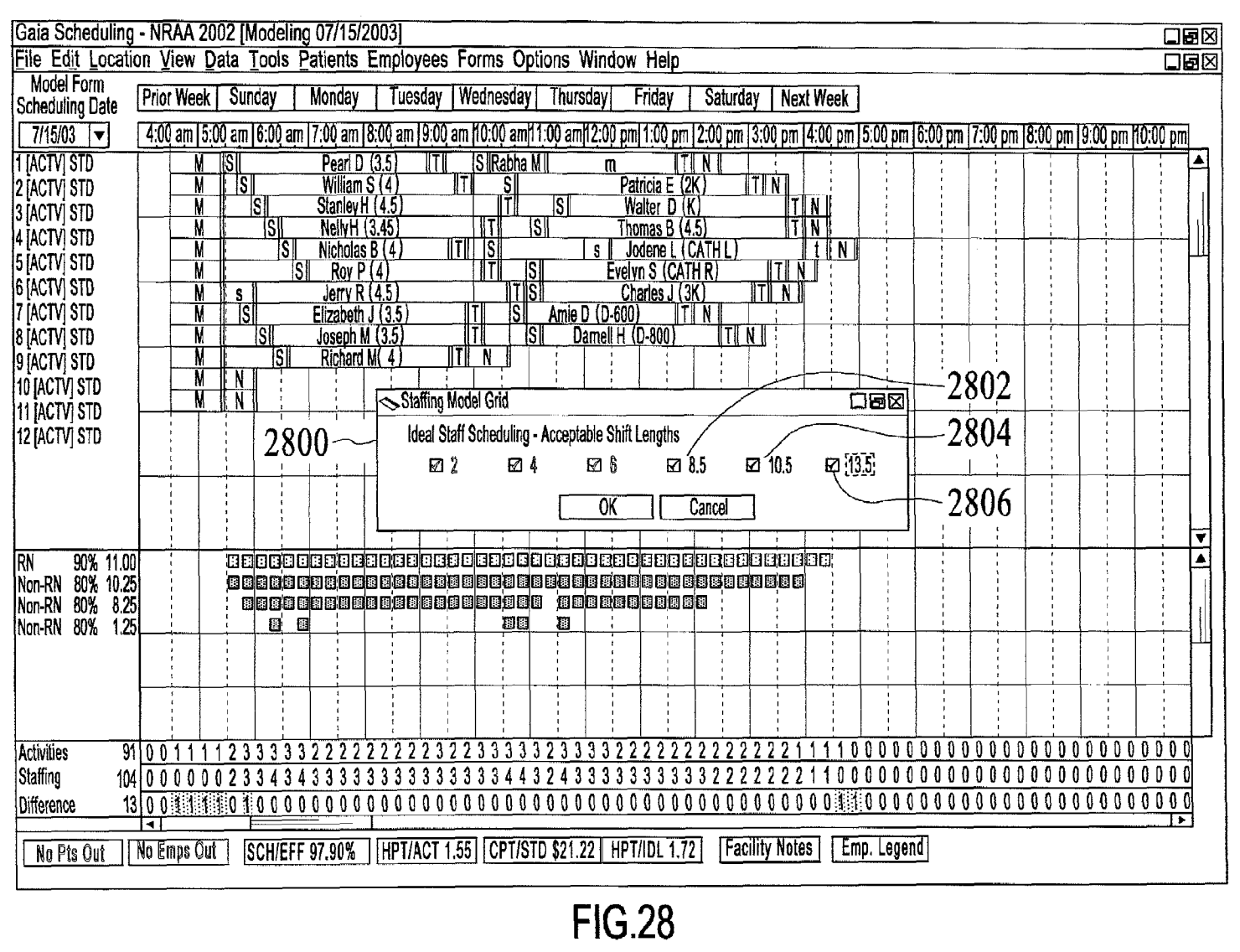

Once the user is satisfied with the ideal patient schedule based on time intervals, the user may then desire to see what the employee schedule looks like upon taking shift times into account. In an embodiment, the user may select what shift times are acceptable. For instance, FIG. 28 illustrates a screen shot showing a pop-up window 2800 control that allows the user to select acceptable shift lengths. The example provides shift lengths of 2 hours, 4 hours, 6 hours, 8.5 hours, 10.5 hours and 13.5 hours. It should be understood that these values are exemplary and that other shift values may be used. As shown in FIG. 28, shift value 2802 (8.5 hours), shift value 2804 (10.5 hours) and shift value 2806 (13.5 hours) have all been selected and thus are all acceptable shift lengths that the system can use in determining an ideal service model.

Figure 29:
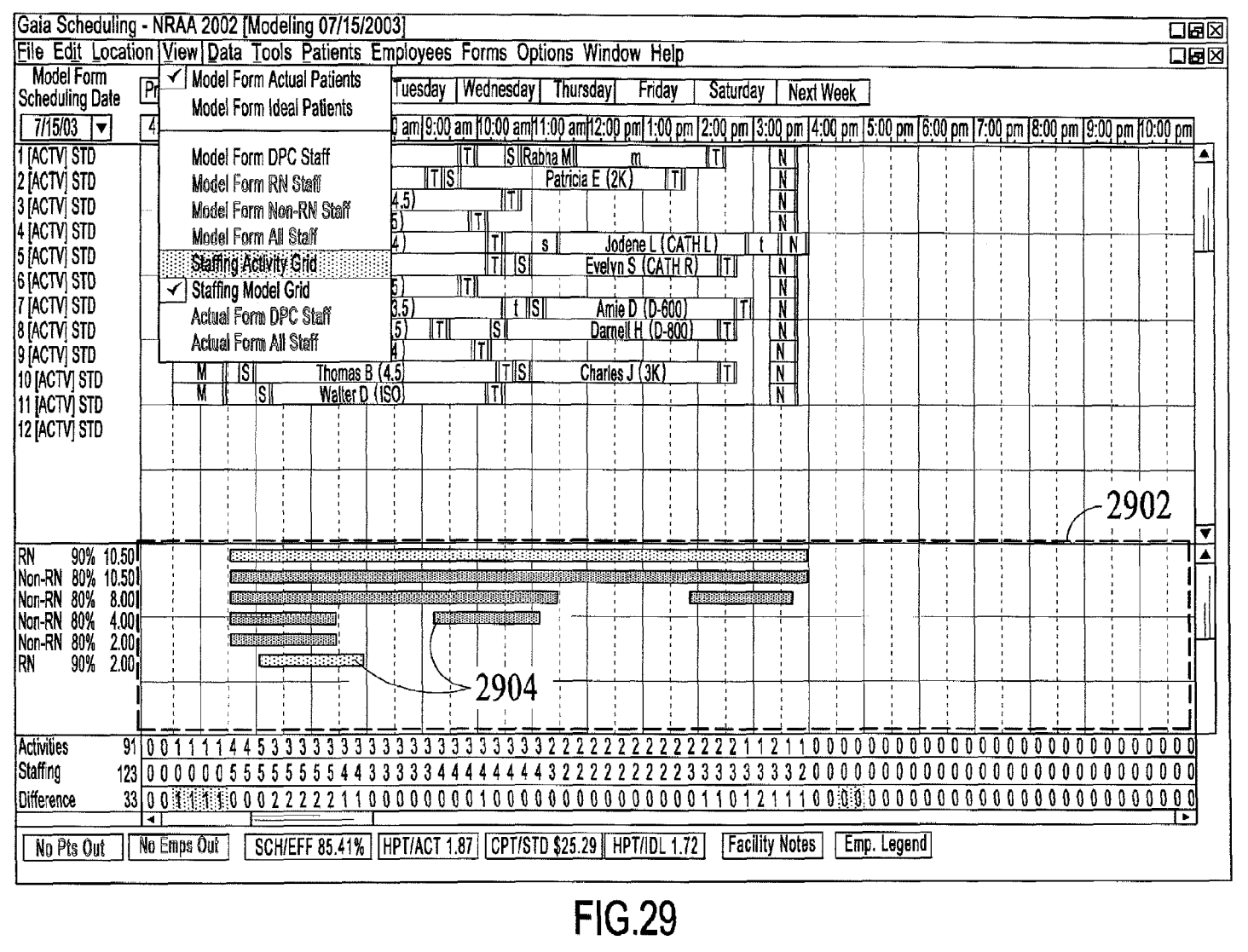

Upon requesting such an ideal service or staffing model, the system displays the shifts for each scheduled employee, as shown in FIG. 29. In essence area 2902 replaces the previous staffing activity grid (or ideal employee schedule based on time intervals), with the staffing model, also referred to as an ideal staffing model or grid, incorporating acceptable shift lengths. The shifts are shown by colored rows 2904.

As discussed above, in an embodiment of the invention, the module 302 (FIG. 3) includes an optimization module 370 that further comprises a calculate module for calculating an ideal patient schedule, independent of an employee schedule. That is, the ideal patient schedule seeks to minimize the number of employees required throughout a day by adjusting the patient start times, station locations, etc. By performing a series of calculations and/or patient schedule manipulations, the patient schedule can be optimized which then leads to a more ideal and more efficient employee schedule.

Figure 30:
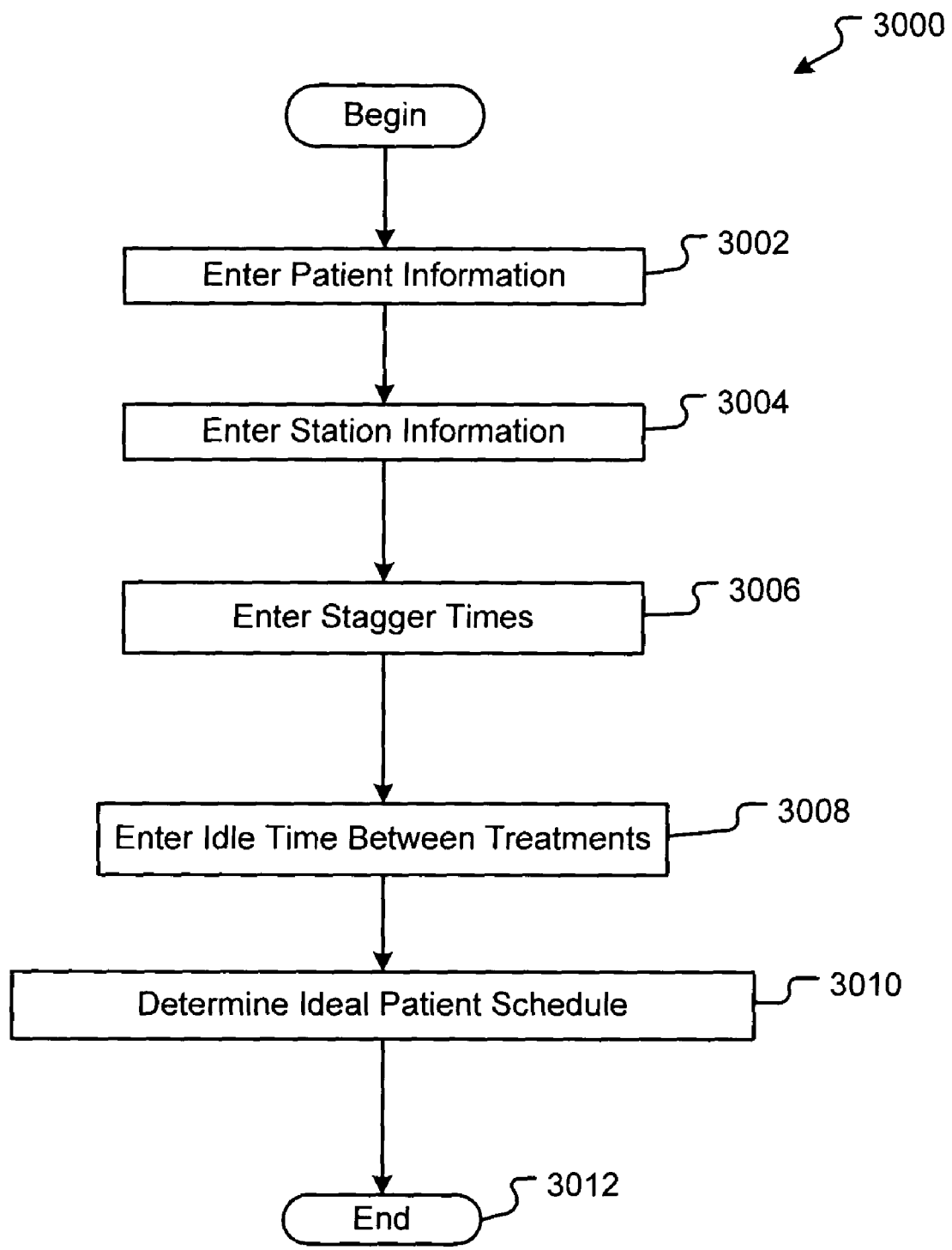
FIG. 30 is a flow diagram illustrating the functional components of a patient-schedule optimization module in accordance with the present invention.

FIG. 30 is a flow diagram illustrating the functional aspects of creating an ideal patient schedule in accordance with an aspect of the present invention. Flow 3000 demonstrates, at a high level, the concepts involved in automatically generating an ideal patient schedule. First, enter operation 3002 enters the necessary patient information. Enter operation 3002 may involve the data entry into patient profiles, such as profiles 320, 328 and 330 (FIG. 3). In other embodiments, enter operation 3002 may further relate to retrieving the patient profiles from memory 306 to be used in future calculations. The patient information that is entered involves the patient requirements, such as treatment data. For instance, the treatment data may involve the type of treatment to be preformed, any special direct patient care requirements, the timing of the treatment, etc. Indeed, this information provides module 370 the ability to determine the employees and resources needed to satisfy the needs of the patient.

Following enter operation 3002, enter station information 3004 enters the necessary information regarding the available resources, i.e., stations. For instance, station information may relate to the number of dialysis machines in a clinic, among other things, as discussed above. In a particular embodiment, the resource information may be entered within pop-up window 2600 as shown in FIG. 26. That is, the number of stations value 2614 may be entered or modified from this particular graphical user interface control. Of course, other methods may be used to enter the resource information. Also, the system may include other, more specific information regarding the actual stations, used in calculating the ideal patient schedule. In a particular embodiment, the number of stations 2614 actually relates to the number of stations per "patient grouping" wherein a patient grouping is an arbitrary label to identify a predetermined number of stations that are grouped together for scheduling purposes. In the display shown in FIG. 26, there are twelve stations, but only six stations are assigned to a group. In this manner, stagger times, discussed below, can be assigned to smaller groups.

Upon entering the number of stations, enter operation 3006 enters the stagger and idle times to be used in calculating the ideal patient schedule. Stagger times relate to the time intervals between start times of the various stations. For instance, when using a 15 minute stagger time, the various machines will be started 15 minutes apart. In many instances, the stations require employee time, i.e., direct patient care, to manually prepare and start a particular station. The stagger time is generally set based on the time it takes to complete the setup and start procedure to allow one employee to finish one station and then start on the next station. If the stagger time is set to less than the time it takes to complete a setup procedure, then the overlap forces the scheduling of more employees to complete the start process. Consequently, adjusting the stagger time allows for optimizing the patient schedule, in terms of balancing the needs for direct patient care. The stagger time may be entered and adjusted from pop-up window 2600 (FIG. 26), shown as 2616.

Next, enter operation 3008 enters the idle times between sessions. The idle times between sessions relates to the time between two patients' use of the same station. For instance, when one patient completes a session on a station, there may be some idle time scheduled before that station is ready to be prepped and subsequently used by another patient. Of course, the idle time may be set to zero such that the station is used relatively immediately following the completion of a session. However, scheduling idle time, e.g. 30 minutes, between sessions allows for flexibility in scheduling patients based on direct patient care needs. The idle time also provides a cushion for other potential problems, or intermittent acuity, wherein the first patient shows up late or needs a longer treatment, etc. The idle time may be entered and adjusted from pop-up window 2600 (FIG. 26), shown as 2618.

Following enter idle time operation 3008, determine operation 3010 calculates or determines the ideal patient schedule for the given set of patients and then flow 3000 ends at end operation 3012. The details of determine operation 3010, with respect to one embodiment of the invention are provided below in conjunction with FIG. 31. In general however, the process assigns shifts to patients based on their preferred times for treatment. Next, the system assigns shifts by filling shifts per day for each station. Following the assigning of actual shifts, the system staggers the start time for the first shift based on the stagger information 2616. Upon setting the first shift based on stagger times, the second shift is set based on idle times. The resulting patient schedule is considered "ideal" in that it incorporates the proper stagger and idle times.

Figure 31:
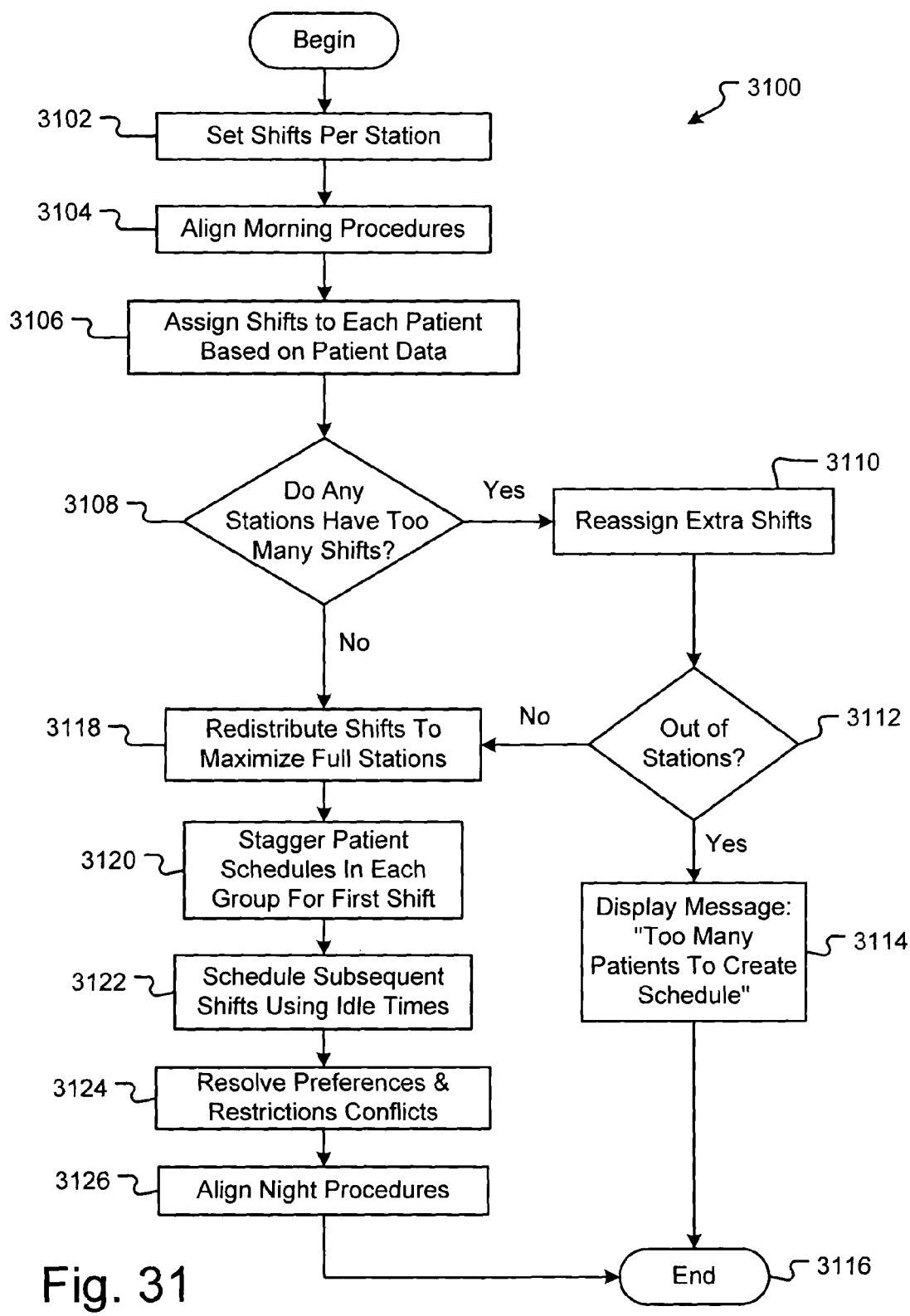
FIG. 31 is a more detailed flow diagram of the functional components of a patient-schedule optimization module described in FIG. 29 with respect to particular aspects of the present invention.

A more detailed flow chart of functional operations for determining the ideal patient schedule is provided in FIG. 31. Flow 3100 is, therefore, an embodiment relating to determine operation 3010 shown in FIG. 30. Initially, flow begins with set operation 3102 wherein a user sets the number of shifts per station. In essence, as discussed above, the number of stations has been entered into memory prior to set operation 3102. Typically the stations relate to a particular resource that can be re-used in shifts. For instance, a dialysis machine may be the "station" in one embodiment and the dialysis machine may be reused every six hours, for example. In such a case, for a twenty-four hour period, there may be up to four shifts or separate segments of time that the station may be used. In other embodiments, the resource or station may be re-used every four hours such that six shifts may be acceptable. Furthermore, since many clinics may not operate twenty-four hours a day, then the actual shifts per day may be less to accommodate business hours. In a particular embodiment, the user is prompted to enter the number of shifts for the day to be scheduled.

Following set operation 3102, align operation 3104 aligns the morning procedures. Aligning the morning procedures sets the time for all the automatic morning operations that, all totaled, do not require direct patient care activities, in this one embodiment. That is, morning procedures are activities that are not related to direct patient care but are activities that employees must complete in order to prepare the facility to treat patients, i.e. direct patient care activities. In other embodiments, the morning procedures are not aligned.

Next, assign operation 3106 assigns shifts to each patient based on patient data. That is, upon entering a patient into the database, the patient may have an associated time which they desire treatment. For example many patients may desire to be treated in the morning instead of the afternoon, or vice versa. Assign operation 3106 "loads" the patients for a particular day, i.e., temporarily places patients treatment slots based on (a) whether they are to be treated that day and (b) which shift is preferred or required by the patient. Hence, assign operation 3106 assigns these preferred shifts to the patients that are to be treated on a particular day.

Upon assigning shifts to all of the patients based on patient profile data, analyze operation 3108 analyzes the temporary schedule to determine whether any of the stations have been assigned too many shifts. That is, analyze operation compares the number of patients scheduled for treatment on each station against the number of shifts per station entered during operation 3102 to see if there are too many shifts assigned to any of the stations. If so, flow branches Yes to reassign operation 3110. Reassign operation 3110 reassigns extra shifts, i.e., those shifts that exceed the number set during operation 3102 to another station.

Following and/or during reassign operation, test operation 3112 tests to see if some shifts cannot be reassigned because of the lack of stations. If so then flow branches Yes to display operation 3114 which displays an error messages, such as "Too many Patients To Create Schedule" since there are not enough stations and shifts to accommodate all the patients for the given day. Upon displaying the error message, flow 3100 ends at operation 3116.

Referring back to analyze operation 3108, if analyze operation 3108 determines that no stations have too many shifts then flow branches No to redistribute operation 3118. Similarly, should test operation 3112 determine that following reassign operation 3110 that all patients can be accommodated, then flow branches No to redistribute operation 3118 as well. Redistribute operation 3118 moves patient schedules around to fill empty shifts and minimize the number of stations with less than full capacity. In an embodiment, the stations are ordered in a list and the process moves patients from the bottom of the list to towards the top of the list to fill or complete "upper" stations with the set number of shifts.

Upon redistributing the shifts to maximize the number of full stations, stagger operation 3120 staggers the patient start times for each group of patients by the stagger value entered. For instance, the stagger value may be entered at operation 3006 (FIG. 30) and set to 15 minutes. Consequently, in this example, the second patient of each group will be set to start 15 minutes after the first patient of the group. Next the third patient of the group, assuming the group has three or more patients, is scheduled to start 15 minutes after the second patient starts. This process continues until all patients in each group for the first shift have been scheduled. Importantly, there may be two or more groups of patients scheduled for the first shift.

Following stagger operation 3120, schedule operation 3122 schedules subsequent shifts. In essence, schedule operation 3122 schedules each patient not in the first shift to start a predetermined period of time after the completion of the preceding patient. In an embodiment, the predetermined period of time is the idle time set in operation 3008 (FIG. 30). More specifically, the process of scheduling the patients involves determining the preceding patient's completion time and then adding the idle time to the scheduled completion time and scheduling the patient to the sum of the two values.

Next, resolve operation 3124 resolves any preferences and/or restrictions conflicts. In essence, each patient has a set of preferences and restrictions associated with that patient. In some cases, the scheduling process outlined above may cause a conflict with one or more of these preferences and/or restrictions. As a result, resolve operation 3124 cycles through the conflicts and juggles the various patient schedules to try and resolve the conflict. For example, an older patient may elect not to be scheduled for night treatments due to driving restrictions as result of poor eyesight. As a result, the patient's profile, such as profile 4900 (FIG. 49), may reflect such a preference or restriction. Resolve operation 3124 then checks the preference and restriction profile portion to resolve any conflicts. Upon finishing the resolve operation 3124, an ideal patient schedule is provided to the user.

Last, an optional align operation 3126 may be implemented to align the night procedures. Night procedures are activities not related to patient care that employees do in preparation of closing the facility such as cleaning the machines, stocking supplies, etc. Other embodiments may not align the night procedures in order to distribute the employee requirements.

Figure 32:
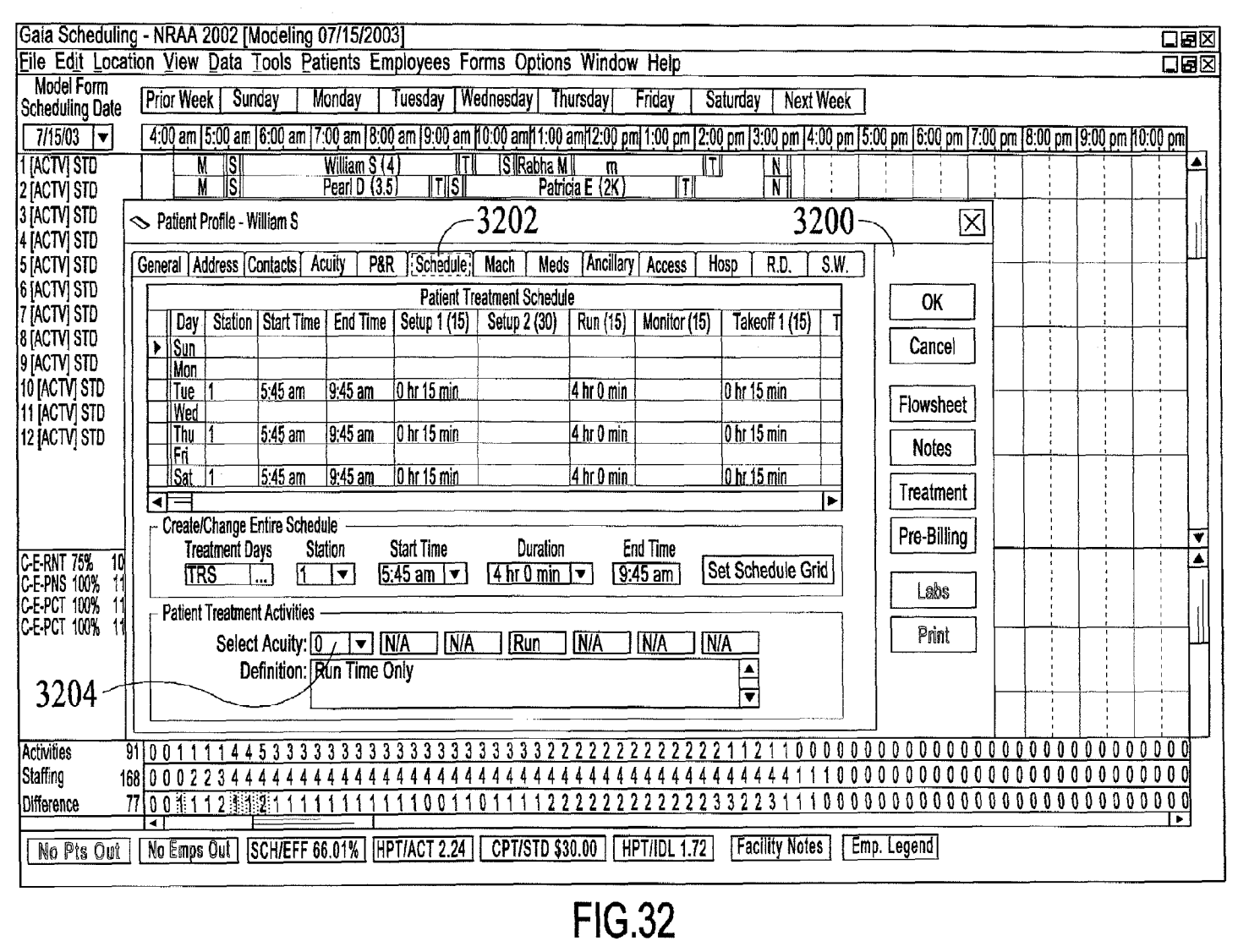

FIG. 32 illustrates a graphical user interface control 3200 used to display and, in some embodiments, to edit a patient profile. The profile 3200 may be accessed, in an embodiment, through the use of a right-click of a mouse while the mouse is hovering over a patient, such as shown in FIG. 8, and selecting the appropriate pop-up menu option, i.e., "Edit Patient Profile." The profile shown in FIG. 32 relates to "William S" and illustrates the many options available as data that can be entered and stored with respect to a patient. The present display, 3200 illustrates the information associated with tab 3202 showing schedule information. While the schedule information is displayed preferred treatment times, days, start time, etc. can be entered and stored with the patient profile. The control 3200 is similar to the control 632 shown in FIG. 9. However, in the embodiment shown in FIG. 32, the control 3200 also displays an acuity factor 3204. The patient acuity factor 3204 represents various generalized patient treatment activities that are stored in patient acuity arrays (discussed more specifically below in conjunction with FIGS. 33-39). In general however, the arrays combine known acuity factors, i.e., factors that require relatively predetermined quantities of direct patient care, such as setup time, takeoff time, etc. Once the arrays are generated, each patient can be assigned or associated with an acuity array 3204 from control 3200. The system can then schedule the appropriate number of direct patient care units to handle the patient during treatment.

Figure 33:
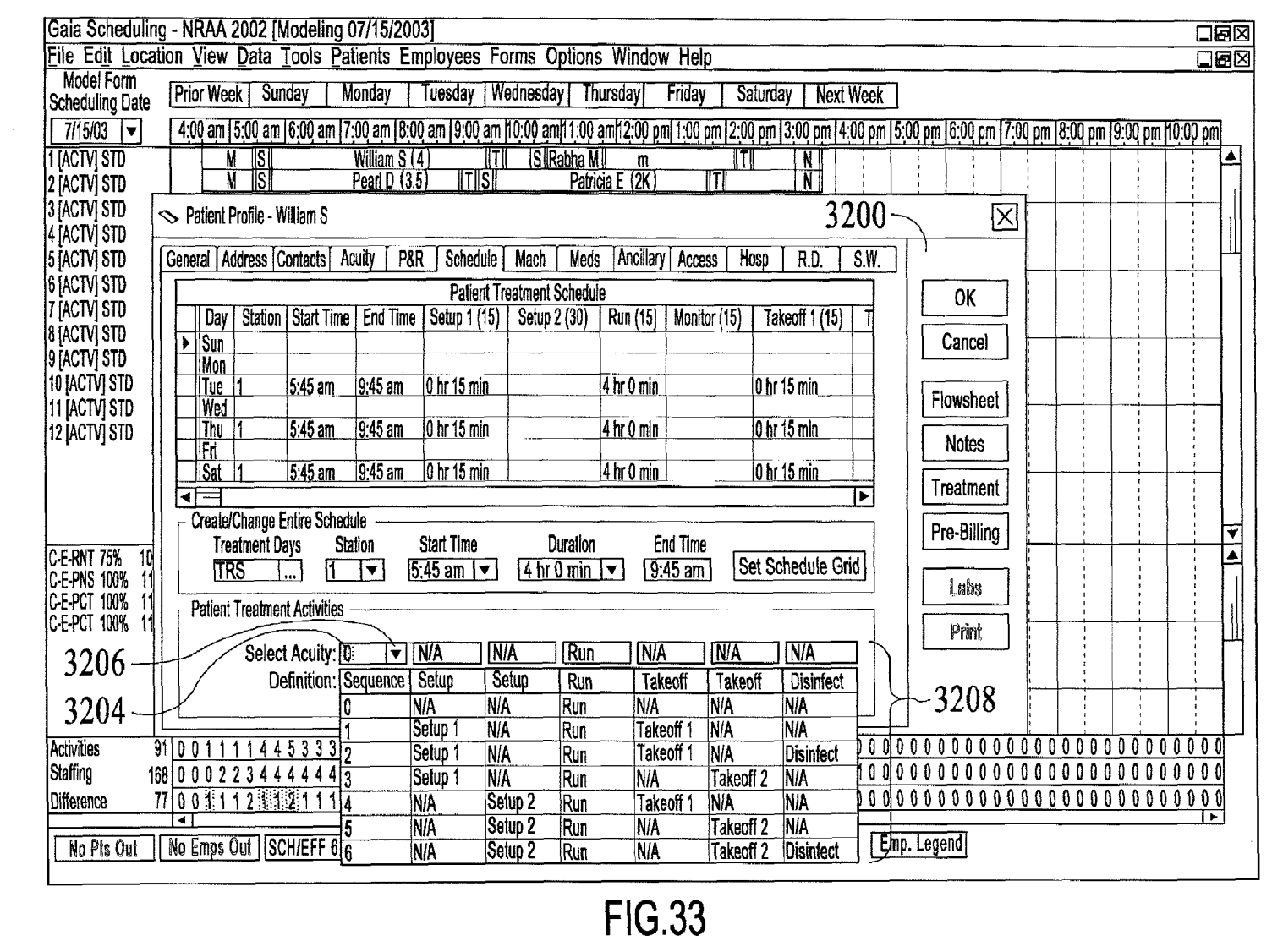

FIG. 33 illustrates one method of editing the acuity factor 3204 for a given patient. While the control 3200 is displayed, a user can select a drop down button 3206 to display the various patient acuity arrays 3208. Once displayed, the user can select one from the list and thereby associate the chosen array with the patient. The values related to the acuity factor, i.e., the acuity array are considered permanent acuity factors. Permanent acuity factors relate to the estimated known time that a particular patient requires direct patient care based on the history of that patient. Intermittent acuity factors are those unknown requirements discussed in more detail below.

Figure 34:
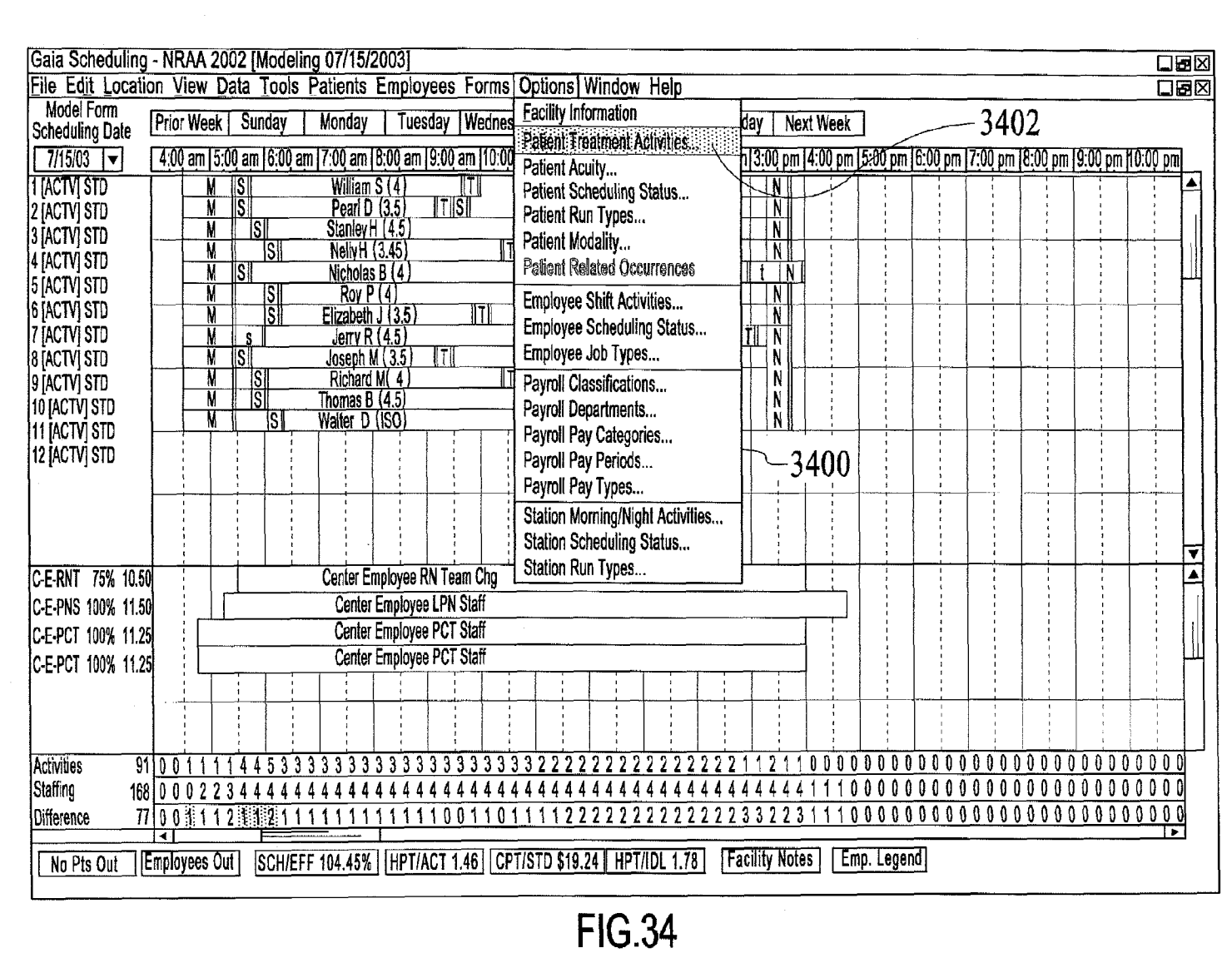
Figure 35:
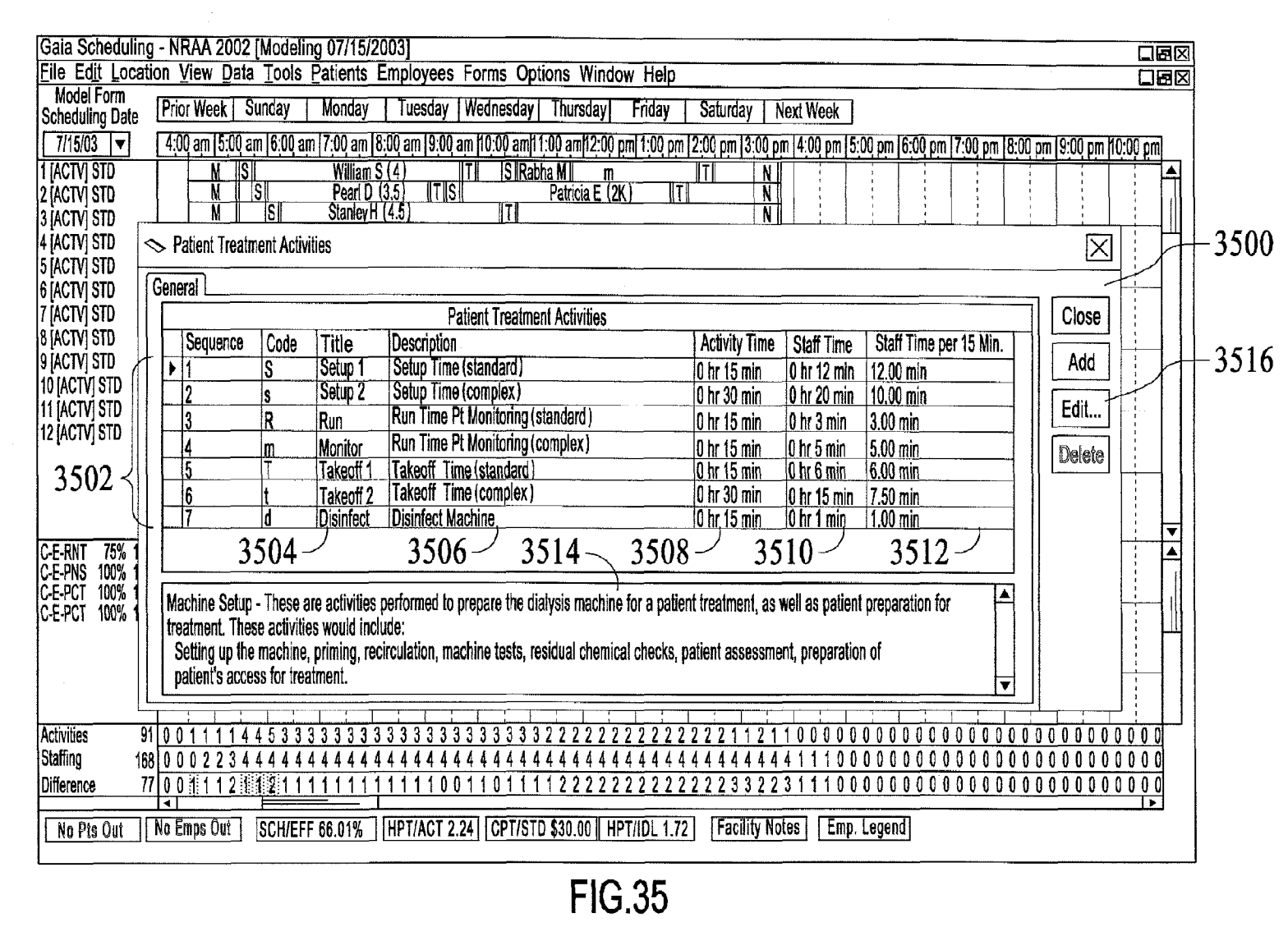

As may be appreciated, each patient acuity array categorizes various patient treatment activities and selects from a set of predetermined patient treatment activities. In order to create and/or edit patient treatment activities, a user may select the "Patient Treatment Activities" menu option from 3402 from drop down menu 3400, as shown in FIG. 34. Once selected, in an embodiment, control window 3500 is displayed, which displays the various treatment activities 3502. The treatment activities relate to sub parts of a hypothetical treatment, each having relatively predetermined direct patient care requirements. Some of the set 3502 of sub parts may be later combined into a full treatment, i.e., an acuity array and assigned to a particular patient as an acuity factor. As shown in FIG. 35, each treatment has a title 3504, a description 3506, and an activity time 3508 relating to the length of time the activity lasts. Also, each activity has an allotted staff time total 3510 and an allotted staff time per interval, e.g., per every 15 minute interval 3512. For example, as shown, there are two types of setup activities, one that is shown as standard and one that is described as complex. The activity time for the standard setup is 15 minutes while the activity time for the complex setup is 30 minutes. Also, the staff time required for the standard setup is 12 minutes and the required staff time for the complex setup is 20 minutes. Dividing the total staff time 3510 by the interval period, e.g., 15 minutes gives the staff time per interval value 3512, such as 12 minutes and 10 minutes, respectively for the standard and the complex setup activities.

Once a particular activity is highlighted or selected, a dashed line may be shown around the activity to illustrate that it has been selected. Moreover, a description 3514 of the selected activity may also be displayed to further inform the user of details regarding the selected activity. Also once selected the user may edit a particular activity by selecting the edit control 3516. Alternatively, the user may right-click an activity to create a pop-up window that provides an "edit activity" menu option, or, in other embodiments, the user may double click on an activity to edit the same.

Once the user has chosen to edit an activity, window 3600 may be displayed. Window 3600 provides many text control boxes for entering and editing the items 3504, 3506, 3508, 3510 and 3514 described above in conjunction with FIG. 35. As maybe appreciated, item 3512 is calculated based on items 3508 and 3510 such that no entering or editing of this item is required or available to the user. Further, although not shown, each patient activity may also be associated with an active/non-active toggle switch to allow users to activate or deactivate a patient activity. When an activity is inactive, the activity is not used in scheduling patients.

Figure 37:
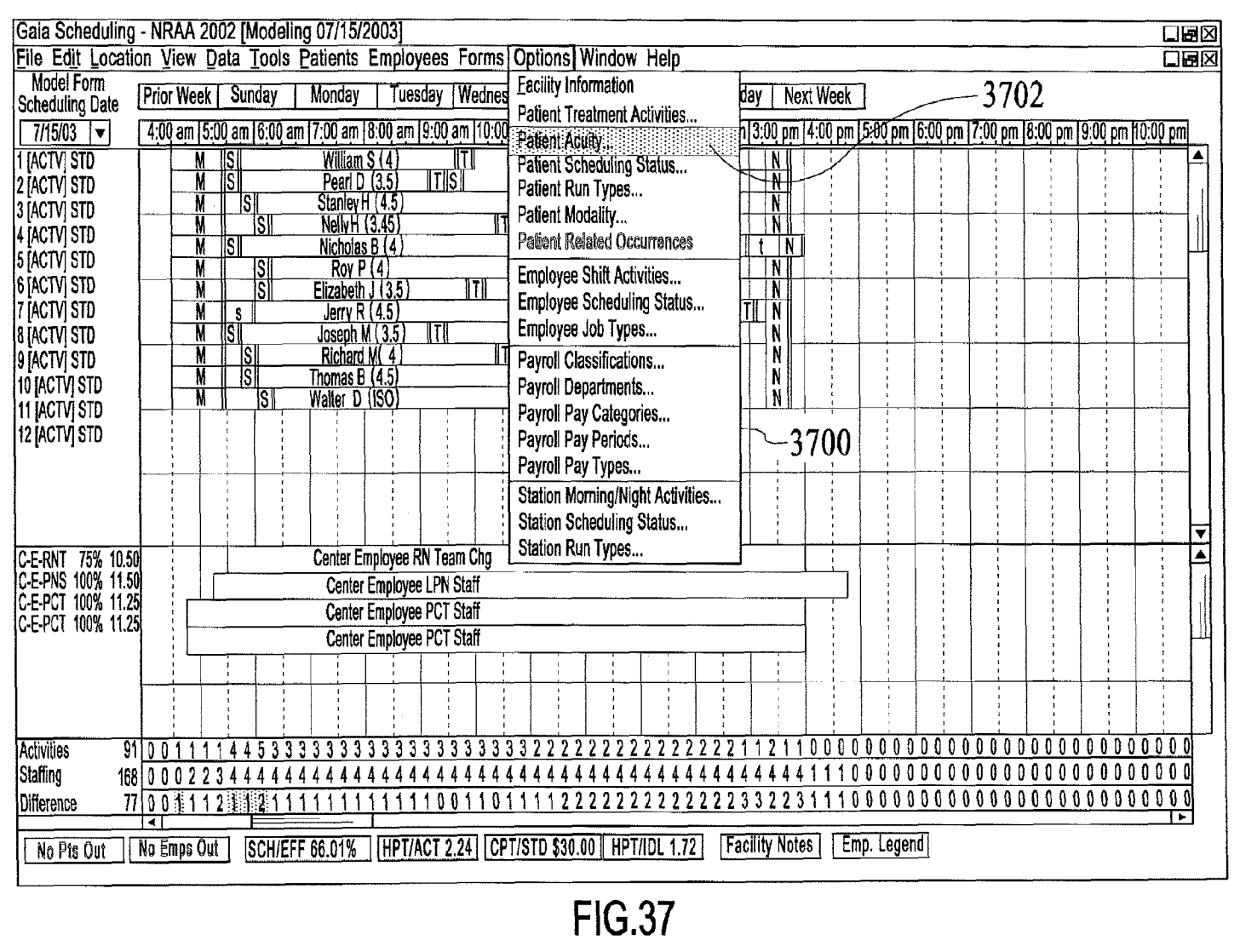
Figure 38:
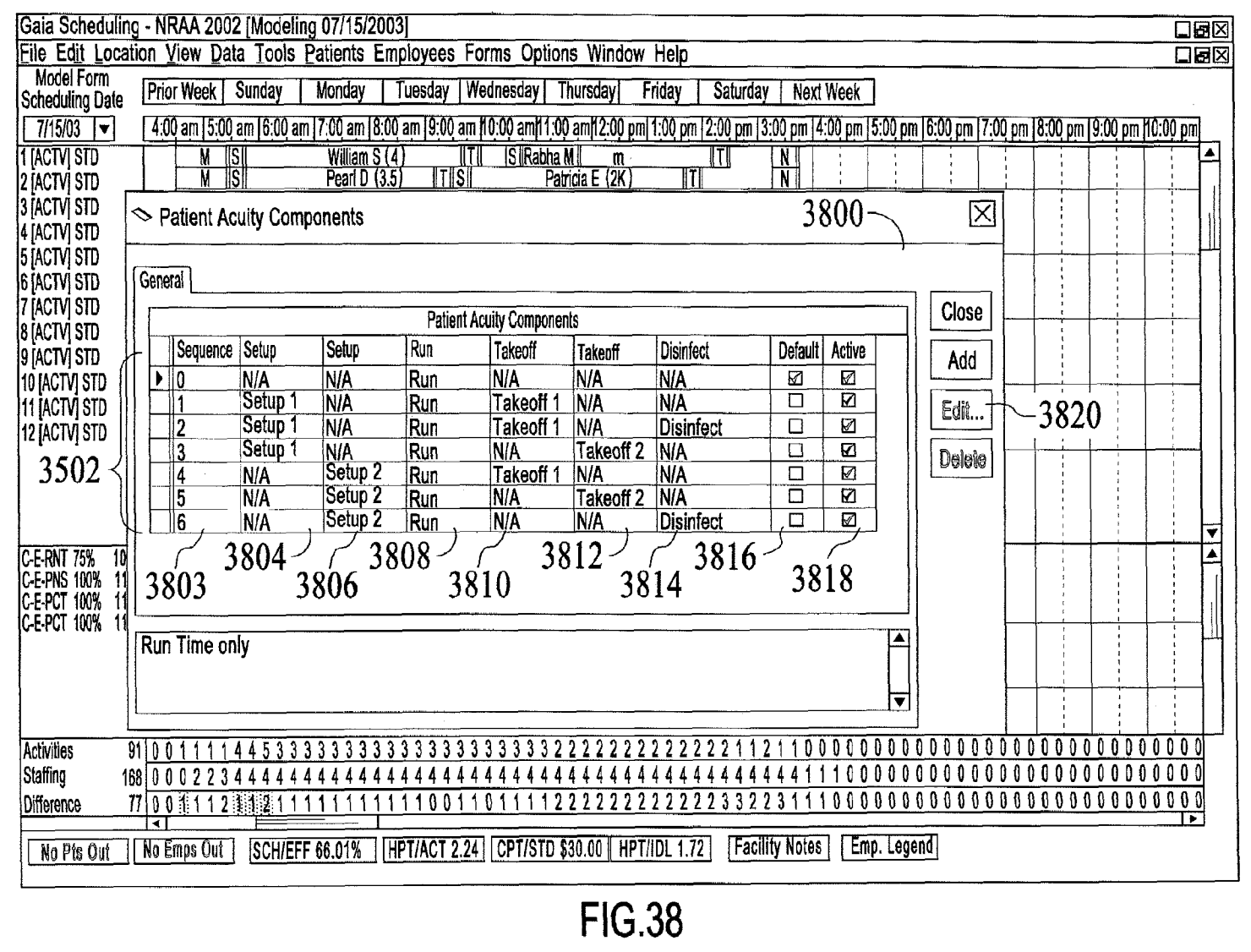

In order to create and/or edit the patient acuity arrays 3208 (FIG. 33), a user may select the "Patient Acuity . . . " menu option from 3702 from drop down menu 3700, as shown in FIG. 37. Once selected, in an embodiment, control window 3800 is displayed, which displays the various acuity arrays 3802. The arrays 3802 each have an identifying sequence number 3803 and a predetermined setup, e.g., setup 1, shown as 3804 or setup 2, shown in column 3806. Which setup assigned to which array is a user preference, but using this technique many different setup values may be used and assigned to a particular array. Since two separate setup procedures may not be required, i.e., a machine is assigned only one "setup" procedure which is all inclusive, the letters N/A for not applicable are displayed in the non-selected column regarding setup. Alternatively, the setup procedures may be broken out into separate smaller individual steps. Each array also has a run activity 3808, a takeoff activity, such as 3810 or 3812. As in the case with the different setup possibilities, the arrays 3802 may have different takeoff rates as well. Further, each array 3802 may be set to disinfect or not 3814. Further, each array may have a default toggle switch 3816 to change or select a default array. In an embodiment, only one array can be set to default at a time. Further, each array 3802 in the embodiment shown in FIG. 38 has an active/non-active toggle switch 3818. The active/non-active toggle switch allows a user to deactivate a sequence or array for one or more reasons, such as new technology that no longer requires certain procedural steps in the previously defined setup procedure. When an array is inactive, the array cannot be used.

Once a particular array is highlighted or selected, a dashed line may be shown around the activity to illustrate that it has been selected. Also once selected the user may edit a particular activity by selecting the edit control 3820. Alternatively, the user may right-click an activity to create a pop-up window that provides an "edit array" menu option, or, in other embodiments, the user may double click on an array to edit the same.

Once the user has chosen to edit an activity, window 3900 may be displayed. Window 3900 provides many text control boxes for entering and editing the items 3804, 3806, 3808, 3810, 3812, 3814, 3816 and 3818 described above in conjunction with FIG. 38. As may be appreciated, details of items 3804, 3806, 3808, 3810, 3812 and 3814, e.g., activity time and staff time are not edited from this window, instead, these items are edited from windows 3500 and 3600 discussed above in conjunction with FIGS. 35 and 36. Upon setting the various activities to be associated with an array, the user simply accepts the changes and closes window 3900.

Once an acuity array is selected for a patient all future treatment activities will be based on these specific treatment requirements. As stated above, these may be referred to as known or permanent acuity factors. The temporary or unknowable acuity factors are referred to as "intermittent acuity factors" and are used in calculating the ideal staff scheduling. The intermittent acuity factor is added to the known or permanent acuity factors that are defined and stored with a patient profile.

Figure 40:
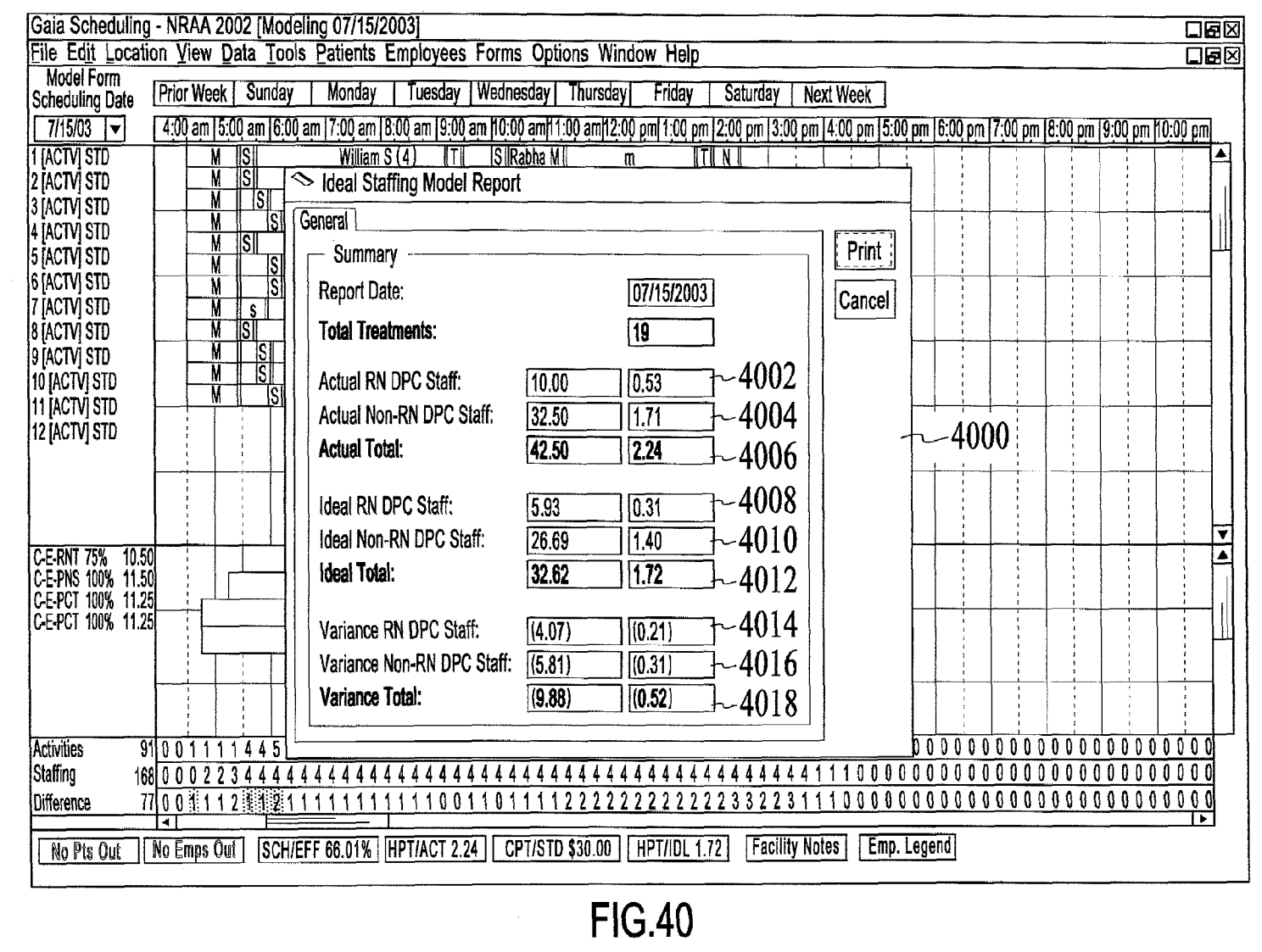

Once the patients have been scheduled and the employees have also been scheduled, the system may display an "Ideal Staffing Model Report" such as report 4000 shown in FIG. 40. The ideal staffing model displays both the actual RN direct patient care values, i.e., total and per treatment values 4002, the actual Non-RN direct patient care values 4004 and the sum totals of these values 4006. The actual values are taken directly from the actual employee schedule for the particular day. The report 4000 also displays the ideal RN direct patient care values, i.e., total and per treatment values 4008, the ideal Non-RN direct patient care values 4010 and the sum totals of these values 4012. The ideal values are calculated from the patient schedule, as described above, for the particular day. Last, the report 4000 also displays the variance values, between actual and ideal, for RN direct patient care 4014; for Non-RN direct patient care 4016; and for the totals 4018. Using report 4000, a user can readily determine the efficiency of a particular, actual schedule as compared to the calculated ideal in terms of RN to Non-RN employees.

Figure 47:
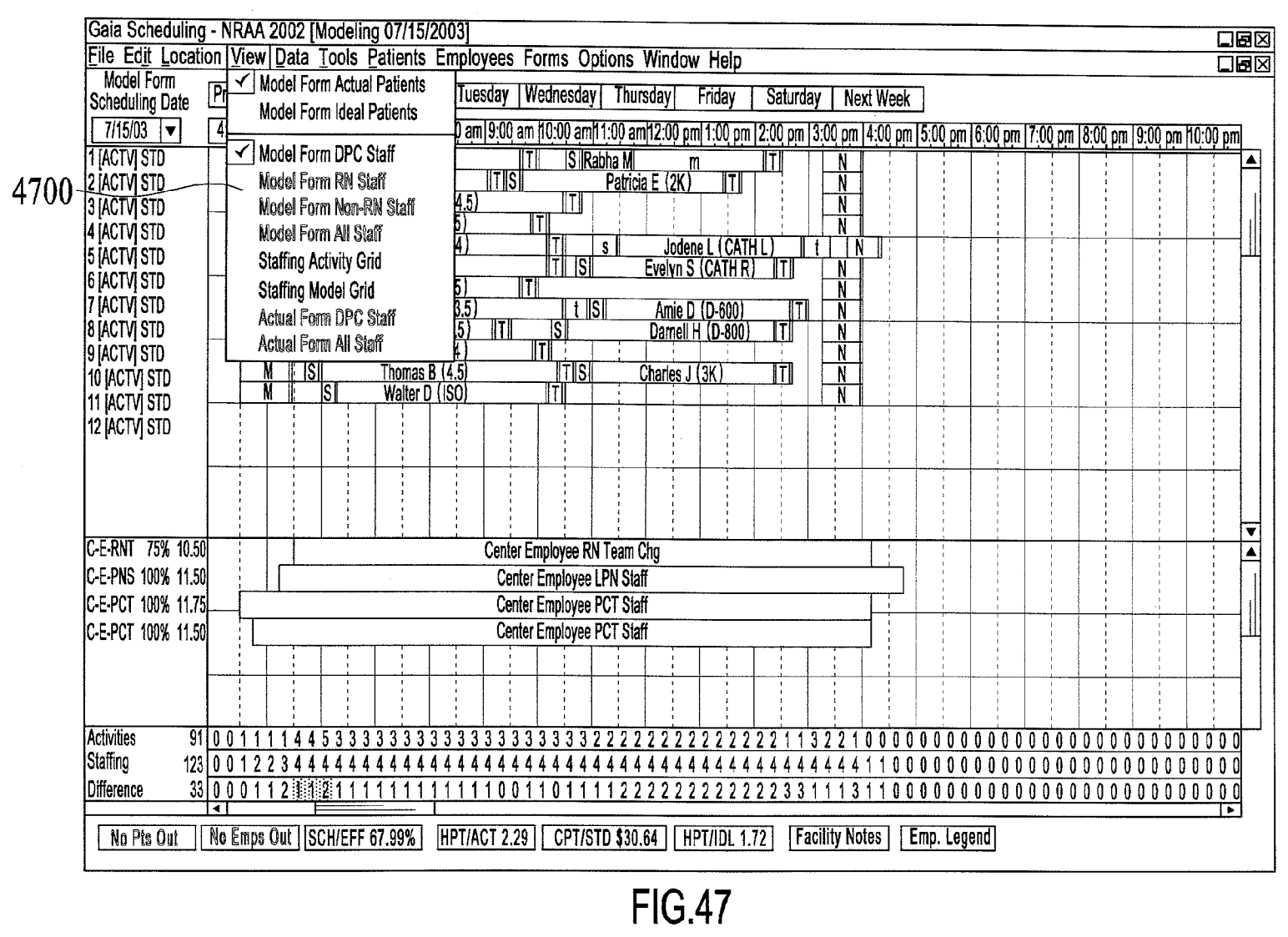

FIGS. 41-43 display three pages of yet another report that identifies the actual versus ideal data. As may be appreciated when a user adopts a staff modeling grid, such as through the view menu 4700 (FIG. 47) based on acceptable shift lengths, some employees will be scheduled during periods wherein fewer employees are expected to be providing direct patient care. Such inefficiencies are a direct result of employees not being available for very small, e.g. 15 minute or 30 minute shifts. Although this time may relate to an inefficiency, it becomes valuable in overall scheduling of employees since unplanned events occur that require additional direct patient care. The unplanned events, are foreseeable to some extent. That is, although unplanned, most clinical environments recognize the unavoidable catastrophe or other malfunctions do occur (i.e., intermittent acuity) such that all clinical environments attempt to schedule some ideal employee time to accommodate for such acuity. Since clinics desire some additional time, the efficiency calculation shown in FIGS. 41-43 accounts for this intermittent acuity value or percentage. Thus, overall efficiency is not a direct comparison of the ideal staff model and the actual employee schedule. Instead, the ideal staff model is adjusted to account for intermittent acuity and the result is compared to the actual employee schedule. The comparison provides an efficiency rating or value that can be tracked and used by the clinic.

In an embodiment, the intermittent acuity factor can be adjusted by the user. FIG. 26 illustrates a drop down box 2610 that allows a user to enter or edit the intermittent acuity factor used in producing the resulting reports shown in FIGS. 41-43. In other embodiments, the system may track actual intermittent acuity events to automatically calculate the percentage of time a particular clinic may expect to allocate employees in handling such activities.

In a particular embodiment, the ideal staff model 2902 (FIG. 29) is not calculated using the intermittent acuity factor. Instead, the difference in the results between the activity model 2700 (FIG. 27) and the staff model 2902 (FIG. 29) approximates the intermittent acuity factor. As stated above, the ideal activity model 2700 displays the actual time needed to care for known acuity factors, while the ideal staff model 2902 takes the results from the activity model and creates actual employee shifts. The creation of the actual employee shifts automatically creates inefficiencies in the ideal staff model that can be attributed to idle time for use in addressing intermittent acuity factors.

Figure 51:
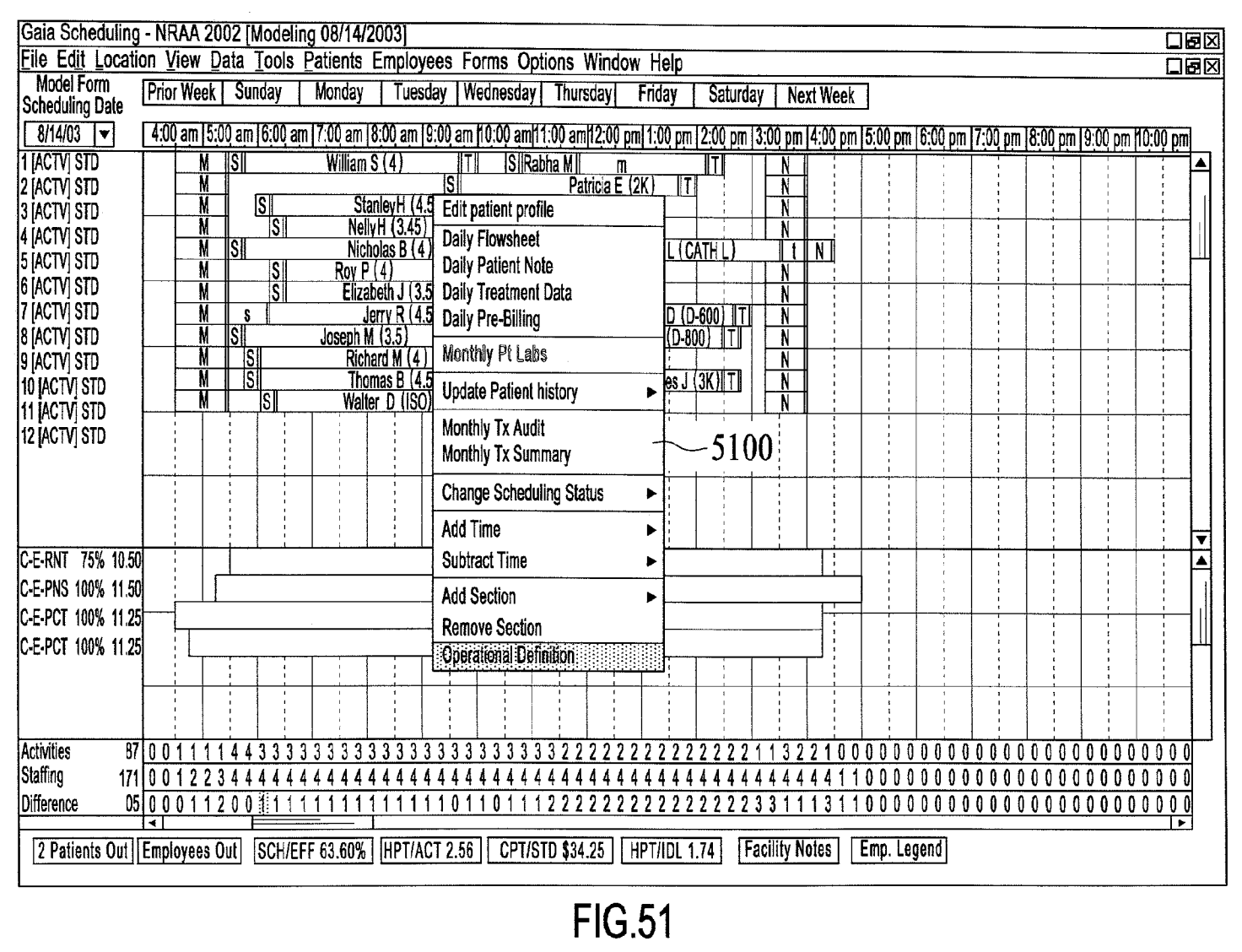
Figure 52:
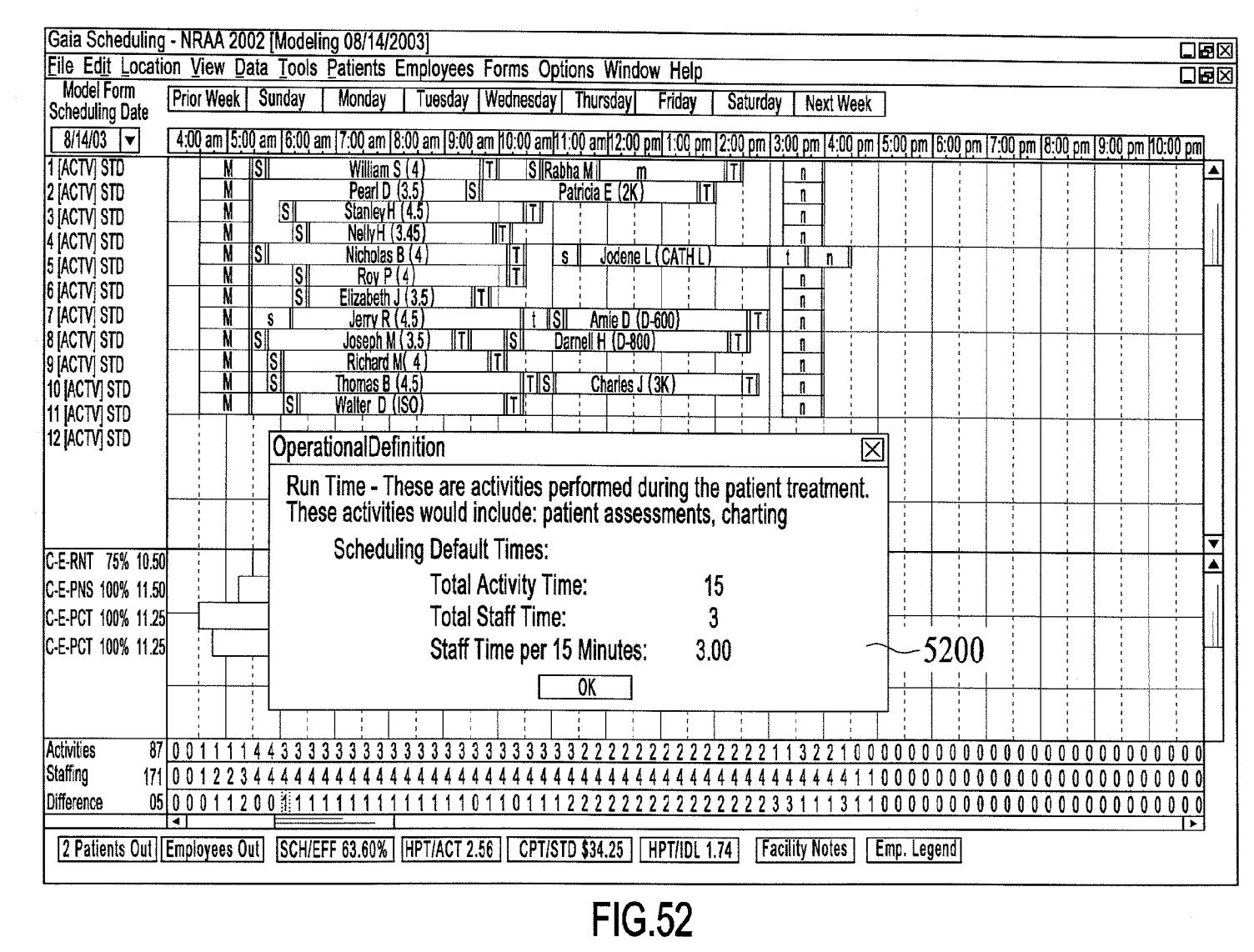

FIGS. 51-52 are screen shots illustrating user interface controls for displaying the operational definition of a particular section shown on the user interface, in accordance with an embodiment of the present invention. That is, when the mouse pointer or other cursor object is positioned over a section of the display, such as a patient schedule section or an employee schedule section, the user may right click the mouse (or otherwise send a selection command to the user interface) to create a pop-up menu, such as menu 5100 shown in FIG. 51. The menu includes an option titled "Operational Definition" which, when selected gives the operational definition for the item that the mouse was located on when the operational definition menu item was selected. For example, if the cursor is over the run time section in a patient scheduling section, and the operational definition menu option is selected, a pop-up window 5200 (FIG. 52) displays the predefined operation definition of the patient "run time" treatment activity. This would be the same for all selected operations definitions. The information displayed in window 5200 may involve the definition of the operation, the total activity time, the total staff time and the staff time per some predetermined time interval. The window may further include a control button to close the window.

As discussed above, the invention described herein may be implemented as a computer process, a computing system or as an article of manufacture such as a computer program product. The computer program product may be a computer storage medium readable by a computer system and encoding a computer program of instructions for executing a computer process. The computer program product may also be a propagated signal on a carrier readable by a computing system and encoding a computer program of instructions for executing a computer process.

Additionally, although the invention has been described in language specific to structural features and/or methodological steps, it is to be understood that the invention defined in the appended claims is not necessarily limited to the specific features or steps described. Therefore, the specific features and steps are disclosed as preferred forms of implementing the claimed invention.

What is claimed is:

1. A method of scheduling a plurality of employees in a health care environment, wherein at least two patients receive treatment during a predetermined time period, said scheduling method comprising:

for each patient, evaluating patient care requirements, wherein the patient care requirements correspond to actual employee time requirements necessary to satisfy the patient care requirements;

in response to the patient care requirement evaluation, adjusting scheduling time of at least one patient to distribute the corresponding employee time requirements throughout a predetermined time period;

automatically scheduling employees in shifts in response to the distributed employee time requirements, wherein automatically scheduling employees comprises:
(i) determining in a computer system the employees' patient care capability over intervals of their shift, wherein at least one employee is not capable of performing direct patient care duties for an entire shift;
(ii) counting employees at a fractional number based at least upon the employees' training and a predetermined patient care capability resulting in scheduling employees in non-whole number increments; and
(iii) rounding up a total amount of employees needed when a determination by a scheduling module results in a fractional number of employees needed to address the needs of the at least two patients; and displaying employee shift information in relation to time to provide a visual indication of scheduled employee information in relation to scheduled patient information.

2. A method as defined in claim 1 wherein the act of automatically scheduling the employees comprises:
defining a predetermined number of job-types, wherein each job-type has an associated skill level;
scheduling job-types to accommodate the patient requirements; and
associating employees with the scheduled job-types.

3. A method as defined in claim 2 wherein the predetermined time period is a day, the method further comprising:
dividing the day into intervals; and
in evaluating the patient care requirements, determining the patient care requirements on a per-interval basis.

4. A method as defined in claim 3 wherein the patient care requirements are averaged over more than one interval.

5. A method as defined in claim 2 further comprising:
defining acceptable shift lengths; and
scheduling job types based on acceptable shift lengths.

6. A method as defined in claim 2 wherein each employee has a predetermined patient care capability and wherein the method further comprises scheduling employees in relation to patient care capability.

7. A method as defined in claim 6 wherein the patient care capability relates to indirect and direct patient care activities.

8. A method as defined in claim 7 wherein each employee further has a predetermined non-patient care capability relating to performing non-patient care activities, and wherein the method further comprises:
calculating a staff efficiency valued based on scheduled activities, wherein the scheduled activities relate to patient care and non-patient care activities and wherein the staff efficiency evaluates hours of direct patient care required per treatment activity.

9. A method as defined in claim 2 further comprising:
dividing the predetermined time into intervals; and
displaying a plurality of patient schedules in relation to time to provide a visual indication of the patient care requirements for each interval.

10. A method as defined in claim 9 further comprising calculating patient requirement values related to required employees based on the patient care requirements for a plurality of intervals and displaying the calculated values.

11. A method as defined in claim 10 further comprising displaying employee shift information in relation to time to provide a visual indication of scheduled employee information in relation to scheduled patient information.

12. A method as defined in claim 1 further comprising:
calculating a total value of employee time for each interval;
displaying the calculated employee values in a grid form; and
comparing patient requirement values and employee values for each interval to determine efficiency.

13. A method as defined in claim 1 wherein the act of adjusting the scheduling times of the patients comprises automatically staggering the start time of at least two patients to allow one employee to substantially service the needs of the at least two patients based on a predetermined stagger value.

14. A method as defined in claim 13 further comprising:
entering an idle time; and
automatically scheduling subsequent patients based on the idle time.

15. A method as defined in claim 1 wherein the act of automatically scheduling the employees further comprises:
generating an ideal staff model, based on job types;
using the ideal staff model, generating an ideal staff schedule; and
displaying the ideal staff model.

16. A method as defined in claim 15 further comprising associating employees with the ideal staff model to finalize the employee schedule.

17. A method as defined in claim 16 further comprising:
defining a set of drivers to define the rules in creating the ideal staff model.

18. A method as defined in claim 17 wherein the drivers comprise:
a nurse to non-nurse employee ratio;
a direct patient care percentage value for nurses; and
a direct patient care percentage value for non-nurses.

19. A method as defined in claim 18 further comprising:
calculating an efficiency value for a schedule wherein the efficiency value accommodates for intermittent patient acuity.

20. A method of scheduling employees in a health care environment comprising:
compiling a plurality of patient profiles, each patient profile associated with a different patient, and wherein each patient profile comprises information related to the direct patient care needs of the associated patient;
compiling a plurality of employee profiles, each employee profile associated with a different employee and wherein each employee profile comprises information related to the patient care capability of the associated employee;
calculating scheduling efficiency information relating to a generated schedule of patients and employees based on the patient profiles and employee profiles;
scheduling employees in shifts according to distributed employee time requirements and automatically adjusting the schedule to generate a more efficient schedules, wherein scheduling comprises:
(i) determining in a computer system the employees' patient care capability over intervals of their shift, wherein at least one employee is not capable of performing direct patient care duties for an entire shift;
(ii) counting employees at a fractional number based at least upon the employees' training and a predetermined patient care capability resulting in scheduling employees in non-whole number increments; and
(iii) rounding up a total amount of employees needed when a determination by a scheduling module results in a fractional number of employees needed to address the needs of the plurality of patients; and
displaying employee shift information in relation to time to provide a visual indication of scheduled employee information in relation to scheduled patient information.

21. A method as defined in claim 20 wherein the act of automatically adjusting the schedule comprises:
   entering a stagger time;
   entering an idle time; and
   automatically shifting the patient schedules based on the stagger time and the idle time.

22. A method as defined in claim 21 further comprising:
   automatically adjusting the employee schedules in response to the automatic shifting of the patient schedules.

23. A method as defined in claim 22, wherein the act of automatically shifting the patient schedules further comprises evaluating the patient profiles to resolve conflicts.

24. A method as defined in claim 23 wherein the act of automatically adjusting employee schedules further comprises evaluating the employee profiles to resolve conflicts.

25. A system for scheduling employees in a health care environment comprising:
   a memory store for storing patient information related to the needs of a plurality of patients, resource information and employee information related to patient care capability of a plurality of patients;
   a scheduling module that schedules patients and employees according to patient needs and schedules employees in shifts according to distributed employee time requirements, wherein scheduling comprises:
      (i) determining the employees' patient care capability over intervals of their shift, wherein at least one employee is not capable of performing direct patient care duties for an entire shift;
      (ii) counting employees at a fractional number based at least upon the employees' training and a predetermined patient care capability resulting in scheduling employees in non-whole number increments; and
      (iii) rounding up a total amount of employees needed when a determination by the scheduling module results in a fractional number of employees needed to address the needs of the plurality of patients;
   an optimization module for adjusting a schedule to optimize efficiency, wherein adjusting the schedule comprises adjusting the scheduled patient information and automatically adjusting the scheduled employee information to reflect the change; and
   a display unit for displaying the scheduled patient information in combination with scheduled employee information, the display providing efficiency information.

26. A system as defined in claim 25 wherein the scheduling module further calculates the needs of each patient based on a per-interval.

27. A system as defined in claim 26 wherein the calculated needs of the employees and patients are displayed on the display unit.

28. A system as defined in claim 27 wherein the scheduling module further calculates a comparison value related to patient requirements and employee capabilities for each interval, said comparison values displayed on the display unit.

29. A system as defined in claim 28 wherein the calculated values are automatically updated and displayed following a modification to the employee schedule information.

30. A system as defined in claim 27 wherein the calculated values are automatically updated and displayed following a modification to the patient schedule information.

31. A system as defined in claim 27 wherein the optimization module compensates for intermittent acuity in determining an ideal staffing model, wherein the intermittent acuity relates to staff idle time when no unplanned patient requirements occur.

32. A system as defined in claim 27 further comprising a calculation module that calculates total patient treatment times, hours per treatment time and determines the efficiency of a schedule based on the hours per treatment time.

33. A system as defined in claim 25 wherein adjusting the scheduled patient information comprises moving the scheduled patient information from a first interval to a second interval.

34. A graphical user interface for a computer system, the graphical user interface having a display module for displaying information; said graphical user interface comprising:
   a patient schedule portion, the patient schedule portion logically divided into intervals and displaying patient schedule information related to the intervals;
   an employee schedule portion logically divided into intervals, wherein the employee schedule portion is determined by:
      (i) an employees' patient care capability over the intervals, wherein at least one employee is not capable of performing direct patient care duties for an entire shift;
      (ii) counting employees at a fractional number based at least upon the employees' training and a predetermined patient care capability resulting in scheduling employees in non-whole number increments;
      (iii) rounding up a total amount of employees needed when a determination by a scheduling module results in a fractional number of employees needed to address the needs of a plurality of patients, and wherein the intervals for the patient schedule portion correspond to the intervals for the employee information portion; and
   a calculation display area for displaying calculated values within each interval, the calculated values relating to patient care requirements, the display area graphically depicting peaks related in relative increases in patient requirements for each interval such that the calculation display area provides efficiency information.

35. A graphical user interface as defined in claim 34 wherein the calculated values are automatically updated when the displayed information in either the patient schedule portion or the employee schedule portion is modified.

* * * * *